(12) United States Patent
Dineen

(10) Patent No.: US 10,829,493 B2
(45) Date of Patent: Nov. 10, 2020

(54) COMPOSITIONS AND METHODS FOR TREATING KIT- AND PDGFRA-MEDIATED DISEASES

(71) Applicant: Blueprint Medicines Corporation, Cambridge, MA (US)

(72) Inventor: Thomas A. Dineen, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 16/842,969

(22) Filed: Apr. 8, 2020

(65) Prior Publication Data

US 2020/0325141 A1 Oct. 15, 2020

Related U.S. Application Data

(60) Provisional application No. 62/930,240, filed on Nov. 4, 2019, provisional application No. 62/911,016, filed on Oct. 4, 2019, provisional application No. 62/833,529, filed on Apr. 12, 2019.

(51) Int. Cl.
| | |
|---|---|
| *C07D 487/04* | (2006.01) |
| *A61P 35/00* | (2006.01) |
| *A61P 43/00* | (2006.01) |

(52) U.S. Cl.
CPC ............ *C07D 487/04* (2013.01); *A61P 43/00* (2018.01)

(58) Field of Classification Search
CPC .................................................. C07D 487/04
See application file for complete search history.

(56) References Cited

U.S. PATENT DOCUMENTS

| | | |
|---|---|---|
| 6,982,265 B1 | 1/2006 | Hunt et al. |
| 7,244,733 B2 | 7/2007 | Hunt et al. |
| 8,609,672 B2 | 12/2013 | Russu et al. |
| 9,200,002 B2 | 12/2015 | Hodous et al. |
| 9,334,263 B2 | 5/2016 | Hodous et al. |
| 9,499,522 B2 | 11/2016 | DiPietro et al. |
| 9,688,680 B2 | 6/2017 | Hodous |
| 9,884,861 B2 | 2/2018 | Hodous et al. |
| 9,944,651 B2 | 4/2018 | Hodous et al. |
| 9,994,552 B2 | 6/2018 | DiPietro et al. |
| 9,994,575 B2 | 6/2018 | Hodous et al. |
| 10,000,496 B2 | 6/2018 | Hodous et al. |
| 2004/0186140 A1 | 9/2004 | Cherney et al. |

FOREIGN PATENT DOCUMENTS

| | | |
|---|---|---|
| CN | 102040494 | 5/2011 |
| CN | 108191874 A | 6/2018 |
| CN | 110938077 A | 3/2020 |
| CN | 110950872 A | 4/2020 |
| EP | 0200968 A1 | 11/1986 |
| JP | 2008-504366 A | 2/2008 |
| WO | 2000/71129 A1 | 11/2000 |
| WO | 2001/25220 A1 | 4/2001 |
| WO | 2003/010158 A1 | 2/2003 |
| WO | 2003/090912 A1 | 11/2003 |
| WO | 2004/071460 A2 | 8/2004 |
| WO | 2004/076450 A1 | 9/2004 |
| WO | 2005/117909 A2 | 12/2005 |
| WO | 2006/004636 A2 | 1/2006 |
| WO | 2006/028524 A2 | 3/2006 |
| WO | 2007/056170 A2 | 5/2007 |
| WO | 2007/065100 A1 | 6/2007 |
| WO | 2007/085188 A1 | 8/2007 |
| WO | 2008/005956 A2 | 1/2008 |
| WO | 2009/015254 A1 | 1/2009 |
| WO | 2009/117157 A1 | 9/2009 |

(Continued)

OTHER PUBLICATIONS

Dhillon, Drugs (2020) 80:433-439. (Year: 2020).*

(Continued)

*Primary Examiner* — Emily A Bernhardt
(74) *Attorney, Agent, or Firm* — McCarter & English, LLP; Steven G. Davis; Wei Song

(57) ABSTRACT

The present disclosure provides compounds of Formula I,

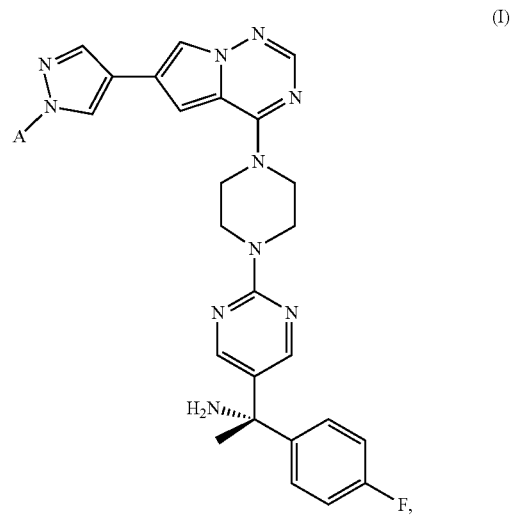

pharmaceutical salts thereof, and/or solvates of any of the foregoing, which are useful for treating diseases and conditions related to mutant KIT and PDGFRα and present an advantageously non-brain penetrant profile for treating diseases and conditions related to mutant KIT and PDGFRα. The present disclosure also provides methods for treating gastrointestinal stromal tumors and systemic mastocytosis.

41 Claims, No Drawings

Specification includes a Sequence Listing.

(56) References Cited

FOREIGN PATENT DOCUMENTS

| WO | 2010/022055 A2 | 2/2010 |
| --- | --- | --- |
| WO | 2010/144345 A1 | 12/2010 |
| WO | 2011/005119 A1 | 1/2011 |
| WO | 2011/103196 A1 | 8/2011 |
| WO | 2012/027495 A1 | 3/2012 |
| WO | 2014/039714 A2 | 3/2014 |
| WO | 2014/100620 A2 | 6/2014 |
| WO | 2014/160521 A1 | 10/2014 |
| WO | 2015/057873 A1 | 4/2015 |
| WO | 2015/058129 A1 | 4/2015 |
| WO | 2016/022569 A1 | 2/2016 |
| WO | 2017/019442 A1 | 2/2017 |
| WO | 2018/183712 A1 | 10/2018 |
| WO | 2019/034128 A1 | 2/2019 |
| WO | 2020/102095 A1 | 5/2020 |

OTHER PUBLICATIONS

Antonescu, What lessons can be learned from the GIST paradigm that can be applied to other kinase-driven cancers. J Pathol. Jan. 2011;223(2):251-261.

Cairoli et al., Prognostic impact of c-KIT mutations in core binding factor leukemias: an Italian retrospective study. Blood. May 1, 2006;107(9):3463-8.

Cohen, The development and therapeutic potential of protein kinase inhibitors. Curr Opin Chem Biol. Aug. 1999;3(4):459-65.

Lee et al., Correlation of imatinib resistance with the mutational status of KIT and PDGFRA genes in gastrointestinal stromal tumors: a meta-analysis. J Gastrointestin Liver Dis. Dec. 2013;22(4):413-8.

Paschka et al., Adverse prognostic significance of KIT mutations in adult acute myeloid leukemia with inv(16) and t (8;21): a Cancer and Leukemia Group B Study. J Clin Oncol. Aug. 20, 2006;24(24):3904-11.

Quintela et al., A Ready One-pot Preparation for Pyrrolo[2,1-f]-[1,2,4]triazine and Pyrazolo[5,1-c]pyrimido[4,5-e]-[1,2,4]triazine Derivatives. Tetrahedron. 1996;52(8):3037-3048.

Schnittger et al., KIT-D816 mutations in AML1-ETO-positive AML are associated with impaired event-free and overall survival. Blood. 2006;107:1791-1799.

Shallal et al., Discovery, synthesis, and investigation of the antitumor activity of novel piperazinylpyrimidine derivatives. Eur J Med Chem. Jun. 2011;46(6):2043-57.

Di et al., Demystifying brain penetration in central nervous system drug discovery. Miniperspective. J Med Chem. 2013;56(1):2-12.

Evans et al., A precision therapy against cancers driven by KIT/PDGFRA mutations. Sci Transl Med. 2017;9(414): eaao1690, 11 pages.

Rankovic, CNS drug design: balancing physicochemical properties for optimal brain exposure. J Med Chem. 2015;58(6):2584-2608.

* cited by examiner

SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Oligopeptide

<400> SEQUENCE: 1

Glu Val Gln Trp Lys
1               5

<210> SEQ ID NO 2
<211> LENGTH: 18
<212> TYPE: PRT
<213> ORGANISM: Artificial Sequence
<220> FEATURE:
<223> OTHER INFORMATION: Oligopeptide

<400> SEQUENCE: 2

Glu Val Gln Trp Lys Val Val Glu Glu Ile Asn Gly Asn Asn Tyr Val
1               5                   10                  15

Tyr Ile

<210> SEQ ID NO 3
<211> LENGTH: 9
<212> TYPE: PRT
<213> ORGANISM: Artificial Sequence
<220> FEATURE:
<223> OTHER INFORMATION: Oligopeptide

<400> SEQUENCE: 3

Lys Pro Met Tyr Glu Val Gln Trp Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Oligopeptide

<400> SEQUENCE: 4

Lys Pro Met Tyr Glu Val Gln Trp
1               5

<210> SEQ ID NO 5
<211> LENGTH: 6
<212> TYPE: PRT
<213> ORGANISM: Artificial Sequence
<220> FEATURE:
<223> OTHER INFORMATION: Oligopeptide

<400> SEQUENCE: 5

Met Tyr Glu Val Gln Trp
1               5

<210> SEQ ID NO 6
<211> LENGTH: 4
<212> TYPE: PRT
<213> ORGANISM: Artificial Sequence
<220> FEATURE:
<223> OTHER INFORMATION: Oligopeptide

```
<400> SEQUENCE: 6

Pro Met Tyr Glu
1

<210> SEQ ID NO 7
<211> LENGTH: 5
<212> TYPE: PRT
<213> ORGANISM: Artificial Sequence
<220> FEATURE:
<223> OTHER INFORMATION: Oligopeptide

<400> SEQUENCE: 7

Trp Lys Val Val Glu
1               5

<210> SEQ ID NO 8
<211> LENGTH: 4
<212> TYPE: PRT
<213> ORGANISM: Artificial Sequence
<220> FEATURE:
<223> OTHER INFORMATION: Oligopeptide

<400> SEQUENCE: 8

Trp Lys Val Val
1

<210> SEQ ID NO 9
<211> LENGTH: 6
<212> TYPE: PRT
<213> ORGANISM: Artificial Sequence
<220> FEATURE:
<223> OTHER INFORMATION: Oligopeptide

<400> SEQUENCE: 9

Tyr Glu Val Gln Trp Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Oligopeptide

<400> SEQUENCE: 10

Arg Val Ile Glu Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Oligopeptide

<400> SEQUENCE: 11

Ser Pro Asp Gly His Glu
1               5

<210> SEQ ID NO 12
<211> LENGTH: 5
<212> TYPE: PRT
<213> ORGANISM: Artificial Sequence
<220> FEATURE:
<223> OTHER INFORMATION: Oligopeptide
```

```
<400> SEQUENCE: 12

Tyr Asp Ser Arg Trp
1               5

<210> SEQ ID NO 13
<211> LENGTH: 4
<212> TYPE: PRT
<213> ORGANISM: Artificial Sequence
<220> FEATURE:
<223> OTHER INFORMATION: Oligopeptide

<400> SEQUENCE: 13

Asp Ile Met His
1

<210> SEQ ID NO 14
<211> LENGTH: 4
<212> TYPE: PRT
<213> ORGANISM: Artificial Sequence
<220> FEATURE:
<223> OTHER INFORMATION: Oligopeptide

<400> SEQUENCE: 14

Ile Met His Asp
1

<210> SEQ ID NO 15
<211> LENGTH: 4
<212> TYPE: PRT
<213> ORGANISM: Artificial Sequence
<220> FEATURE:
<223> OTHER INFORMATION: Oligopeptide

<400> SEQUENCE: 15

Met His Asp Ser
1

<210> SEQ ID NO 16
<211> LENGTH: 5
<212> TYPE: PRT
<213> ORGANISM: Artificial Sequence
<220> FEATURE:
<223> OTHER INFORMATION: Oligopeptide

<400> SEQUENCE: 16

Asp Ile Met His Asp
1               5

<210> SEQ ID NO 17
<211> LENGTH: 5
<212> TYPE: PRT
<213> ORGANISM: Artificial Sequence
<220> FEATURE:
<223> OTHER INFORMATION: Oligopeptide

<400> SEQUENCE: 17

Ile Met His Asp Ser
1               5

<210> SEQ ID NO 18
<211> LENGTH: 4
<212> TYPE: PRT
<213> ORGANISM: Artificial Sequence
<220> FEATURE:
<223> OTHER INFORMATION: Oligopeptide
```

```
<400> SEQUENCE: 18

His Asp Ser Asn
1

<210> SEQ ID NO 19
<211> LENGTH: 12
<212> TYPE: PRT
<213> ORGANISM: Artificial Sequence
<220> FEATURE:
<223> OTHER INFORMATION: Oligopeptide

<400> SEQUENCE: 19

Lys Lys Lys Lys Asp Asp Ile Tyr Phe Phe Phe Gly
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Oligopeptide

<400> SEQUENCE: 20

Gly Glu Glu Pro Leu Tyr Trp Ser Phe Pro Ala Lys Lys Lys
1               5                   10
```

COMPOSITIONS AND METHODS FOR TREATING KIT- AND PDGFRA-MEDIATED DISEASES

This application claims priority from U.S. Provisional Application No. 62/833,529, filed Apr. 12, 2019; U.S. Provisional Application No. 62/911,016, filed Oct. 4, 2019; and U.S. Provisional Application No. 62/930,240, filed Nov. 4, 2019. The entire contents of each of the aforementioned applications are incorporated herein by reference.

The instant application contains a Sequence Listing which has been filed electronically in ASCII format and is hereby incorporated by reference in its entirety. Said ASCII copy, created on Apr. 24, 2020, is named Seqlist_SL25.txt and is 3,821 bytes in size.

This disclosure relates to novel pyrrolotriazine compounds and their use as selective inhibitors of activated KIT and PDGFRα mutant protein kinases. The compounds disclosed herein are useful in pharmaceutical compositions, such as, e.g., for the treatment of chronic disorders. The KIT receptor belongs to the class III receptor tyrosine kinase family that also includes the structurally related protein PDGFRα. Normally, stem cell factor binds to and activates KIT by inducing dimerization and autophosphorylation, which induces initiation of downstream signaling. In several tumor types, however, somatic activating mutations in KIT drive ligand-independent constitutive oncogenic activity, including tumor types such as acute myeloid leukemia, melanoma, intercranial germ cell tumors, mediastinal B-cell lymphoma, seminoma, and gastrointestinal stromal tumors. Mutant KIT is also known to play a role in mast cell activation, which is common and possibly necessary for maintenance. Disordered mast cell activation occurs when mast cells are pathologically overproduced or if their activation is out of proportion to the perceived threat to homeostasis. Mast cell activation syndrome refers to a group of disorders with diverse causes presenting with episodic multisystem symptoms as the result of mast cell mediator release. Mastocytosis is one type of mast cell activation syndrome. The World Health Organization (WHO) classifies mastocytosis into 7 different categories: cutaneous mastocytosis, indolent systemic mastocytosis (ISM), smoldering systemic mastocytosis (SSM), mastocytosis with an associated hematologic neoplasm (SM-AHN), aggressive systemic mastocytosis (ASM), mast cell leukemia (MCL) and mast cell sarcoma Systemic mastocytosis is a clonal disorder of mast cells characterized by increased mast cell burden, with focal and/or diffuse infiltrates of neoplastic mast cells in the skin, bone marrow, spleen, liver, gastrointestinal tract, and other organs, and increased release of mast cell mediators. SM includes 5 sub-types mastocytosis: indolent SM (ISM), smoldering SM (SSM), SM with an associated hematologic neoplasm of non-MC lineage (SM-AHN), aggressive SM (ASM), and MC leukemia (MCL). The latter three sub-classifications are associated with reduced overall survival and are grouped together as advanced SM (AdvSM). ISM is a chronic disorder associated with a normal or near-normal life-expectancy and the prognosis of SSM is intermediate. ISM and SSM are grouped together as non-advanced SM (non-Adv SM).

In all subtypes of SM, and in a majority of patients with the disease, neoplastic mast cells display a mutation at the D816 position in exon 17 of KIT, which results in ligand-independent activation of KIT kinase activity. Wild-type mast cells require KIT activity for their differentiation and survival and, therefore, constitutive activation of KIT through D816V mutation is thought to be a pathogenic driver for SM. Specifically, KIT D816V mutations are found in 90% to 98% of patients with SM, with rare KIT D816Y, D816F, and D816H variants identified. Based on these findings, KIT D816V is considered a major therapeutic target in SM.

The chronic disorders indolent SM and SSM are characterized by severe symptoms, including pruritus, flushing, GI cramping, diarrhea, anaphylaxis, bone pain, and osteoporosis. These symptoms can be severely debilitating, having a negative impact on quality of life. There remain no approved therapies for ISM or SSM. Thus, the discovery of new treatments targeting ISM or SSM would be useful.

Pyrrolotriazine compounds having mutant KIT and PDGFRα inhibitory activity have been reported in WO2015/057873. Specifically, certain compounds carrying an N-alkyl pyrazole are exemplified in WO2015/057873 and have mutant KIT and PDGFRα inhibitory activity, e.g., compound 63 with an N-ethyl pyrazole. The chemical structures of these N-alkyl pyrazole compounds exemplified in WO2015/057873 are different from those of the compounds of this disclosure.

Furthermore, although pyrrolotriazine compounds having mutant KIT and PDGFRα inhibitory activity are disclosed in WO2015/057873, the properties of these compounds are quite different from those of the compounds of the present disclosure.

An object of this disclosure is to provide novel compounds with highly selective, potent activity against mutant KIT and PDGFRα kinases for the safe and effective treatment of chronic disorders, such as ISM and SSM, as well as other diseases mediated by mutant KIT or PDGFRA. In treating these disorders, especially chronic disorders such as ISM and SSM, any new therapy should be well-tolerated. In particular, there is a need for new compounds targeting mutant KIT and PDGFRα kinases that have reduced levels of undesirable CNS side-effects which are associated with other known pyrrolotriazine compounds.

The present inventors have discovered novel compounds having high selectivity and potency against mutant KIT and PDGFRα kinases which, at the same time, possess additional desirable properties, such as, e.g., little or no penetration into the CNS, low unbound concentrations in the brain and high levels or active transport out of the brain, i.e., high efflux ratios from the CNS. In view of this desirable balance of properties, the compounds of the present disclosure are particularly suitable for treatment in the periphery, especially chronic treatment in the periphery, while side-effects in the CNS are reduced or minimized.

Thus, the compounds of the present disclosure aim to provide treatments having desirable efficacy, safety, and pharmaceutical properties for the treatment of KIT- and PDGFRA-mediated diseases. More specifically, the compounds of the disclosure exhibit a constellation of beneficial properties including a reduced level of brain penetration, while maintaining efficacy and other desirable pharmaceutical properties relative to known pyrrolotriazine compounds having mutant KIT and PDGFRα inhibitory activity.

ABBREVIATIONS AND DEFINITIONS

The following abbreviations and terms have the indicated means throughout:

The term "KIT" refers to a human tyrosine kinase that may be referred to as mast/stem cell growth factor receptor (SCFR), proto-oncogene c-KIT, tyrosine-protein kinase Kit, or CD117. As used herein, the term "KIT nucleotide"

encompasses the KIT gene, KIT mRNA, KIT cDNA, and amplification products, mutations, variations, and fragments thereof. "KIT gene" is used to refer to the gene that encodes a polypeptide with KIT kinase activity, e.g., the sequence of which is located between nucleotides 55,524,085 and 55,606,881 of chromosome 4 of reference human genome hg19. "KIT transcript" refers to the transcription product of the KIT gene, one example of which has the sequence of NCBI reference sequence NM_000222.2. The term "KIT protein" refers to the polypeptide sequence that is produced by the translation of the KIT nucleotide or a portion thereof.

The term "PDGFRA" refers to a human tyrosine kinase that may be referred to as platelet derived growth factor alpha. As used herein, the term "PDGFRA nucleotide" encompasses the PDGFRA gene, PDGFRA mRNA, KIT cDNA, and amplification products, mutations, variations, and fragments thereof "PDGFRA gene" is used to refer to the gene that encodes a polypeptide with PDGFRA kinase activity, e.g., the sequence of which is located between nucleotides 54,229,089 and 54,298,247 of chromosome 4 of reference *Homo sapiens* Annotation Release 109, GRCh38.p12. "PDGFRA transcript" refers to the transcription product of the PDGFRA gene, one example of which has the sequence of NCBI reference sequence NM_006206.6. The term "PDGFRA protein" or "PDGFRα" refers to the polypeptide sequence that is produced by the translation of the PDGFRA nucleotide or a portion thereof.

As used herein, a "malignant disease" refers to a disease in which abnormal cells divide without control and can invade nearby tissues. Malignant cells can also spread to other parts of the body through the blood or lymph system. Non-limiting examples of malignant diseases are carcinoma, sarcoma, leukemia, and lymphoma. Cancer is a non-limiting example of a malignant disease. In some embodiments, systemic mastocytosis is a non-limiting example of a malignant disease.

Non-limiting examples of cancer include gastrointestinal stomal tumor (GIST), AML (acute myeloid leukemia), melanoma, seminoma, intercranial germ cell tumors, and mediastinal B-cell lymphoma.

As used herein, an "eosinophilic disorder" refers to a disorder where eosinophils are found in an above-normal amount in various parts of the body and/or when there is a higher than normal ratio of hypodense versus normodense esosinophils (e.g., greater than 30%). The eosinophilic disorder described herein are characterized by an overabundance of eosinophils (eosinophilia). The increased number of eosinophils inflame tissues and cause organ damage. The heart, lungs, skin, and nervous system are most often affected, but any organ can be damaged.

Eosinophilic disorders are diagnosed according to the location where the levels of eosinophils are elevated:
Eosinophilic pneumonia (lungs)
Eosinophilic cardiomyopathy (heart)
Eosinophilic esophagitis (esophagus—EoE)
Eosinophilic gastritis (stomach—EG)
Eosinophilic gastroenteritis (stomach and small intestine—EGE)
Eosinophilic enteritis (small intestine)
Eosinophilic colitis (large intestine—EC)
Hypereosinophilic syndrome (blood and any organ—HES)

As used herein, the term "subject" or "patient" refers to organisms to be treated by the methods of the present disclosure. Such organisms include, but are not limited to, mammals (e.g., murines, simians, equines, bovines, porcines, canines, felines, and the like), and in some embodiments, humans.

As used herein, the phrase "therapeutically effective amount" refers to the amount of an active agent sufficient to effect beneficial or desired results. A therapeutically effective amount can be administered in one or more administrations, applications, or dosages and is not intended to be limited to a specific formulation or administration route.

As used herein, the phrase "weight equivalent of a pharmaceutically acceptable salt thereof" in reference to a specific compound includes the weight of both the compound and the associated salt.

As used herein, the phrase "pharmaceutically acceptable salt thereof," if used in relation to an active agent distributed as a salt form, refers to any pharmaceutically acceptable salt form of the active agent.

As used herein, the term "treating" includes any effect, e.g., lessening, reducing, modulating, ameliorating, or eliminating, that results in the improvement of the condition, disease, disorder, and the like, or ameliorating a symptom thereof.

While it is possible for an active agent to be administered alone, in some embodiments, the active agent can be administered as a pharmaceutical formulation, wherein the active agent is combined with one or more pharmaceutically acceptable excipients or carriers. For example, the active agent may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. For example, $C_1$ alkyl is methyl.

As used herein, "halo" refers to a radical of any halogen, e.g., —F, —Cl, —Br, or —I.

As used herein, "haloalkyl" and "haloalkoxy" refer to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine. "Haloalkylene" refers to a divalent alkyl, e.g., —$CH_2$—, —$CH_2CH_2$—, and —$CH_2CH_2CH_2$—, in which one or more hydrogen atoms are replaced by halo, and includes alkyl moieties in which all hydrogens have been replaced by halo.

As used herein, "cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). Cycloalkyl groups can contain fused or spiro rings. Fused rings are rings that share a common carbon atom. Examples of cycloalkyl moieties include, but are not limited to, cyclopropyl, cyclobutyl, cyclopentyl, and cyclohexyl.

As used herein, "heterocyclyl" refers to a monovalent radical of a heterocyclic ring system. Examples of heterocyclyls include, but are not limited to, ring systems in which every ring is non-aromatic and at least one ring comprises a heteroatom, e.g., oxetanyl, tetrahydrofuranyl, and tetrahydropyranyl.

As used herein, the definition of each expression, e.g., alkyl, m, n, etc., when it occurs more than once in any structure, is intended to be independent of its definition elsewhere in the same structure.

Certain compounds of the disclosure may exist in particular geometric or stereoisomeric forms. The present disclosure contemplates all such compounds, including cis- and trans-isomers, R- and S-enantiomers, diastereomers, (D)-isomers, (L)-isomers, racemic mixtures thereof, and other mixtures thereof, as falling within the scope of the disclosure. Additional asymmetric carbon atoms may be present in a substituent, such as, e.g., an alkyl group. All such isomers, as well as mixtures thereof, are intended to be included in this disclosure.

If, for instance, a particular enantiomer of compound of the disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as, e.g., amino, or an acidic functional group, such as, e.g., carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words, such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as, e.g., deuterium ($^2H$), tritium ($^3H$), carbon-13 ($^{13}C$), or carbon-14 ($^{14}C$). All isotopic variations of the compounds disclosed herein, whether radioactive or not, are intended to be encompassed within the scope of the present disclosure. In addition, all tautomeric forms of the compounds described herein are intended to be within the scope of the disclosure.

The compounds disclosed herein can be useful in the form of a free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Berge et al. (1977) "Pharmaceutical Salts", J. Pharm. Sci. 66:1-19.)

Certain compounds disclosed herein can exist in unsolvated forms as well as solvated forms, including hydrated forms. As used herein, the term "hydrate" or "hydrated" refers to a compound formed by the union of water with the parent compound.

In general, the solvated forms are equivalent to unsolvated forms and are encompassed within the scope of the present disclosure. Certain compounds disclosed herein may exist in multiple crystalline or amorphous forms. In general, all physical forms are equivalent for the uses contemplated by the disclosure and are intended to be within the scope of the present disclosure.

The present disclosure provides compounds of Formula I and pharmaceutically acceptable salts thereof and/or solvates of any of the foregoing. Nonlimiting embodiments of the present disclosure include:

Embodiment 1

A compound of Formula I:

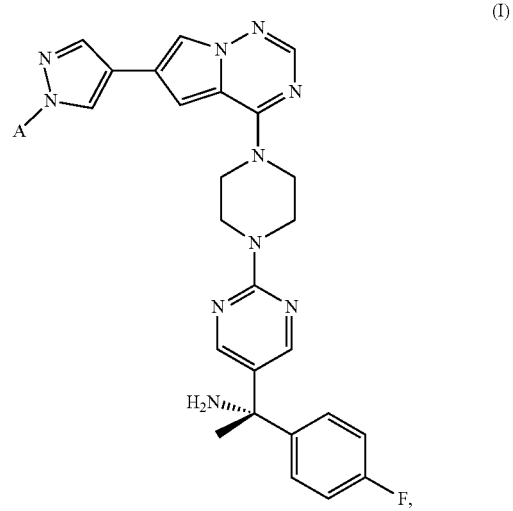

a pharmaceutically acceptable salt thereof, and/or a solvate of any of the foregoing, wherein:

A is

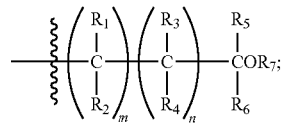

$R_1$ is chosen from hydrogen and methyl;
$R_2$ is chosen from hydrogen and methyl, or
$R_1$ and $R_2$ taken together form a cyclopropyl;
$R_3$ is chosen from hydrogen and methyl;
$R_4$ is chosen from hydrogen and methyl, or
$R_3$ and $R_4$ taken together form a cyclopropyl;
$R_5$ is chosen from hydrogen and methyl;
$R_6$ is chosen from hydrogen and methyl, or
$R_5$ and $R_6$ taken together form a cyclopropyl, or
one or $R_2$ or $R_4$ taken together with $R_6$ forms a cyclobutyl;

$R_7$ is hydrogen, or one of $R_2$, $R_4$, or $R_6$ taken together with $R_7$ forms a ring chosen from oxetane, tetrahydrofuran, and tetrahydropyran, wherein said tetrahydrofuran or tetrahydropyran is optionally substituted with hydroxyl;

m is 0 or 1; and n is 0 or 1.

In some embodiments of embodiment 1, when m is 0, $R_1$ and $R_2$ are absent. In some embodiments of embodiment 1, when n is 0, $R_3$ and $R_4$ are absent. In some embodiments of embodiment 1, m+n=1 or m and n cannot both be 0.

It is noted that in the present disclosure, when any two R groups (e.g., $R_1$ and $R_2$) taken together form a ring structure (e.g., a cyclopropyl), it is intended to include the intervening carbon atoms and/or the oxygen atom in the same ring structure.

Embodiment 2

The compound of embodiment 1, a pharmaceutically acceptable salt thereof, and/or a solvate of any of the foregoing, wherein:

A is:

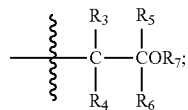

$R_3$ is chosen from hydrogen and methyl;

$R_4$ is chosen from hydrogen and methyl, or $R_3$ and $R_4$ taken together form a cyclopropyl;

$R_5$ is chosen from hydrogen and methyl; or $R_4$ and $R_6$ taken together form a cyclobutyl; or $R_5$ and $R_6$ taken together form a cyclopropyl; and $R_7$ is hydrogen.

Embodiment 3

The compound of embodiment 2, a pharmaceutically acceptable salt thereof, and/or a solvate of any of the foregoing, wherein:

A is:

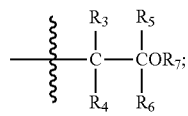

$R_3$ is chosen from hydrogen and methyl;

$R_4$ is chosen from hydrogen and methyl, or $R_3$ and $R_4$ taken together form a cyclopropyl;

$R_5$ is chosen from hydrogen and methyl; or $R_5$ and $R_6$ taken together form a cyclopropyl, and $R_7$ is hydrogen.

Embodiment 4

The compound of embodiment 1, a pharmaceutically acceptable salt thereof, and/or a solvate of any of the foregoing, wherein:

A is

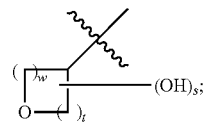

w is 1 or 2;

t is 1 or 2; and s is 0 or 1.

Embodiment 5

The compound of any one of embodiments 1-4, a pharmaceutically acceptable salt thereof, and/or a solvate of any of the foregoing, wherein the compound has a $K_p<0.39$.

In some embodiments of embodiment 5, the compound has a $K_p<0.39$ as measured according to the procedure described in Example 4. In some embodiments of embodiment 5, the compound, a pharmaceutically acceptable salt thereof, and/or a solvate of any of the foregoing is chosen from compounds 1, 2, 3, 4, 5, 6, 7, 9, 10, 11, 12, 13, 14, 17, 18, 19, 20, 21, and 22.

Embodiment 6

The compound of any one of embodiments 1-4, a pharmaceutically acceptable salt thereof, and/or a solvate of any of the foregoing, wherein the compound has a $K_p \leq 0.20$.

In some embodiments of embodiment 6, the compound has a $K_p \leq 0.20$ as measured according to the procedure described in Example 4. In some embodiments of embodiment 6, the compound, a pharmaceutically acceptable salt thereof, and/or a solvate of any of the foregoing is chosen from compounds 1, 3, 4, 5, 6, 9, 11, 13, 17, 18, 19, 20, 21, and 22.

Embodiment 7

The compound of any one of embodiments 1-6, a pharmaceutically acceptable salt thereof, and/or a solvate of any of the foregoing, wherein the compound has a $K_{p,uu} \leq 0.2$ in homogenate rat brain.

In some embodiments of embodiment 7, the compound has a $K_{p,uu} \leq 0.2$ in homogenate rat brain as measured according to the procedure described in Example 4. In some embodiments of embodiment 7, the compound, a pharmaceutically acceptable salt thereof, and/or a solvate of any of the foregoing is chosen from compounds 1, 2, 3, 4, 5, 6, 7, 8, 9, 10, 11, 12, 16, 17, 18, 19, 20, and 22.

Embodiment 8

The compound of any one of embodiments 1-7, a pharmaceutically acceptable salt thereof, and/or a solvate of any of the foregoing, wherein the compound has a $K_{p,uu}<0.1$ in homogenate rat brain.

In some embodiments of embodiment 8, the compound has a $K_{p,uu}<0.1$ in homogenate rat brain as measured according to the procedure described in Example 4. In some embodiments of embodiment 8, the compound, a pharmaceutically acceptable salt thereof, and/or a solvate of any of the foregoing is chosen from compounds 1, 2, 3, 4, 5, 6, 7, 9, 11, 12, 17, 18, 19, 20, and 22.

Embodiment 9

The compound of any one of embodiments 1-8, a pharmaceutically acceptable salt thereof, and/or a solvate of any of the foregoing, wherein the compound has a $K_{p,uu} \leq 0.05$ in homogenate rat brain.

In some embodiments of embodiment 9, the compound has a $K_{p,uu} \leq 0.05$ in homogenate rat brain as measured according to the procedure described in Example 4. In some embodiments of embodiment 9, the compound, a pharmaceutically acceptable salt thereof, and/or a solvate of any of the foregoing is chosen from compounds 1, 3, 4, 5, 6, 9, 17, 19, 20, and 22.

Embodiment 10

The compound of any one of embodiments 1-9, a pharmaceutically acceptable salt thereof, and/or a solvate of any of the foregoing, wherein the compound has a $K_{p,uu} \leq 0.1$ in rat brain slice.

In some embodiments of embodiment 10, the compound has a $K_{p,uu} \leq 0.1$ in rat brain slice as measured in according to the procedure described in Example 4. In some embodiments of embodiment 10, the compound, a pharmaceutically acceptable salt thereof, and/or a solvate of any of the foregoing is chosen from compounds 1, 2, 3, 4, 5, 6, 7, 8, 9, 10, 11, 12, 13, 14, 15, 16, 17, 18, 20, 21, and 22.

Embodiment 11

The compound of any one of embodiments 1-10, a pharmaceutically acceptable salt thereof, and/or a solvate of any of the foregoing, wherein the compound has a $K_{p,uu} \leq 0.05$ in rat brain slice.

In some embodiments of embodiment 11, the compound has a $K_{p,uu} \leq 0.05$ in rat brain slice as measured according to the procedure described in Example 4. In some embodiments of embodiment 11, the compound, a pharmaceutically acceptable salt thereof, and/or a solvate of any of the foregoing is chosen from compounds 1, 2, 3, 4, 5, 6, 7, 8, 9, 10, 11, 12, 13, 14, 17, 18, 20, and 22.

Embodiment 12

The compound of any one of embodiments 1-11, a pharmaceutically acceptable salt thereof, and/or a solvate of any of the foregoing, wherein the compound has an unbound clearance ($Cl_u$) in rat of <900 mL/min/kg.

In some embodiments of embodiment 12, the compound has a $Cl_u$ in rat of <900 mL/min/kg as measured according to the procedure described in Example 4. In some embodiments of embodiment 12, the compound, a pharmaceutically acceptable salt thereof, and/or a solvate of any of the foregoing is chosen from compounds 3, 4, 7, and 9.

Embodiment 13

The compound of any one of embodiments 1-12, a pharmaceutically acceptable salt thereof, and/or a solvate of any of the foregoing, wherein the compound has an unbound clearance ($Cl_u$) in rat of <750 mL/min/kg.

In some embodiments of embodiment 13, the compound has a $Cl_u$ in rat of <750 mL/min/kg as measured according to the procedure described in Example 4. In some embodiments of embodiment 13, the compound, a pharmaceutically acceptable salt thereof, and/or a solvate of any of the foregoing is chosen from compounds 4, 7, and 9.

Embodiment 14

The compound of any one of embodiments 1-12, a pharmaceutically acceptable salt thereof, and/or a solvate of any of the foregoing, wherein the compound has an $IC_{50}$ for CYP3A4 of <10 μM.

In some embodiments of embodiment 14, the compound has an $IC_{50}$ for CYP3A4 of <10 μM as measured according to the procedure described in Example 5. In some embodiments of embodiment 14, the compound, a pharmaceutically acceptable salt thereof, and/or a solvate of any of the foregoing is compound 4.

Embodiment 15

The compound of embodiment 1, a pharmaceutically acceptable salt thereof, and/or a solvate of any of the foregoing, wherein A is chosen from

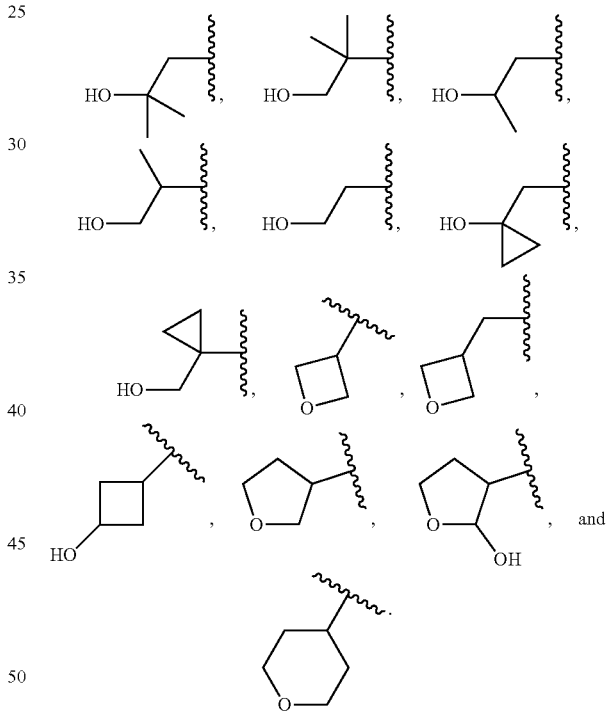

Embodiment 15-1

The compound of embodiment 1, a pharmaceutically acceptable salt thereof, and/or a solvate of any of the foregoing, wherein A is chosen from -continued

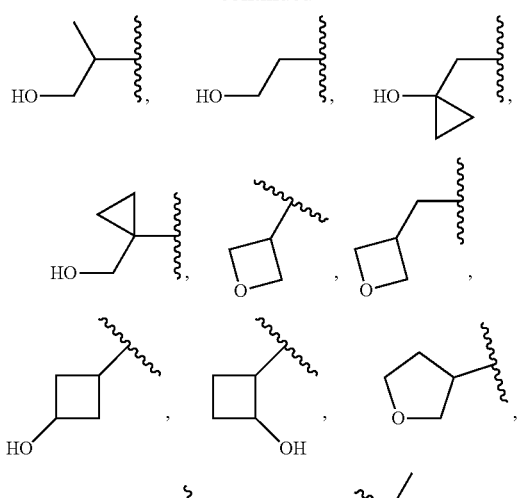

Embodiment 16

The compound of embodiment 1, a pharmaceutically acceptable salt thereof, and/or a solvate of any of the foregoing, wherein A is chosen from

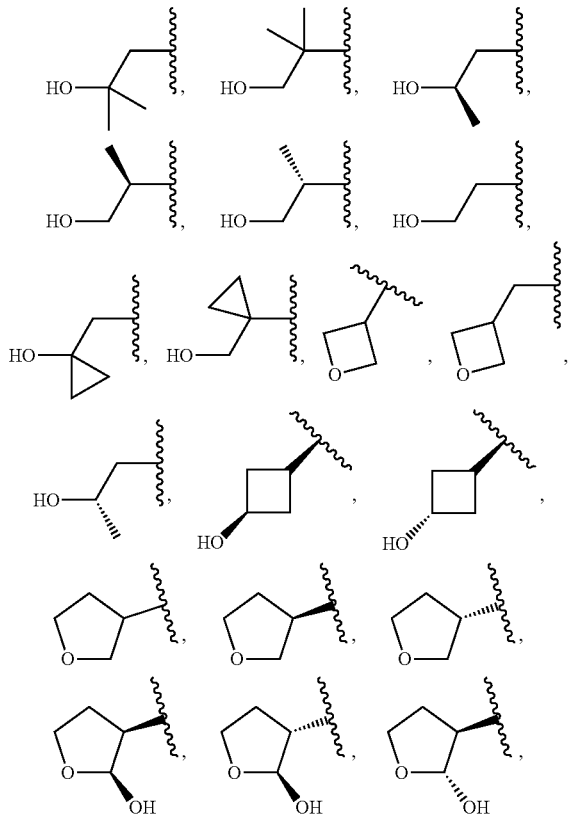

-continued

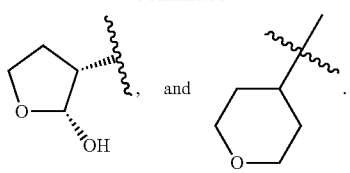

Embodiment 16-1

The compound of embodiment 1, a pharmaceutically acceptable salt thereof, and/or a solvate of any of the foregoing, wherein A is chosen from

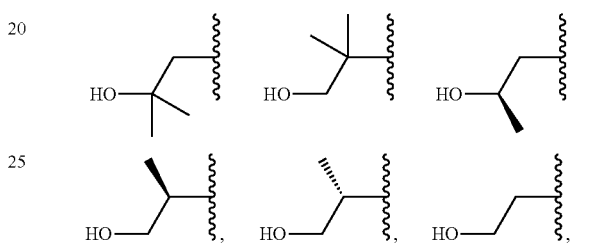

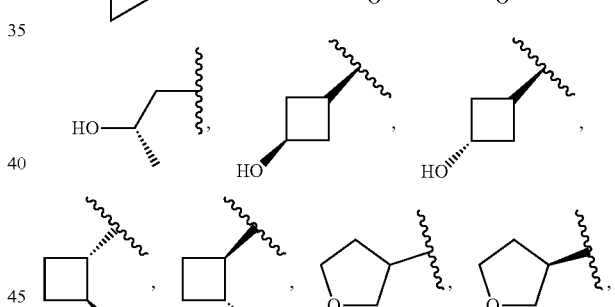

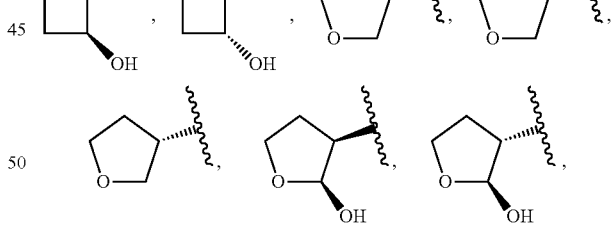

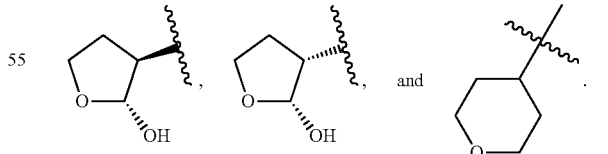

Embodiment 17

The compound of any one of embodiments 1-3, a pharmaceutically acceptable salt thereof, and/or a solvate of any of the foregoing, wherein A is chosen from

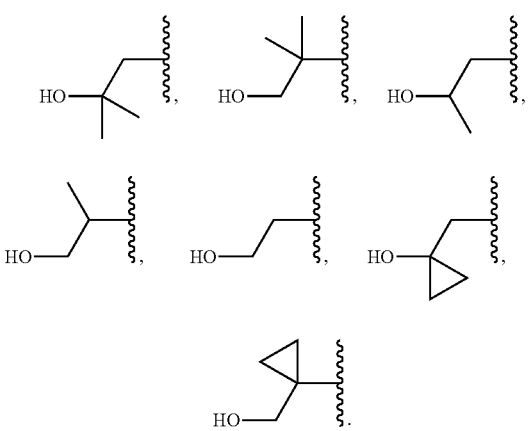

Embodiment 18

The compound of any one of embodiments 1-3 or 5, a pharmaceutically acceptable salt thereof, and/or a solvate of any of the foregoing, wherein A is chosen from

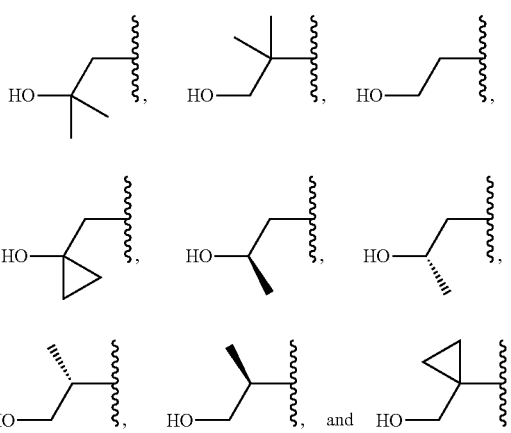

Embodiment 19

The compound of any one of embodiments 1-3 or 5-6, a pharmaceutically acceptable salt thereof, and/or a solvate of any of the foregoing, wherein A is chosen from

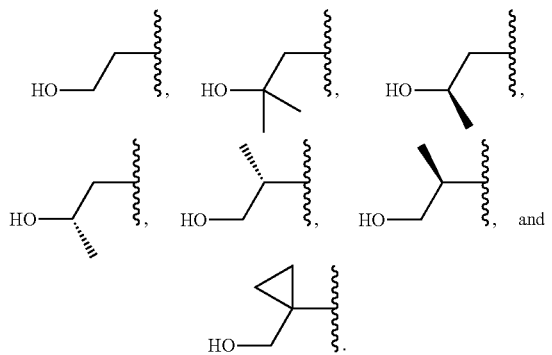

Embodiment 20

The compound of any one of embodiments 1-3 or 5-7, pharmaceutically acceptable salt thereof, and/or a solvate of any of the foregoing, wherein A is chosen from

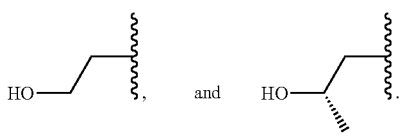

Embodiment 21

The compound of any one of embodiments 1-13, a pharmaceutically acceptable salt thereof, and/or a solvate of any of the foregoing, wherein the compound is chosen from 4, 7, and 9.

Embodiment 22

The compound of anyone of embodiments 1-13, a pharmaceutically acceptable salt thereof, and/or a solvate of any of the foregoing, wherein the compound is chosen from 4 and 9.

Embodiment 23

The compound of any one of embodiments 1-13, a pharmaceutically acceptable salt thereof, and/or a solvate of any of the foregoing, wherein the compound is

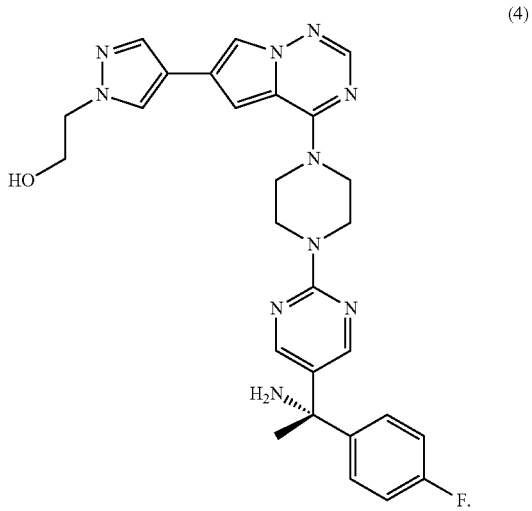 [SMILES: C[C@](N)(c1ccc(F)cc1)c1cnc(N2CCN(c3ncnn4cc(-c5cnn(CCO)c5)cc34)CC2)nc1]

(4)

Embodiment 24

The compound of any one of embodiments 1-13, a pharmaceutically acceptable salt thereof, and/or a solvate of any of the foregoing, wherein the compound is

15

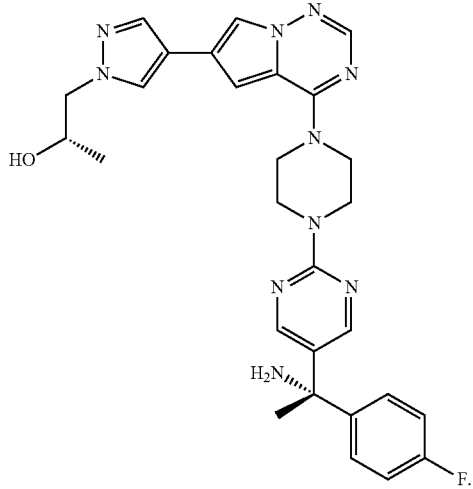

(9)

Embodiment 25

The compound of any one of embodiments 1-13, a pharmaceutically acceptable salt thereof, and/or a solvate of any of the foregoing, wherein the compound is

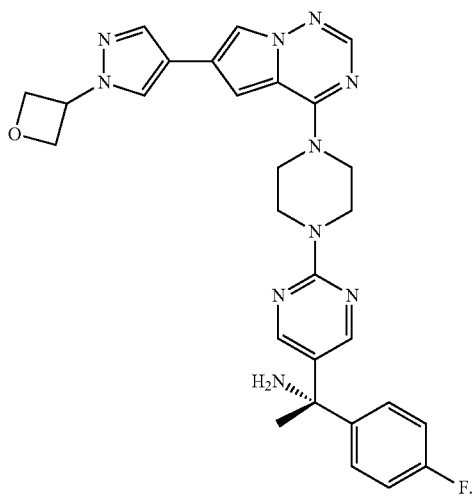

(7)

Embodiment 26

A pharmaceutical composition comprising:
a compound of any one of embodiments 1-25, a pharmaceutically acceptable salt thereof, and/or a solvate of any of the foregoing; and
a pharmaceutically acceptable excipient.

Embodiment 27

A method of treating a disease or condition in a patient in need thereof, wherein the method comprises administering to the patient a compound according to any one of embodiments 1-25, a pharmaceutically acceptable salt thereof, and/or a solvate of any of the foregoing, wherein the disease or condition is chosen from systemic mastocytosis, gastrointestinal stromal tumors, acute myeloid leukemia, melanoma, seminoma, intercranial germ cell tumors, mediastinal B-cell lymphoma, Ewing's sarcoma, diffuse large B cell lymphoma, dysgerminoma, myelodysplastic syndrome, nasal NK/T-cell lymphoma, chronic myelomonocytic leukemia, and brain cancer.

Embodiment 28

A method of treating a disease or condition mediated by mutant KIT or PDGFRα in a patient in need thereof, wherein the method comprises administering to the patient a compound according to any one of embodiments 1-25, a pharmaceutically acceptable salt thereof, and/or a solvate of any of the foregoing.

Embodiment 29

The method of embodiment 28, wherein the disease or condition is chosen from systemic mastocytosis, gastrointestinal stromal tumors, acute myeloid leukemia, melanoma, seminoma, intercranial germ cell tumors, mediastinal B-cell lymphoma, Ewing's sarcoma, diffuse large B cell lymphoma, dysgerminoma, myelodysplastic syndrome, nasal NK/T-cell lymphoma, chronic myelomonocytic leukemia, and brain cancer.

Embodiment 30

A compound according to any one of embodiments 1-25, a pharmaceutically acceptable salt thereof, and/or a solvate of any of the foregoing for use as a medicament for treating a disease or condition in a patient in need thereof, wherein the disease or condition is chosen from systemic mastocytosis, gastrointestinal stromal tumors, acute myeloid leukemia, melanoma, seminoma, intercranial germ cell tumors, mediastinal B-cell lymphoma, Ewing's sarcoma, diffuse large B cell lymphoma, dysgerminoma, myelodysplastic syndrome, nasal NK/T-cell lymphoma, chronic myelomonocytic leukemia, and brain cancer.

Embodiment 31

A compound according to any one of embodiments 1-25, a pharmaceutically acceptable salt thereof, and/or a solvate of any of the foregoing for use as a medicament for treating a disease or condition mediated by mutant KIT or PDGFRA in a patient in need thereof.

Embodiment 32

The compound of embodiment 31, wherein the disease or condition is chosen from systemic mastocytosis, gastrointestinal stromal tumors, acute myeloid leukemia, melanoma, seminoma, intercranial germ cell tumors, mediastinal B-cell lymphoma, Ewing's sarcoma, diffuse large B cell lymphoma, dysgerminoma, myelodysplastic syndrome, nasal NK/T-cell lymphoma, chronic myelomonocytic leukemia, and brain cancer.

Embodiment 33

A method of treating an eosinophilic disorder, comprising administering to a subject in need thereof a therapeutically effective amount of a compound according to any one of embodiments 1-25, a pharmaceutically acceptable salt thereof, and/or a solvate of any of the foregoing.

Embodiment 34

The method of embodiment 33, wherein the eosinophilic disorder is selected from hypereosinophilic syndrome, eosinophilia, eosinophilic enterogastritis, eosinophilic leukemia, eosinophilic granuloma and Kimura's disease.

Embodiment 35

The method of embodiment 33, wherein the eosinophilic disorder is hypereosinophilic syndrome.

Embodiment 36

The method of embodiment 33, wherein the eosinophilic disorder is eosinophilic leukemia.

Embodiment 37

The method of embodiment 36, wherein the eosinophilic leukemia is chronic eosinophilic leukemia.

Embodiment 38

The method of any one of embodiments 33-37, wherein the eosinophilic disorder is refractory to treatment with imatinib, sunitinib, and/or regorafenib.

Embodiment 39

A compound according to any one of embodiments 1-25, a pharmaceutically acceptable salt thereof, and/or a solvate of any of the foregoing for use as a medicament for treating an eosinophilic disorder.

Embodiment 40

The compound of embodiment 39, wherein the eosinophilic disorder is selected from hypereosinophilic syndrome, eosinophilia, eosinophilic enterogastritis, eosinophilic leukemia, eosinophilic granuloma and Kimura's disease.

Embodiment 41

The compound of embodiment 39, wherein the eosinophilic disorder is hypereosinophilic syndrome.

Embodiment 42

The compound of embodiment 39, wherein the eosinophilic disorder is eosinophilic leukemia.

Embodiment 43

The compound of embodiment 42, wherein the eosinophilic leukemia is chronic eosinophilic leukemia.

Embodiment 44

The method of any one of embodiments 39-43, wherein the eosinophilic disorder is refractory to treatment with imatinib, sunitinib, and/or regorafenib.

Embodiment 45

A method of treating a mast cell disorder, comprising administering to a subject in need thereof a therapeutically effective amount of a compound according to any one of embodiments 1-25, a pharmaceutically acceptable salt thereof, and/or solvate of any of the foregoing.

Embodiment 46

The method of embodiment 45, wherein the mast cell disorder is mediated by mutant KIT or PDGFRα.

Embodiment 46-1

The method of embodiment 45, wherein the mast cell disorder is mediated by wild type KIT or PDGFRα.

Embodiment 47

The method of any one of embodiments 46, wherein the mast cell disorder is selected from mast cell activation syndrome (MCAS) and hereditary alpha tryptasemia (HAT).

Embodiment 48

The method of embodiment 47, wherein the MCAS is selected from monoclonal mast cell activation syndrome (MMAS), secondary MCAS, and idiopathic MCAS.

Embodiment 48-1

The method of embodiment 27, wherein the disease or condition is systemic mastocytosis.

Embodiment 49

The method of any one of embodiments 48, wherein the systemic mastocytosis is chosen from indolent systemic mastocytosis and smoldering systemic mastocytosis.

TABLE 1 lists the compounds prepared by the synthetic methods described herein.

| No. | Chemical Structure |
|---|---|
| 1 | 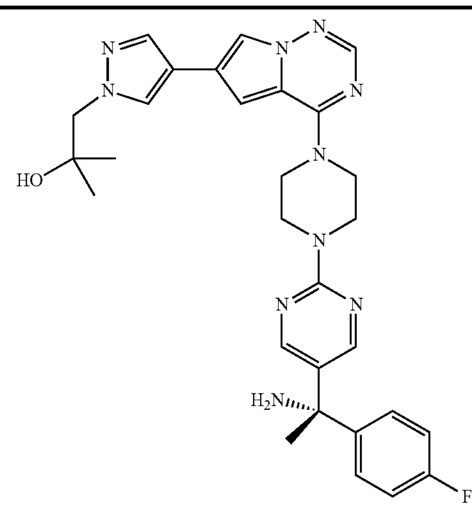 |

TABLE 1-continued
lists the compounds prepared by the synthetic methods described herein.
| No. | Chemical Structure |
|---|---|
| 2 | 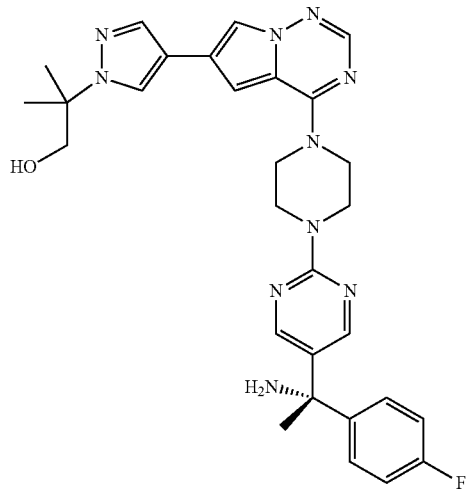 |
| 3 | 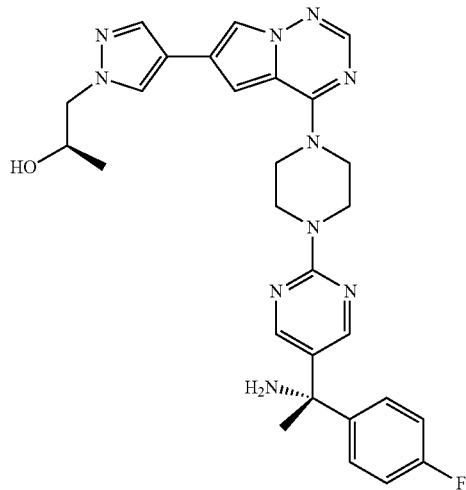 |
| 4 | 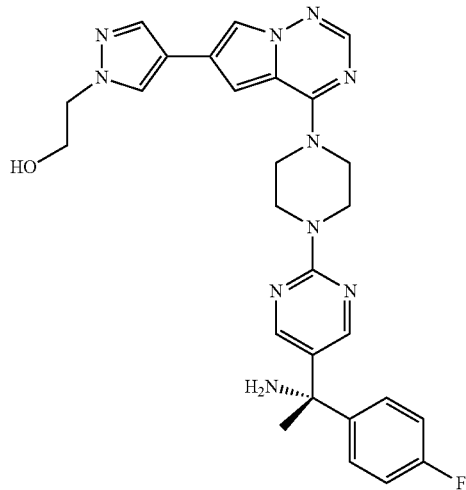 |
| 5 | 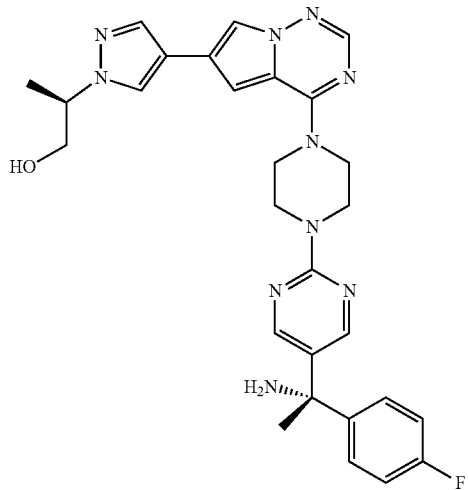 |
| 6 | 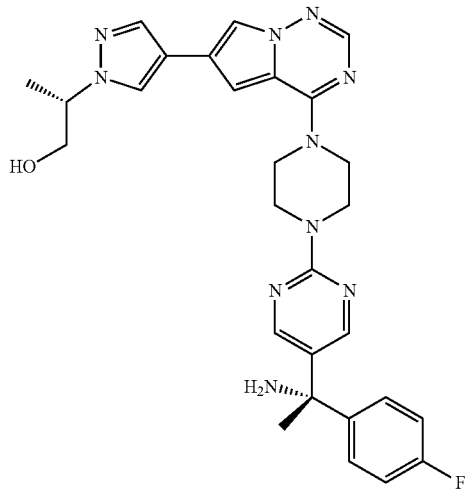 |
| 7 | 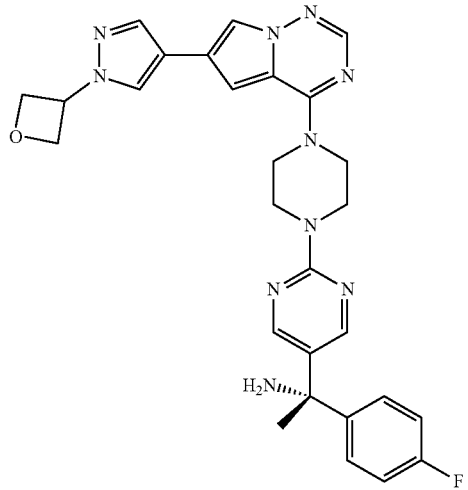 |

TABLE 1-continued
lists the compounds prepared by the synthetic methods described herein.
| No. | Chemical Structure |
|-----|-------------------|
| 8 | 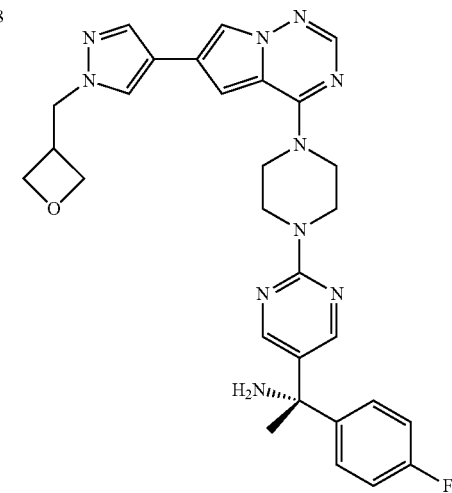 |
| 9 | 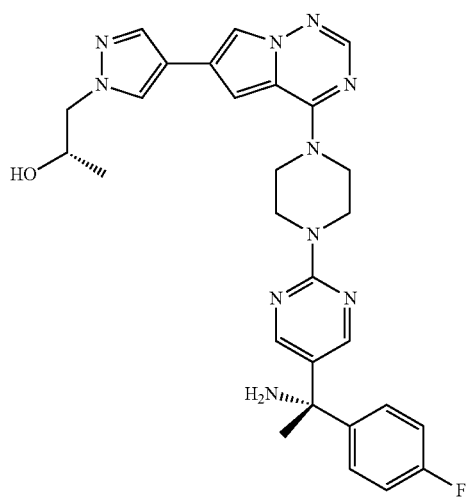 [SMILES: C[C@H](O)Cn1cc(-c2cc3c(N4CCN(c5ncc([C@@](C)(N)c6ccc(F)cc6)cn5)CC4)ncnn3c2)cn1] |
| 10 | 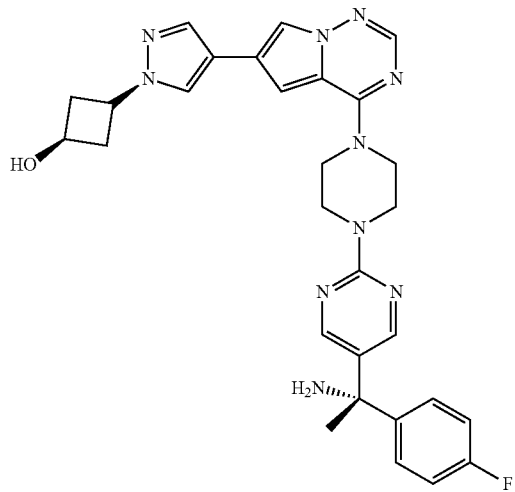 |
TABLE 1-continued
lists the compounds prepared by the synthetic methods described herein.
| No. | Chemical Structure |
|-----|-------------------|
| 11 | 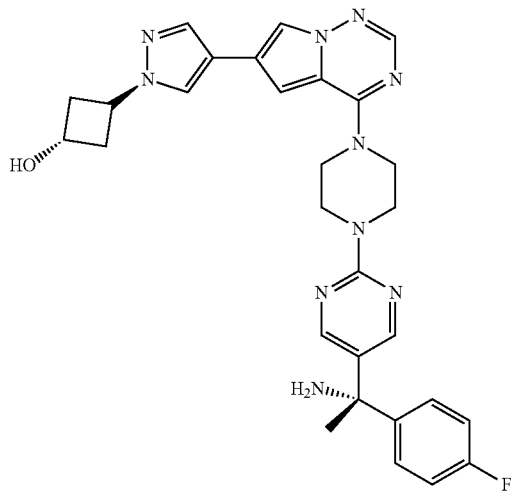 |
| 12 | 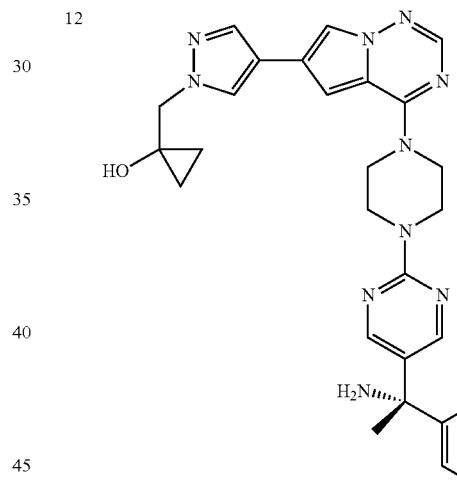 |
| 13 | 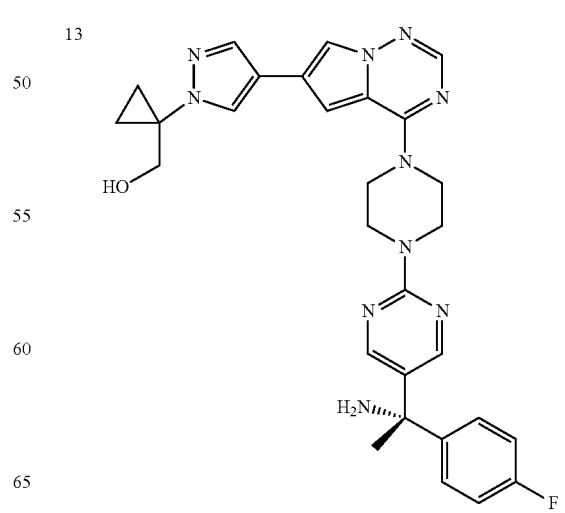 |

TABLE 1-continued
lists the compounds prepared by the synthetic methods described herein.
| No. | Chemical Structure |
|---|---|
| 14 | 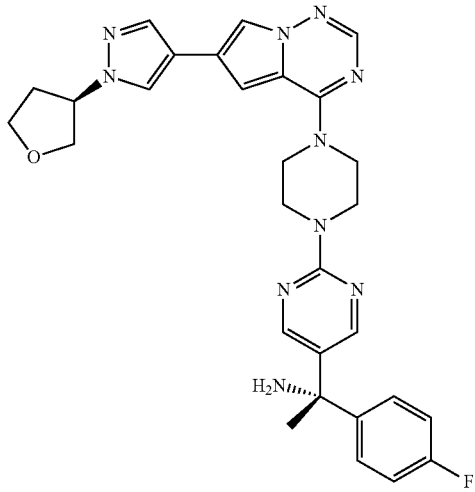 [SMILES: C[C@](N)(c1ccc(F)cc1)c1cnc(N2CCN(c3ncnn4cc(-c5cnn([C@@H]6CCOC6)c5)cc34)CC2)nc1] |
| 15 | 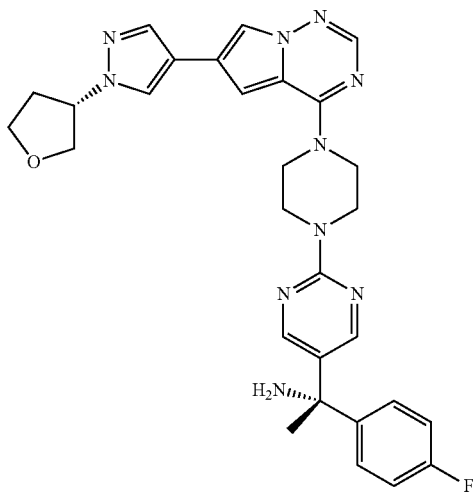 [SMILES: C[C@](N)(c1ccc(F)cc1)c1cnc(N2CCN(c3ncnn4cc(-c5cnn([C@H]6CCOC6)c5)cc34)CC2)nc1] |
| 16 | 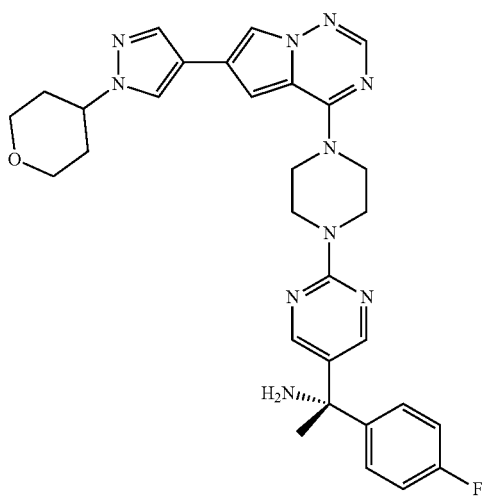 [SMILES: C[C@](N)(c1ccc(F)cc1)c1cnc(N2CCN(c3ncnn4cc(-c5cnn(C6CCOCC6)c5)cc34)CC2)nc1] |
| 17 | 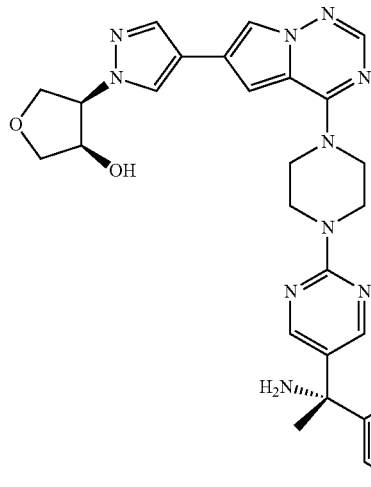 |
| 18 | 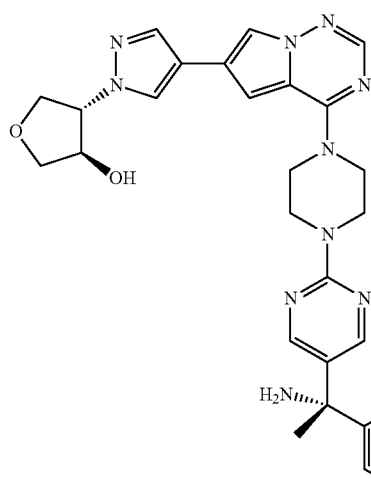 |
| 19 | 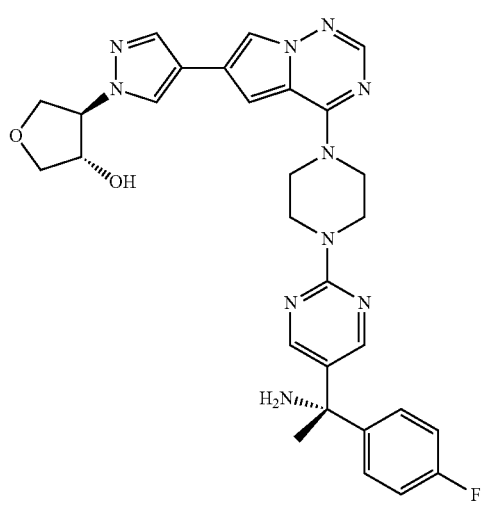 [SMILES: C[C@](N)(c1ccc(F)cc1)c1cnc(N2CCN(c3ncnn4cc(-c5cnn([C@@H]6COC[C@H]6O)c5)cc34)CC2)nc1] |

TABLE 1-continued lists the compounds prepared by the synthetic methods described herein.

No. Chemical Structure

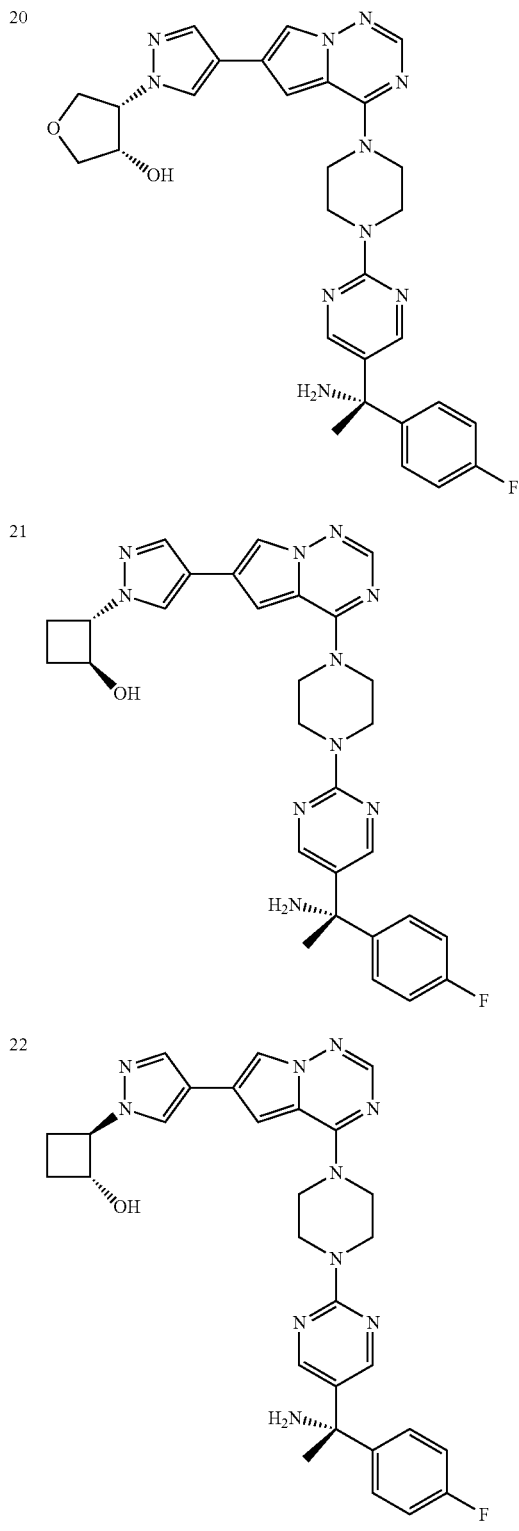

20

21

22

Compounds of the disclosure are selective KIT inhibitors. In some embodiments, compounds of the disclosure are selective D816V KIT inhibitors. Compounds of the disclosure are selective PDGFRα inhibitors. In some embodiments, compounds of the disclosure are selective PDGFRα exon 18 inhibitors. In some embodiments, compounds of the disclosure are selective PDGFRα D842V inhibitors. As used herein, a "selective KIT inhibitor" or a "selective PDGFRα inhibitor" refers to a compound or a pharmaceutically acceptable salt thereof or a solvate of any of the foregoing that selectively inhibits a KIT protein kinase or PDGFRα protein kinase over another protein kinase and exhibits at least a 2-fold selectivity for a KIT protein kinase or a PDGFRα protein kinase over another kinase. For example, a selective KIT inhibitor or a selective PDGFRA inhibitor exhibits at least a 9-fold selectivity, 10-fold selectivity; at least a 15-fold selectivity; at least a 20-fold selectivity; at least a 30-fold selectivity; at least a 40-fold selectivity; at least a 50-fold selectivity; at least a 60-fold selectivity; at least a 70-fold selectivity; at least a 80-fold selectivity; at least a 90-fold selectivity; at least 100-fold, at least 125-fold, at least 150-fold, at least 175-fold, or at least 200-fold selectivity for a KIT protein kinase or a PDGFRα kinase over another kinase. In some embodiments, a selective KIT inhibitor or a selective PDGFRα inhibitor exhibits at least 150-fold selectivity over another kinase, e.g., VEGFR2 (vascular endothelial growth factor receptor 2), SRC (Non-receptor protein tyrosine kinase), and FLT3 (Fms-Like Tyrosine kinase 3). In some embodiments, a selective KIT or a selective PDGFRα inhibitor exhibits selectivity over PDGRFβ, CSF1R (colony stimulating factor receptor 1), and FLT3. In some embodiments, a selective KIT or a selective PDGFRα inhibitor exhibits selective over LCK (lymphocyte-specific protein kinase), ABL (nuclear protein tyrosine kinase), never-in-mitosis gene A (NIMA)-related kinase 5 (NEK5), and ROCK1 (rho-associated coil-coil-continuing protein kinase-1). In some embodiments, selectivity for a KIT protein kinase or a PDGFRα protein kinase over another kinase is measured in a cellular assay (e.g., a cellular assay). In some embodiments, selectivity for a KIT protein kinase or a PDGFRα protein kinase over another kinase is measured in a biochemical assay (e.g., a biochemical assay).

Compounds of the disclosure are selective over ion channels. In some embodiments, a selective KIT or a selective PDGFRα inhibitor has limited potential to inhibit human voltage-gated sodium channel (hNav 1.2).

Compounds of the disclosure are selective for mutant KIT over wild type KIT. In some embodiments, compounds of the disclosure are selective for exon 17 mutant KIT over wild type KIT.

Compounds of the disclosure can be useful for treating diseases or conditions associated with mutant KIT or mutant PDGFRA activity in humans or non-humans. In some embodiments, compounds of the disclosure are for use as a medicament. In some embodiments, compounds of the disclosure are for use in therapy. In some embodiments, compounds of the disclosure are for use in the manufacture of a medicament. In some embodiments, the disclosure provides methods for treating KIT-driven malignancies, include mastocytosis (SM), GIST (gastrointestinal stromal tumors), AML (acute myeloid leukemia), melanoma, seminoma, intercranial germ cell tumors, and/or mediastinal B-cell lymphoma. In addition, mutations in KIT have been linked to Ewing's sarcoma, DLBCL (diffuse large B cell lymphoma), dysgerminoma, MDS (myelodysplastic syndrome), NKTCL (nasal NK/T-cell lymphoma), CMML (chronic myelomonocytic leukemia), and brain cancers. In some embodiments, the disclosure provides methods for treating Ewing's sarcoma, DLBCL, dysgerminoma, MDS, NKTCL, CMML, and/or brain cancers. KIT mutations have also been found in thyroid cancer, colorectal cancer, endometrial cancer, bladder cancer, NSCLC, and breast cancer (AACR Project GENIE). In some embodiments, compounds of the disclosure can be useful for treating mast cell activation syndrome (MCAS). Compounds of the disclosure can be useful for treating systemic mastocytosis. Compounds of the disclosure can be useful for treating advanced systemic mastocytosis. Compounds of the disclosure can be useful for treating indolent SM and smoldering SM. Compounds of the disclosure can be useful for treating GIST.

Compounds of the disclosure can be useful for treating diseases or conditions associated with the KIT mutations in Exon 9, Exon 11, Exon 14, Exon 17, and/or Exon 18 of the KIT gene sequence. Compounds of the disclosure can be useful for treating diseases or conditions associated with PDGFRA mutations in Exon 12, Exon 14, and/or Exon 18 of the PDGFRA gene sequence. In some embodiments, provided herein are methods for treating a disease or condition associated with at least one KIT mutation in Exon 9, Exon 11, Exon 14, Exon 17, and/or Exon 18 of the KIT gene sequence. In some embodiments, methods for treating a disease or condition associated with at least one PDGFRA mutation in Exon 12, Exon 14, and/or Exon 18 of the PDGFRA gene sequence are provided.

Compounds of the disclosure can be active against one or more KIT protein kinases with mutations in Exon 17 of the KIT gene sequence (e.g., KIT protein mutations D816V, D816Y, D816F, D816K, D816H, D816A, D816G, D816E, D816I, D816F, D820A, D820E, D820G, D820Y, N822K, N822H, V560G, Y823D, and A829P), and much less active against wild-type KIT protein kinase. In some embodiments, provided herein are methods for treating a disease or condition associated with at least one KIT mutation such as those chosen from D816V, D816Y, D816F, D816K, D816H, D816A, D816G, D816E, D816I, D816F, D820A, D820E, D820G, D820Y, N822K, N822H, V560G, Y823D, and A829P. In some embodiments, provided herein are methods for treating a disease or condition associated with at least one KIT mutation such as, e.g., those chosen from C809, C809G, D816H, D820A, D820G, N822H, N822K, and Y823D.

Compounds of the disclosure can be active against one or more KIT protein kinases with mutations in Exon 11 of the KIT gene sequence (e.g., KIT protein mutations del557-559insF, V559G/D). In some embodiments, provided herein are methods for treating a disease or condition associated with at least one KIT mutation, such as, e.g., those chosen from L576P, V559D, V560D, V560G, W557G, Del 554-558EVQWK (SEQ ID NO: 1), del557-559insF, Del EVQWK (SEQ ID NO: 1) 554-558, Del EVQWKVVEEINGNNYVYI (SEQ ID NO: 2) 554-571, Del KPMYEVQWK (SEQ ID NO: 3) 550-558, Del KPMYEVQW (SEQ ID NO: 4) 550-557FL, Del KV558-559, Del KV558-559N, Del MYEVQW (SEQ ID NO: 5) 552-557, Del PMYE (SEQ ID NO: 6) 551-554, Del VV559-560, Del WKVVE (SEQ ID NO: 7) 557-561, Del WK557-558, Del WKVV (SEQ ID NO: 8) 557-560C, Del WKVV (SEQ ID NO: 8) 557-560F, Del YEVQWK (SEQ ID NO: 9) 553-558, and insertion K558NP.

Compounds of the disclosure can be active against one or more KIT protein kinases with mutations in Exon 11/13 of the KIT gene sequence (e.g., KIT protein mutations V559D/V654A, V560G/D816V, and V560G/822K). In some embodiments, provided here are methods for treating a disease or condition associated with one or more KIT mutations in Exon 11/13).

Compounds of the disclosure can be active against one or more KIT protein kinases with mutations in Exon 9 of the KIT gene sequence. In some embodiments, provided herein are methods for treating a disease or condition associated with at least one KIT mutation in Exon 9.

In some embodiments, compounds of the disclosure are not active against KIT protein kinases with the mutations V654A, N655T, T670I, and/or N680.

Compounds of the disclosure can be active against one or more PDGFRα protein kinases with mutations. In some embodiments, provided herein are methods for treating a disease or condition associated with at least one PDGFRA mutation in Exon 12 of the PDGFRA gene sequence, such as, e.g., PDGFRα protein mutations V561D, Del RV560-561, Del RVIES (SEQ ID NO: 10) 560-564, Ins ER561-562, SPDGHE (SEQ ID NO: 11) 566-571R, SPDGHE (SEQ ID NO: 11) 566-571K, or Ins YDSRW (SEQ ID NO: 12) 582-586. In some embodiments, provided herein are methods for treating a disease or condition associated with at least one PDGFRA mutation in Exon 14 of the PDGFRA gene sequence, such as, e.g., PDGFRα protein mutation N659K. In some embodiments, provided herein are methods for treating a disease or condition associated with at least one PDGFRA mutation in Exon 18 of the PDGFRA gene sequence, such as, e.g., PDGFRα protein mutations D842V, D842Y, D842I, D1842-843IM, D846Y, Y849C, Del D842, Del 1843, Del RD841-842, Del DIM842-845, Del DIMH (SEQ ID NO: 13) 842-845, Del IMHD (SEQ ID NO: 14) 843-846, Del MHDS (SEQ ID NO: 15) 844-847, RD841-842KI, DIMH (SEQ ID NO: 13) 842-845A, DIMH (SEQ ID NO: 13) 842-845V, DIMHD (SEQ ID NO: 16) 842-846E, DIMHD (SEQ ID NO: 16) 842-846S, DIMHD (SEQ ID NO: 16) 842-846N, DIMHD (SEQ ID NO: 16) 842-846G, IMHDS (SEQ ID NO: 17) 843-847T, IMHDS (SEQ ID NO: 17) 843-847M, or HDSN (SEQ ID NO: 18) 845-848P.

Compounds of the disclosure can be active against one or more PDGFRα protein kinases with mutations Exon 18 in the PDGFRA gene sequence (e.g., protein mutations PDGFRα D842V, PDGFRα D842I, or PDGFRα D842Y). In some embodiments, provided herein are methods for treating a disease or condition associated with at least one PDGFRA mutation in Exon 18, such as, e.g., protein mutation PDGFRα D842V.

Compounds of the disclosure can be useful for treating an eosinophilic disorder. In some embodiments, the eosinophilic disorder is mediated by mutant KIT or PDGFRα. In some embodiments, that eosinophilic disorder is mediated by wild type KIT or PDGFRα. In some embodiments, provided herein are methods for treating an eosinophilic disorder, comprising administering to a subject a therapeutically effective amount of the compounds of the disclosure or a pharmaceutically acceptable salt thereof and/or solvate of any of the foregoing. In one embodiment, the eosinophilic disorder is selected from hypereosinophilic syndrome, eosinophilia, eosinophilic enterogastritis, eosinophilic leukemia, eosinophilic granuloma and Kimura's disease.

In some embodiments, eosinophilic disorder is selected from hypereosinophilic syndrome, eosinophilia, eosinophilic enterogastritis, eosinophilic leukemia, eosinophilic granuloma and Kimura's disease. Other eosinophilic disorders include eosinophilic esophagitis, eosinophilic gastroenteritis, eosinophilic fasciitis, and Churg-Strauss syndrome.

In one embodiment, the eosinophilic disorder is hypereosinophilic syndrome. In a specific embodiment, the hypereosinophilic syndrome is idiopathic hypereosinophilic syndrome. In one embodiment, the eosinophilic disorder is eosinophilic leukemia. In a specific embodiment, the eosinophilic leukemia is chronic eosinophilic leukemia. In another embodiment, the eosinophilic disorder is refractory to treatment with imatinib, sunitinib, and/or regorafenib. In a specific embodiment, the eosinophilic disorder is refractory to treatment with imatinib.

Compounds of the disclosure can be useful for reducing the number of eosinophils in a subject in need thereof. In some embodiments, provided herein are methods for reducing the number of eosinophils in a subject in need thereof comprising administering to the subject a therapeutically effective amount of a compound of the disclosure or a pharmaceutically acceptable salt thereof and/or a solvate of any of the foregoing.

In one embodiment, the disclosed methods reduce the number of eosinophils in the blood, bone marrow, gastrointestinal tract (e.g., esophagus, stomach, small intestine and colon), or lung. In another embodiment, a method disclosed herein reduces the number of blood eosinophils. In a further embodiment, a method disclosed herein reduces the number of lung eosinophils. In still a further embodiment, a method disclosed herein reduces the number of eosinophil precursor cells.

In another embodiment, the disclosed methods reduce (post-administration) the number of eosinophils by at least about 10%, at least about 20%, at least about 30%, at least about 40%, at least about 50%, at least about 60%, at least about 70%, at least about 80%, at least about 90%, at least about 95% or at least about 99%. In a specific embodiment, a method disclosed herein reduces the number of eosinophils below the limit of detection.

In another embodiment, the disclosed methods reduce (post-administration) the number of eosinophil precursors by at least about 10%, at least about 20%, at least about 30%, at least about 40%, at least about 50%, at least about 60%, at least about 70%, at least about 80%, at least about 90%, at least about 95% or at least about 99%. In a specific embodiment, a method disclosed herein reduces the number of eosinophil precursors below the limit of detection.

Compounds of the disclosure can be useful for treating mast cell disorders. Compounds of the disclosure can be useful for treating mastocytosis. Mastocytosis is subdivided into two groups of disorders: (1) cutaneous mastocytosis (CM) describes forms that are limited to the skin; and (2) systemic mastocytosis (SM) describes forms in which mast cells infiltrate extracutaneous organs, with or without skin involvement. SM is further subdivided into five forms: indolent (ISM); smoldering (SSM); aggressive (ASM); SM with associated hematologic non-mast cell lineage disease (SM-AHNMD); and mast cell leukemia (MCL).

Diagnosis of SM is based in part on histological and cytological studies of bone marrow showing infiltration by mast cells of often atypical morphology, which frequently abnormally express non-mast cell markers (CD25 and/or CD2). Diagnosis of SM is confirmed when bone marrow mast cell infiltration occurs in the context of one of the following: (1) abnormal mast cell morphology (spindle-shaped cells); (2) elevated level of serum tryptase above 20 ng/mL; or (3) the presence of the activating KIT protein mutations, such as, e.g., exon 17 mutations such as D816 mutations such as D816V.

Activating mutations at the D816 position are found in the vast majority of mastocytosis cases (90-98%), with the most common mutations being D816V, D816H, and D816Y. The D816V mutation is found in the activation loop of the protein kinase domain and leads to constitutive activation of KIT kinase.

No drugs are approved for the non-advanced forms of systemic mastocytosis, ISM or SSM. Current approaches to management of these chronic diseases include nonspecific symptom-directed therapies that have varying degrees of efficacy and no effect on MC burden. Cytoreductive therapies, such as cladribine and interferon alpha, are occasionally used for intractable symptoms. Based on the current treatment landscape, there remains an unmet medical need in patients with ISM and SSM with moderate-to-severe symptoms that cannot be adequately managed by available symptom-directed therapies.

Compounds of the disclosure can be useful for treating ISM or SSM. In some embodiments, the patient with ISM or SSM has symptoms that are inadequately controlled by at least one, at least two, at least three symptomatic treatments. Symptoms can be assessed using a patient reported outcome (PRO) tool e.g. the Indolent Systemic Mastocytosis-Symptom Assessment Form (ISM-SAF) (ISPOR Europe 2019, Copenhagen Denmark, 2-6 Nov. 2019). Compounds of the disclosure can be useful for improving symptoms associated with ISM or SSM e.g., reducing or eliminating pruritus, flushing, headaches, and/or GI events, such as vomiting, diarrhea, and abdominal pain. Improvements in symptoms can be assessed using the ISM-SAF.

Compounds of the disclosure can be useful for treating other mast cell disorders, such as mast cell activation syndrome (MCAS), and hereditary alpha tryptasemia (HAT) (Picard Clin. Ther. 2013, May 35(5) 548; Akin J. Allergy Clin. Immuno. 140(2)349 62. Compounds of the disclosure can be useful for treating mast cell disorders associated with KIT and PDGFRα mutations. Compounds of the disclosure can be useful for treating mast cell diseases associated with wild type KIT and PDGFRα.

Compounds of the disclosure can be useful for treating mast cell activation syndrome (MCAS), which is an immunological condition in which mast cells inappropriately and excessively release chemical mediators, resulting in a range of chronic symptoms, sometimes including anaphylaxis or near-anaphylaxis attacks. Unlike mastocytosis, where patients have an abnormally increased number of mast cells, patients with MCAS have a normal number of mast cells that do not function properly and are defined as "hyperresponsive." Types of MCAS include primary MCAS (monoclonal mast cell activation syndrome (MMAS)), secondary MCAS (MCAS that arises from another disease), and idiopathic MCAS (MCAS that rules out primary or secondary MCAS).

Compounds of the disclosure can be useful for treating hereditary alpha tryptasemia (HAT)(overexpression of TPSAB1 causing elevated tryptase)).

Other mast cell diseases include mast cell mediated asthma, anaphylaxis (including idiopathic, Ig-E and non-Ig-E mediated), urticaria (including idiopathic and chronic), atopic dermatitis, swelling (angioedema), irritable bowel syndrome, mastocytic gastroenteritis, mastocytic colitis, pruritus, chronic pruritus, pruritus secondary to chronic kidney failure and heart, vascular, intestinal, brain, kidney, liver, pancreas, muscle, bone and skin conditions associated with mast cells. In some embodiments, the mast cell disease is not associated with mutant KIT or mutant PDGFRα.

KIT and PDGFRA mutations have been extensively studied in GIST. Compounds of the disclosure can be useful for treating GIST associated with KIT mutations. Compounds of the disclosure can be useful for treating unresectable or metastatic GIST. Nearly 80% of metastatic GISTs have a primary activating mutation in either the extracellular region (exon 9) or the juxtamembrane (JM) domain (exon 11) of the KIT gene sequence. Many mutant KIT tumors respond to treatment with targeted therapy such as imatinib, a selective tyrosine kinase inhibitor that specifically inhibits BCR-ABL, KIT, and PDGFRA proteins. However, most GIST patients eventually relapse due to a secondary mutation in KIT that markedly decreases the binding affinity of imatinib. These resistance mutations invariably arise within the adenosine 5-triphosphate (ATP)-binding pocket (exons 13 and 14) or the activation loop (exons 17 and 18) of the kinase gene. Of the currently approved agents for GIST, none are selective targeted agents. Imatinib is currently approved for the treatment of GIST; multikinase inhibitors are used after imatinib. In many cases, these multikinase inhibitors, such as, e.g., sunitinib, regorafenib, and midostaurin, only weakly inhibit imatinib resistant mutants and/or the multikinase inhibitors are limited by a more complex safety profile and a small therapeutic window. In some embodiments, compounds of the disclosure can be useful for treating GIST in patients who have been treated with imatinib. Compounds of the disclosure can be useful for treating GIST as first line (1L), second line (2L), third line (3L) or fourth line (4L) therapy.

Compounds of the disclosure can be useful for treating GIST when particular mutations in KIT are absent or present. In some embodiments, compounds of the disclosure are capable of treating GIST when particular mutations in KIT are absent. In certain embodiments, compounds of the disclosure are not capable of treating GIST when particular mutations in KIT are present. In some embodiments, compounds of the disclosure do not provide clinical benefit in patients harboring KIT ATP binding pocket mutations (KIT protein mutations V654A, N655T, and/or T670I).

Compounds of the disclosure can be useful for treating GIST associated with PDGFRA mutations. In 5 to 6% of unresectable of metastatic GIST patients, an activation loop mutation in exon 18 of the gene sequence of PDGFRA at the protein amino acid 842 occurs as the primary mutation.

Compounds of the disclosure can also be useful in treating AML. AML patients also harbor KIT mutations, with the majority of these mutations at the D816 position of the KIT protein.

In some embodiments, the compounds of the disclosure are administered to a subject in need thereof. In some embodiments, the compounds of the disclosure are administered as a pharmaceutical formulation, wherein the compound is combined with one or more pharmaceutically acceptable excipients or carriers. Thus, in some embodiments, disclosed herein are compositions comprising at least one entity chosen from compounds of Formula I and pharmaceutically acceptable salts thereof and/or solvates of any of the foregoing and optionally further comprising at least one pharmaceutically acceptable excipient.

Compounds of the disclosure may be formulated for administration in any convenient way for use in human or veterinary medicine. In some embodiments, the compound included in the pharmaceutical compositions may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as, e.g., lactose, glucose, and sucrose; (2) starches, such as, e.g., corn starch and potato starch; (3) cellulose and its derivatives, such as, e.g., sodium carboxymethyl cellulose, ethyl cellulose, and cellulose acetate; (4) powdered tragacanth; (5) malt; (6) gelatin; (7) talc; (8) excipients, such as, e.g., cocoa butter and suppository waxes; (9) oils, such as, e.g., peanut oil, cottonseed oil, safflower oil, sesame oil, olive oil, corn oil, and soybean oil; (10) glycols, such as, e.g., propylene glycol; (11) polyols, such as, e.g., glycerin, sorbitol, mannitol, and polyethylene glycol; (12) esters, such as, e.g., ethyl oleate and ethyl laurate; (13) agar; (14) buffering agents, such as, e.g., magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins, such as, e.g., Captisol®; and (22) other non-toxic compatible substances employed in pharmaceutical formulations.

Examples of pharmaceutically acceptable antioxidants include: (1) water soluble antioxidants, such as, e.g., ascorbic acid, cysteine hydrochloride, sodium bisulfate, sodium metabisulfite, sodium sulfite, and the like; (2) oil-soluble antioxidants, such as, e.g., ascorbyl palmitate, butylated hydroxyanisole (BHA), butylated hydroxytoluene (BHT), lecithin, propyl gallate, alpha-tocopherol, and the like; and (3) metal chelating agents, such as, e.g., citric acid, ethylenediamine tetraacetic acid (EDTA), sorbitol, tartaric acid, phosphoric acid, and the like.

Solid dosage forms (e.g., capsules, tablets, pills, dragees, powders, granules, and the like) can include one or more pharmaceutically acceptable carriers, such as, e.g., sodium citrate or dicalcium phosphate, and/or any of the following: (1) fillers or extenders, such as, e.g., starches, lactose, sucrose, glucose, mannitol, and/or silicic acid; (2) binders, such as, e.g., carboxymethylcellulose, alginates, gelatin, polyvinyl pyrrolidone, sucrose, and/or acacia; (3) humectants, such as, e.g., glycerol; (4) disintegrating agents, such as, e.g., agar-agar, calcium carbonate, potato or tapioca starch, alginic acid, certain silicates, and sodium carbonate; (5) solution retarding agents, such as, e.g., paraffin; (6) absorption accelerators, such as, e.g., quaternary ammonium compounds; (7) wetting agents, such as, e.g., cetyl alcohol and glycerol monostearate; (8) absorbents, such as, e.g., kaolin and bentonite clay; (9) lubricants, such as, e.g., talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups, and elixirs. In addition to the active ingredient, the liquid dosage forms may contain inert diluents commonly used in the art, such as, e.g., water or other solvents, solubilizing agents, and emulsifiers, such as, e.g., ethyl alcohol, isopropyl alcohol, ethyl carbonate, ethyl acetate, benzyl alcohol, benzyl benzoate, propylene glycol, 1,3-butylene glycol, oils (such as, e.g., cottonseed, groundnut, corn, germ, olive, castor, and sesame oils), glycerol, tetrahydrofuryl alcohol, polyethylene glycols and fatty acid esters of sorbitan, and mixtures thereof.

Suspensions, in addition to the active compounds, may contain suspending agents as, e.g., ethoxylated isostearyl alcohols, polyoxyethylene sorbitol and sorbitan esters, microcrystalline cellulose, aluminum metahydroxide, bentonite, agar-agar, tragacanth, and mixtures thereof.

Ointments, pastes, creams and gels may contain, in addition to an active compound, excipients, such as, e.g., animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to an active compound, excipients such as, e.g., lactose, talc, silicic acid, aluminum hydroxide, calcium silicates, and polyamide powder, or mixtures of these substances. Sprays can additionally contain customary propellants, such as, e.g., chlorofluorohydrocarbons and volatile unsubstituted hydrocarbons, such as, e.g., butane and propane.

Non-limiting examples of dosage forms for the topical or transdermal administration of compounds of the disclosure include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required.

When a compound of the disclosure is administered as a pharmaceutical to humans and animals, the compound can be given per se or as a pharmaceutical composition containing, for example, 0.1 to 99.5% (such as 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

In addition, compounds of the disclosure can be administered alone or in combination with other compounds, including other KIT- or PDGFRα modulating compounds, or other therapeutic agents. In some embodiments, a compound of the disclosure can be administered in combination with ripretinib. In some embodiments, a compound of the disclosure can be administered in combination with one or more compounds selected from imatinib, sunitinib, regorafenib, cabozantinib, crenolanib, midostaurin, brentuximab vedotin, and mastitinib for treating a disease or condition disclosed herein.

Compounds of the disclosure can be administered to a patient, who has had prior treatment with another compound or compounds. Compounds of the disclosure can be useful as first line (1L), second line (2L), third line (3L), or fourth line (4L) therapy.

In some embodiments, a compound of the disclosure is administered after prior treatment with imatinib.

Compounds of the disclosure can be administered to a patient who has had no prior treatment with midostaurin. In some embodiments, compounds of the disclosure can be administered to a patient who has had prior treatment with midostaurin.

EXAMPLES

General Synthetic Methods and Intermediates

Definitions

C Celsius
Cs$_2$CO$_3$ cesium carbonate
DCM dichloromethane
DIPEA diisopropylamine
DMF dimethyl formamide
DMSO dimethylsulfoxide
EA ethyl acetate
EDCI 1-ethyl-3-(3-dimethylaminopropyl)carbodiimide
h hours
H$_2$ hydrogen gas
H$_2$O water
HCl hydrochloric acid
HOAc acetic acid
HOBT hydroxybenzotriazole
HPLC high performance liquid chromatography
IC50 inhibitory concentration 50%
IPA isopropyl alcohol
K$_2$CO$_3$ potassium carbonate
KOAc potassium acetate
LCMS liquid chromatography mass spectrometry
LiAlH$_4$ lithium aluminum hydride
min minutes
MsCl mesyl chloride
MTBE methyl tert-butyl ether
MeOH methanol
N$_2$ nitrogen gas
NaOH sodium hydroxide
Na$_2$SO$_4$ sodium sulfate
NH$_4$HCO$_3$ ammonium formate
NMP N-methylpyrrolidinone
Pd/C palladium on carbon
Pd(dppf)Cl$_2$ [1,1'-bis(diphenylphosphino)ferrocene]dichloropalladium(II)
PE petroleum ether
RT room temperature
TEA triethylamine
THF tetrahydrofuran
TsCl tosyl chloride Methods for preparing compounds of the disclosure can be carried out in suitable solvents which can be readily selected by one of skill in the art of organic synthesis. Suitable solvents can be substantially non-reactive with the starting materials (reactants), intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC).

Analytical Instruments and Methods for Compound Characterization:

LC-MS: Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in H$_2$O and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in H$_2$O and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were performed in a Biotage Initiator microwave unit.

Silica gel chromatography: Silica gel chromatography was performed on either a Teledyne Isco CombiFlash® Rf unit or a Biotage® Isolera Four unit.

Proton NMR: Unless otherwise indicated, all $^1$H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d6 solvent as parts-per million (ppm) with respect to residual DMSO (2.50 ppm).

One of ordinary skill in the art will recognize that modifications of the gradient, column length, and flow rate are possible and that some conditions may be more suitable for compound characterization than others, depending on the chemical species being analyzed.

Example 1: Synthetic Preparations

Preparation of Intermediates

Preparation 1: (S)-1-(2-(4-(6-bromopyrrolo[2,1-f][1,2,4]triazin-4-yl)piperazin-1-yl)pyrimidin-5-yl)-1-(4-fluorophenyl)ethan-1-amine (I-1)

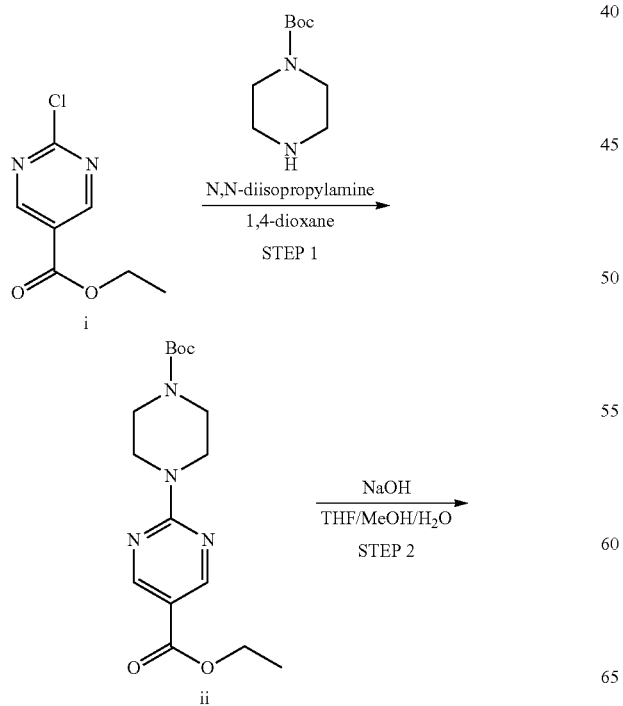

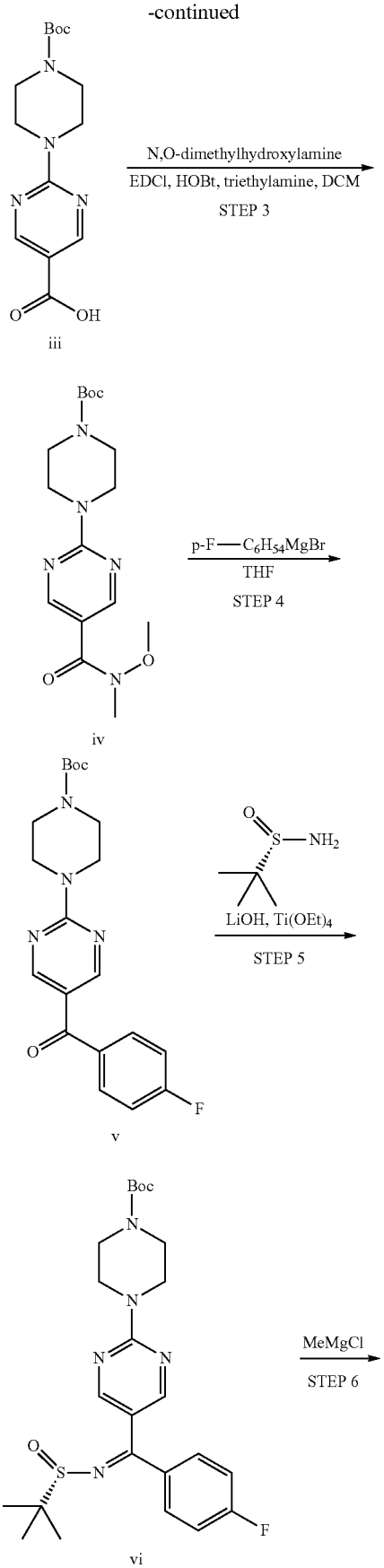

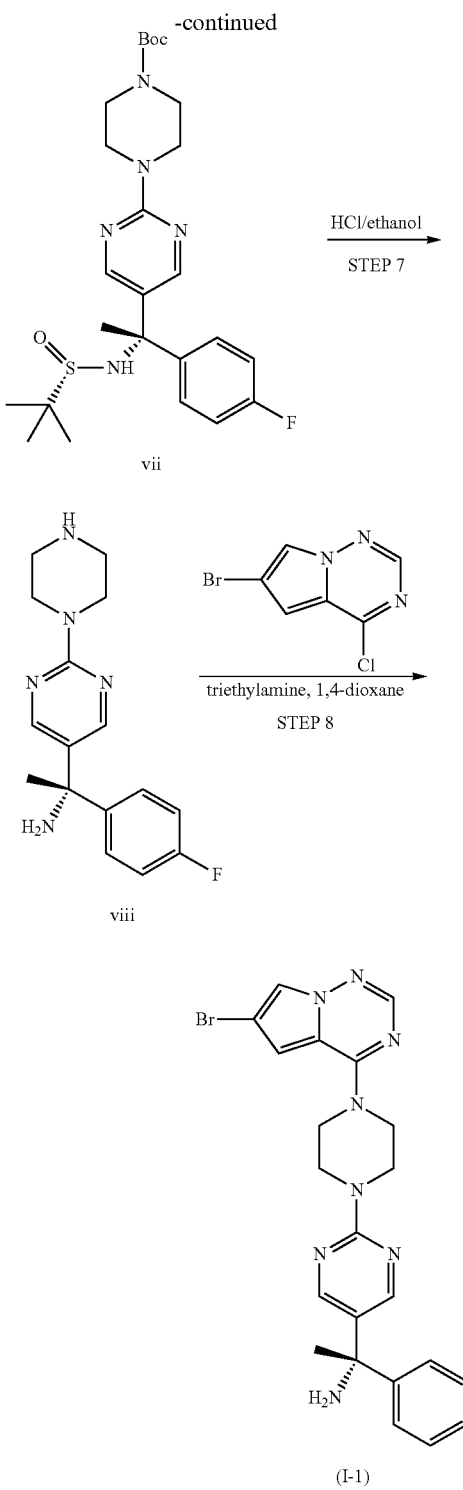

in the next step without the further purification. MS (ES+) $C_{16}H_{24}N_4O_4$ requires: 336, found: 237, 281 $[M-56+H]^+$.

Step 2: Synthesis of 2-(4-(tert-butoxycarbonyl)piperazin-1-yl)pyrimidine-5-carboxylic acid (iii): To a solution of ethyl 2-(4-(tert-butoxycarbonyl)piperazin-1-yl)pyrimidine-5-carboxylate (ii) (17 g, crude) in THF/MeOH/H$_2$O (300 mL) was added sodium hydroxide (4.3 g, 107.5 mmol), and the reaction was stirred at 70° C. for 2 h. LCMS showed the reaction was completed. The reaction mixture was cooled to RT, acidified to pH≈5-6 with 1 M HCl and filtered. The solid was collected and dried to give the title compound (iii) (16 g, 96%) as a white solid, which was directly used in the next step without further purification. MS (ES+) $C_{14}H_{20}N_4O_4$ requires: 308, found: 253 $[M-56+H]^+$.

Step 3: Synthesis of tert-butyl 4-(5-(methoxy(methyl)carbamoyl)pyrimidin-2-yl)piperazine-1-carboxylate (iv): To a suspension of 2-(4-(tert-butoxycarbonyl)piperazin-1-yl)pyrimidine-5-carboxylic acid (iii) (13.8 g, 44.8 mmol), EDCI (12.8 g, 67.2 mmol) and HOBT (7.2 g, 53.7 mmol) in DCM (200 mL) was added TEA (25 mL, 179.2 mmol), and the mixture was stirred at RT for 1 h, followed by the addition of N,O-dimethylhydroxylamine (5 g, 53.7 mmol). The reaction mixture was stirred for another 3 h. LCMS showed the reaction was completed. The reaction mixture was washed with H$_2$O (100 mL), and the organic layer was dried, filtered, and concentrated. The residue was purified by silica gel chromatography (petroleum ether:ethyl acetate=1:1) to give the title compound (iv) (11.2 g, 67%) as a white solid. MS (ES+) $C_{16}H_{25}N_5O_4$ requires: 351, found: 296 $[M-56+H]^+$. found: 296 $[M-56+H]^+$.

Step 4: Synthesis of tert-butyl 4-(5-(4-fluorobenzoyl)pyrimidin-2-yl)piperazine-1-carboxylate (v): To a solution of tert-butyl 4-(5-(methoxy(methyl)carbamoyl)pyrimidin-2-yl)piperazine-1-carboxylate (iv) (7.8 g, 22.22 mmol) in dry THF (50 mL) was added $C_6H_5MgFBr$ (1 M in THF, 50 mL) at 0° C. under nitrogen, and the mixture was stirred at RT for 3 h. LCMS showed the reaction was completed. The reaction mixture was quenched with 1 M HCl and extracted with EA. The combined organic layers were washed with H$_2$O and brine, dried over sodium sulfate, filtered and concentrated. The residue was purified by silica gel chromatography (petroleum ether:EA=5:1) to give the title compound (v) (7.2 g, 84%) as a yellow solid. MS (ES+) $C_{20}H_{23}FN_4O_3$ requires: 386, found: 331 $[M-56+H]^+$.

Step 5: Synthesis of tert-Butyl (S,Z)-4-(5-(((tert-butylsulfinyl)imino)(4-fluorophenyl)methyl)-pyrimidin-2-yl)piperazine-1-carboxylate (vi): tert-Butyl 4-(5-(4-fluorobenzoyl)pyrimidin-2-yl)piperazine-1-carboxylate (v) (20.0 g, 1.0 eq), (S)-(−)-2-methyl-2-propanesulfinamide (9.43 g, 1.5 eq), and LiOH (0.64 g, 0.5 eq) were added to a reaction vessel with toluene (160 mL). To this mixture, titanium(IV) isopropoxide (18.42 g, 1.25 eq) was added and the reaction mixture agitated at 50-60° C. for 1 h. The reaction mixture was then distilled to remove 80 mL while charging additional toluene (80 mL) at 40-60° C. The reaction mixture was cooled 20-30° C. and added to a monosodium citrate solution (80 mL, 30%-w/w citric acid at pH 3-4). The mixture was agitated 1.5 h at 45-55° C. and then the phases separated. The organic phase was washed with potassium bicarbonate (40 mL, 25%-w/w aqueous) and the organic phase distilled to remove 40 mL. The product solution of (vi) was diluted with THF (30 mL) before being used in the next step directly as a solution (approx. 15% w/w).

Step 6: Synthesis of tert-Butyl 4-(5-((S)-1-(((S)-tert-butylsulfinyl)amino)-1-(4-fluorophenyl)ethyl)pyrimidin-2-yl)piperazine-1-carboxylate (vii): To the solution of tert-butyl (S,Z)-4-(5-(((tert-butylsulfinyl)imino)(4-fluorophenyl)

Step 1: Synthesis of ethyl 2-(4-(tert-butoxycarbonyl)piperazin-1-yl)pyrimidine-5-carboxylate (ii): To a solution of tert-butyl piperazine-1-carboxylate (i) (10.0 g, 53.7 mmol) and diisopropylethylamine (23.4 mL, 134.25 mmol) in dioxane (80 mL) was added ethyl 2-chloropyrimidine-5-carboxylate (10 g, 53.7 mmoL), and the reaction mixture was stirred at RT for 3 h. LCMS showed the reaction was completed. The reaction mixture was concentrated to afford the title compound (ii) (17 g, crude), which was directly used methyl)-pyrimidin-2-yl)piperazine-1-carboxylate (vi) in toluene/THF (120 g, prepared in step 5) was added methyl magnesium chloride (27.8 g, 22%-w/w in THF, 2.0 eq) at 10° C. over 2-3 h. The reaction mixture was allowed to agitate 1.5 h to reach reaction completion. The reaction mixture was quenched by the addition of methanol (40 mL) followed by H$_2$O (10 mL). The mixture was distilled to remove 100-110 mL and then washed with ammonium chloride (80 mL, 20%-w/w in H2O). The organic phase was washed with H$_2$O (80 mL), diluted with toluene (60 mL), and distilled to remove 60-80 mL distillate. The solution at 50-60° C. was charged with n-heptane (80 mL) and then cooled to 42° C., at which time seeds were added (25-50 mg). The solution was held 30 minutes and then cooled to 0-10° C. for 30 minutes. The solids were isolated by filtration, washed with n-heptane and toluene mixture (1:1, 30 mL) followed by n-heptane (30 mL). The product was dried to give 9 g of the crude product 96.4 to 97.2% de. (vii)

Step 6a: Recrystallization of crude tert-Butyl 4-(5-((S)-1-(((S)-tert-butylsulfinyl)amino)-1-(4-fluorophenyl)ethyl)pyrimidin-2-yl)piperazine-1-carboxylate: tert-Butyl 4-(5-((S)-1-(((S)-tert-butylsulfinyl)amino)-1-(4-fluorophenyl)ethyl)pyrimidin-2-yl)piperazine-1-carboxylate (10.0 g) was dissolved in isopropanol (100 mL) and heated to 40-60° C. then passed through a clarifying filter, washing/rinsing with isopropanol (20 mL). The resulting solution was vacuum distilled at 40-60° C. to remove 60-70 mL. The mixture was diluted with water (45 mL) at 50-60° C. and then cooled to 40° C., at which time it was seeded with 25-50 mg. The mixture was further cooled to 20-25° C. and water (20 mL) was added. The solids were isolated by filtration, washed with isopropanol/water mixture (1:1, 20 mL), and then slurry washed with isopropanol/water (1:2, 30 mL). Drying gave 8.5 g of product>99.8% de (vii).

Step 7: Synthesis of (S)-1-(4-fluorophenyl)-1-(2-(piperazin-1-yl)pyrimidin-5-yl)ethan-1-amine hydrochloride (viii): tert-Butyl-4-(5-((S)-1-(((S)-tert-butylsulfinyl)amino)-1-(4-fluorophenyl)-ethyl)pyrimidin-2-yl)piperazine-1-carboxylate (vii) (50 g, 1 eq) was mixed with ethanol (7.5 vol) and concentrated hydrochloric acid (11.2 M, 5.6 eq). The reaction mixture was heated to reflux temperature. After the reaction had reached completion by LCMS, the mixture was concentrated to 5 vol under atmospheric pressure. Concentration was continued with addition of ethanol to maintain 5 vol until H$_2$O content≤3%. Concentration was finally stopped at 2 volumes followed by cooling to 0-5° C. over 30 minutes. Filtration was followed by drying under vacuum to give the title product of (viii) (92% yield).

Step 8: Synthesis of (S)-1-(2-(4-(6-Bromopyrrolo[2,1-f][1,2,4]triazin-4-yl)piperazin-1-yl)pyrimidin-5-yl)-1-(4-fluorophenyl)ethanamine (I-1): A mixture of commercially available 6-bromo-4-chloropyrrolo[2,1-f][1,2,4]triazine (4.00 g, 17.2 mmol)(e.g., Sigma Aldrich), (S)-1-(4-fluorophenyl)-1-(2-(piperazin-1-yl)pyrimidin-5-yl)ethanamine hydrochloride (viii) (5.81 g, 17.2 mmol) and triethylamine (7.20 mL, 51.6 mmol) in dioxane (50 mL) was stirred at RT overnight. The mixture was concentrated, then purified by flash column chromatography (DCM/MeOH=20/1) to afford the title compound (I-1) (8.0 g, 94% yield) as a white solid. MS (ES+) C$_{22}$H$_{22}$BrFN$_8$ requires: 496, found: 497, 499 [M+H]$^+$.

Preparation 2: (S)-1-(2-(4-(6-(1H-pyrazol-4-yl)pyrrolo[2,1-f][1,2,4]triazin-4-yl)piperazin-1-yl)pyrimidin-5-yl)-1-(4-fluorophenyl)ethanamine (I-2)

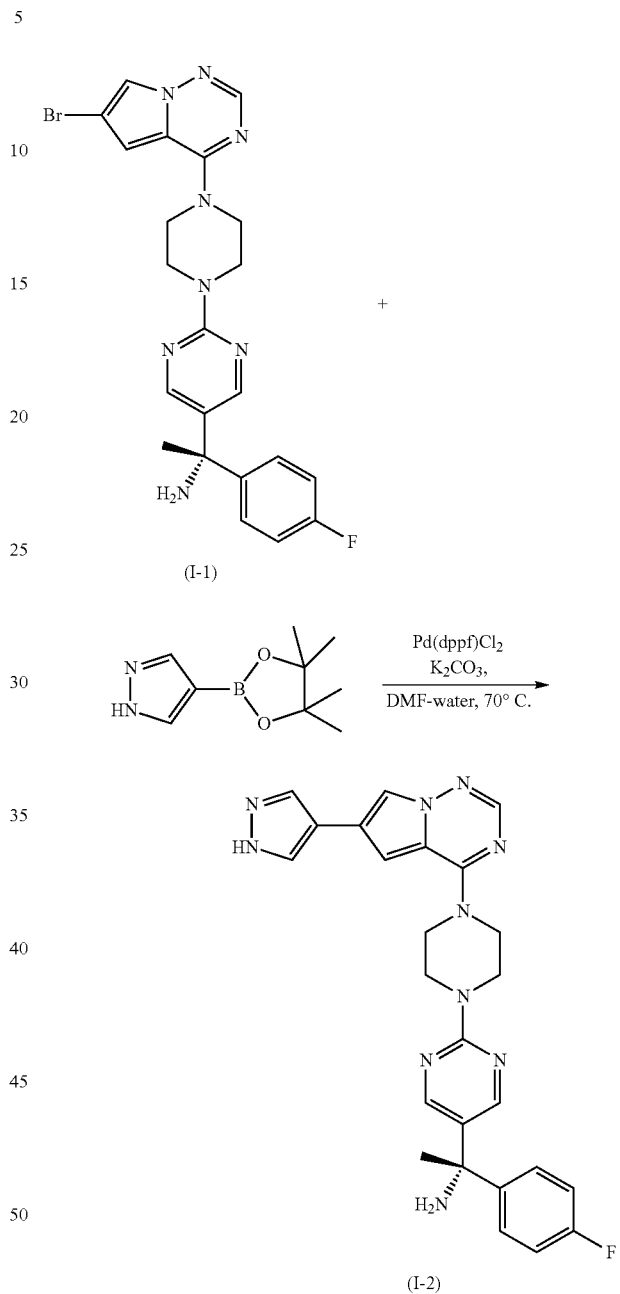

A mixture of I-1 (3.0 g, 6.05 mmol), 4-(4,4,5,5-tetramethyl-1,3,2-dioxaborolan-2-yl)-1H-pyrazole (1.17 g, 6.05 mmol), Pd(dppf)Cl$_2$ (494 mg, 605 µmol) and K$_2$CO$_3$ (2.50 g, 18.2 mmol) in DMF/H$_2$O (40 mL/10 mL) was purged with N$_2$ (g) for 10 mins and stirred at 70° C. for 16 h under N$_2$. After that, the solution was diluted with EA, washed with H$_2$O and brine, and concentrated. The residue was purified by flash column chromatography on silica gel (DCM/MeOH=10/1) to afford the title compound (I-2) (2.0 g, 68% yield) as a yellow solid. MS (ES+) C$_{25}$H$_{25}$FN$_{10}$ requires: 484, found: 485 [M+H]$^+$.

Preparation 3: (S)-1-(4-fluorophenyl)-1-(2-(4-(6-(4,4,5,5-tetramethyl-1,3,2-dioxaborolan-2-yl)pyrrolo[2,1-f][1,2,4]triazin-4-yl)piperazin-1-yl)pyrimidin-5-yl)ethanamine (I-3)

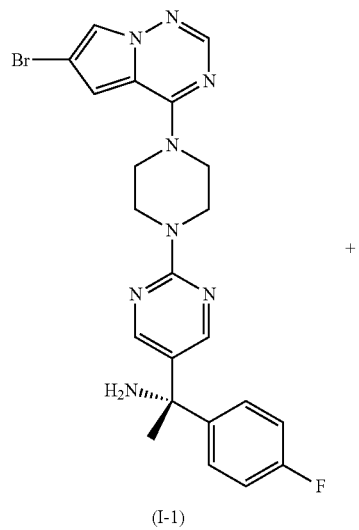

(I-1)

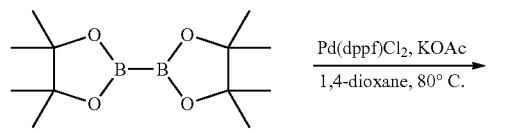

Pd(dppf)Cl₂, KOAc
1,4-dioxane, 80° C.

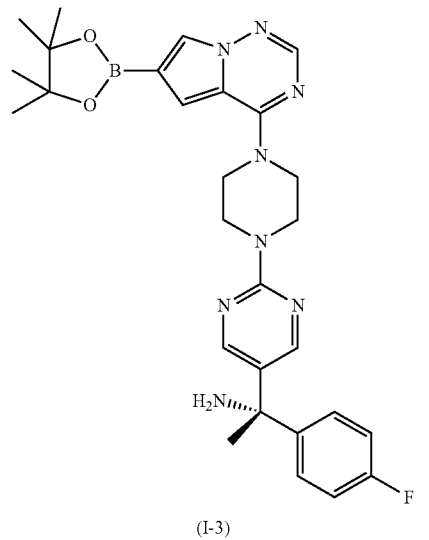

(I-3)

A mixture of I-1 (1.0 g, 2.02 mmol), 4,4,4',4',5,5,5',5'-octamethyl-2,2'-bi(1,3,2-dioxaborolane) (768 mg, 3.12 mmol), Pd(dppf)Cl₂ (165 mg, 202 mol), dppf (167 mg, 303 μmol) and KOAc (395 mg, 4.04 mmol) in 1,4-dioxane (30 mL) was purged with N₂ (g) for 10 min and stirred at 80° C. for 16 h. After that, the solution was diluted with EA, washed with H₂O and brine, and concentrated. The residue was purified by flash column chromatography on silica gel (DCM/MeOH=15/1) to afford the title compound (I-3) (700 mg) as a gray solid. MS (ES+) C28H34BFN8O2 requires: 544, found: 545 [M+H]⁺.

Preparation of Compounds

Example 1: (S)-1-(4-(4-(4-(5-(1-Amino-1-(4-fluorophenyl)ethyl)pyrimidin-2-yl)piperazin-1-yl)pyrrolo[2,1-f][1,2,4]triazin-6-yl)-1H-pyrazol-1-yl)-2-methylpropan-2-ol (1)

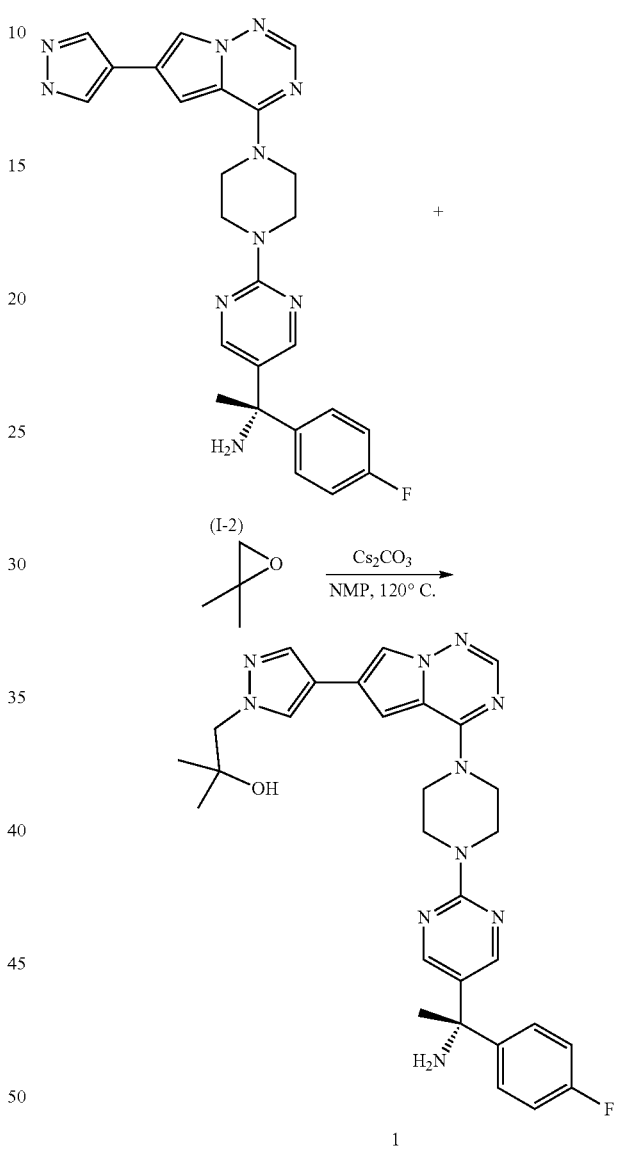

A mixture of 1-2 (prepared according to preparation 2) (200 mg, 0.412 mmol), Cs₂CO₃ (269 mg, 0.83 mmol) and 2,2-dimethyloxirane (89.3 mg, 1.24 mmol) in NMP (5 mL) was stirred at 120° C. for 10 h. The reaction mixture was diluted with EtOAc, washed with H₂O and brine, and dried over Na₂SO₄. The organic layer was concentrated in vacuum, and the residue was purified by Prep-HPLC (Mobile phase: A=H₂O (0.1% NH₄HCO₃), B=acetonitrile; Gradient: B=15%-95% in 18 min; Column: Xtimate™ 10 um 150A 21.2×250 mm) followed by lyophilization to give the title compound (1) (74.5 mg, 32% yield) as a white solid. MS (ES+) C29H33FN10O requires: 556, found: 557 [M+H]⁺. ¹H-NMR (400 MHz, 6d-DMSO) δ ppm 8.41 (s, 2H), 8.03 (s, 1H), 8.02 (s, 1H), 7.87 (s, 1H), 7.84 (s, 1H), 7.49-7.45 (m, 2H), 7.25 (s, 1H), 7.13-7.08 (m, 2H), 4.76 (s, 1H), 4.12-4.07 (m, 4H), 4.02 (s, 2H), 3.93-3.90 (m, 4H), 2.44 (s, 2H), 1.73 (s, 3H), 1.10 (s, 6H).

Example 2: (S)-2-(4-(4-(4-(5-(1-amino-1-(4-fluorophenyl)ethyl)pyrimidin-2-yl)piperazin-1-yl)pyrrolo[2,1-f][1,2,4]triazin-6-yl)-1H-pyrazol-1-yl)-2-methylpropan-1-ol (2)

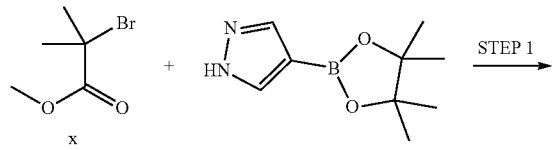

Step 1: Synthesis of Methyl 2-methyl-2-(4-(4,4,5,5-tetramethyl-1,3,2-dioxaborolan-2-yl)-1H-pyrazol-1-yl)propanoate (xii) To a solution of methyl 2-bromo-2-methylpropanoate (x) (3.0 g, 16.7 mmol) and 4-(4,4,5,5-tetramethyl-1,3,2-dioxaborolan-2-yl)-1H-pyrazole (xi) (3.23 g, 16.7 mmol) in NMP (20 mL) was added cesium carbonate (16.2 g, 50 mmol) and sodium iodide (3.1 g, 16.7 mmol) at RT. The resulting mixture was stirred at 120° C. for 8 h. The reaction mixture was diluted with DCM and washed in sequence with $H_2O$ and brine. The organic layer was concentrated in vacuo, and the residue was purified by flash column chromatography on silica gel (petroleum ether:ethyl acetate=5/1) to afford the title compound (xii) (1.5 g, 30% yield) as a colorless oil.

Step 2: Synthesis of Methyl (S)-2-(4-(4-(4-(5-(1-amino-1-(4-fluorophenyl)ethyl)pyrimidin-2-yl)piperazin-1-yl)pyrrolo[2,1-f][1,2,4]triazin-6-yl)-1H-pyrazol-1-yl)-2-methylpropanoate (xiii): A mixture of methyl 2-methyl-2-(4-(4,4,5,5-tetramethyl-1,3,2-dioxaborolan-2-yl)-1H-pyrazol-1-yl)propanoate (xii) (178 mg, 0.6 mmol), I-1 (300 mg, 0.6 mmol), Pd(dppf)Cl$_2$ (99 mg, 0.12 mmol) and K$_2$CO$_3$ (251 mg, 1.8 mmol) in DMF/H$_2$O (8 mL/2 mL) was stirred at 70° C. for 4 h under N$_2$ (g). After that, the solution was diluted with DCM, washed with H$_2$O and brine, and concentrated. The residue was purified by flash column chromatography on silica gel (DCM/MeOH=10/1) to afford the title compound (xiii) (240 mg, 68% yield) as a white solid. MS (ES+) $C_{30}H_{33}FN_{10}O_2$ requires: 584, found: 585 [M+H]$^+$.

Step 3: Synthesis of (S)-2-(4-(4-(4-(5-(1-Amino-1-(4-fluorophenyl)ethyl)pyrimidin-2-yl)piperazin-1-yl)pyrrolo[2,1-f][1,2,4]triazin-6-yl)-1H-pyrazol-1-yl)-2-methylpropan-1-ol (2): To a solution of (S)-methyl 2-(4-(4-(4-(5-(1-amino-1-(4-fluorophenyl)ethyl)pyrimidin-2-yl)piperazin-1-yl)pyrrolo[2,1-f][1,2,4]triazin-6-yl)-1H-pyrazol-1-yl)-2-methylpropanoate (xiii) (200 mg, 0.34 mmol) in THF (20 mL) was added LiAlH$_4$ (100 mg, 3.4 mmol) at 0° C., and the resulting mixture was stirred at RT for 6 h. The reaction mixture was quenched with H$_2$O (100 mL) and 10% NaOH H$_2$O (300 mL) then extracted with EA. The organic layer was concentrated in vacuo, and the residue was purified by Prep-HPLC (Mobile phase: A=H$_2$O (0.1% NH$_4$HCO$_3$), B=acetonitrile; Gradient: B=15%-95% in 18 min; Column: Xtimate™ 10 um 150A 21.2×250 mm) followed by lyophilization to afford the title compound (2) (90.5 mg, 47% yield) as a white solid. MS (ES+) $C_{29}H_{33}FN_{10}O$ requires: 556, found: 557 [M+H]⁺. ¹H-NMR (400 MHz, 6d-DMSO) δ ppm 8.41 (s, 2H), 8.18 (s, 1H), 8.01 (d, 1H, J=1.6 Hz), 7.87 (s, 1H), 7.84 (s, 1H), 7.52-7.43 (m, 2H), 7.26 (d, 1H, J=1.6 Hz), 7.16-7.07 (m, 2H), 4.99 (t, 1H, J=5.6 Hz), 4.17-4.04 (m, 4H), 3.98-3.87 (m, 4H), 3.60 (d, 2H, J=5.6 Hz), 2.47 (s, 2H), 1.74 (s, 3H), 1.50 (s, 6H).

Example 3: (R)1-{4-[4-(4-{5-[(S)-1-Amino-1-(4-fluoro-phenyl)-ethyl]-pyrimidin-2-yl}-piperazin-1-yl)-pyrrolo[2,1-f][1,2,4]triazin-6-yl]-pyrazol-1-yl}-propan-2-ol (3)

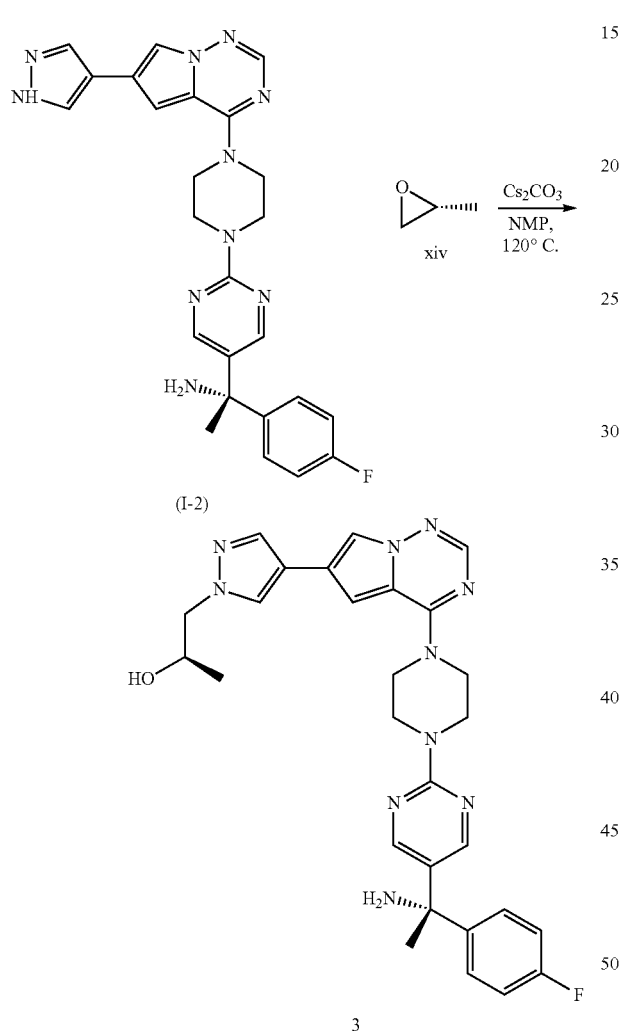

To a solution of I-2 (prepared according to preparation 2) (200 mg, 412 μmol) and (2R)-2-methyloxirane (xiv) (71.4 mg, 1.23 mmol) in NMP (3.0 mL) was added Cs₂CO₃ (400 mg, 1.23 mmol) at RT. The mixture was stirred at 120° C. for 2 h. After that, the solution was diluted with EA, washed with H₂O and brine, and concentrated. The residue was purified by Prep-HPLC (Mobile phase: A=H₂O (0.1% NH₄HCO₃), B=acetonitrile; Gradient: B=15%-95% in 18 min; Column: Xtimate™ 10 um 150A 21.2×250 mm) followed by lyophilization to give the title compound (3) (90.0 mg, 40% yield) as a white solid. MS (ES+) $C_{28}H_{31}FN_{10}O$ requires: 542, found: 543 [M+H]⁺. ¹H-NMR (400 MHz, DMSO-d6) δ ppm 8.40 (s, 2H), 8.05 (s, 1H), 7.80 (d, 1H, J=1.6 Hz), 7.87 (s, 1H), 7.83 (s, 1H), 7.46 (dd, 2H, J=8.8, 5.6 Hz), 7.24 (s, 1H), 7.10 (t, 2H, J=8.8 Hz), 4.96 (d, 1H, J=4.8 Hz), 4.11-4.08 (m, 4H), 4.02-3.95 (m, 3H), 3.92-3.89 (m, 4H), 2.45 (s, 2H), 1.73 (s, 3H), 1.05 (d, 3H, J=5.6 Hz).

Example 4: (S)-2-(4-(4-(4-(5-(1-Amino-1-(4-fluoro-phenyl)ethyl)pyrimidin-2-yl)piperazin-1-yl)pyrrolo[2,1-f][1,2,4]triazin-6-yl)-1H-pyrazol-1-yl)ethanol (4)

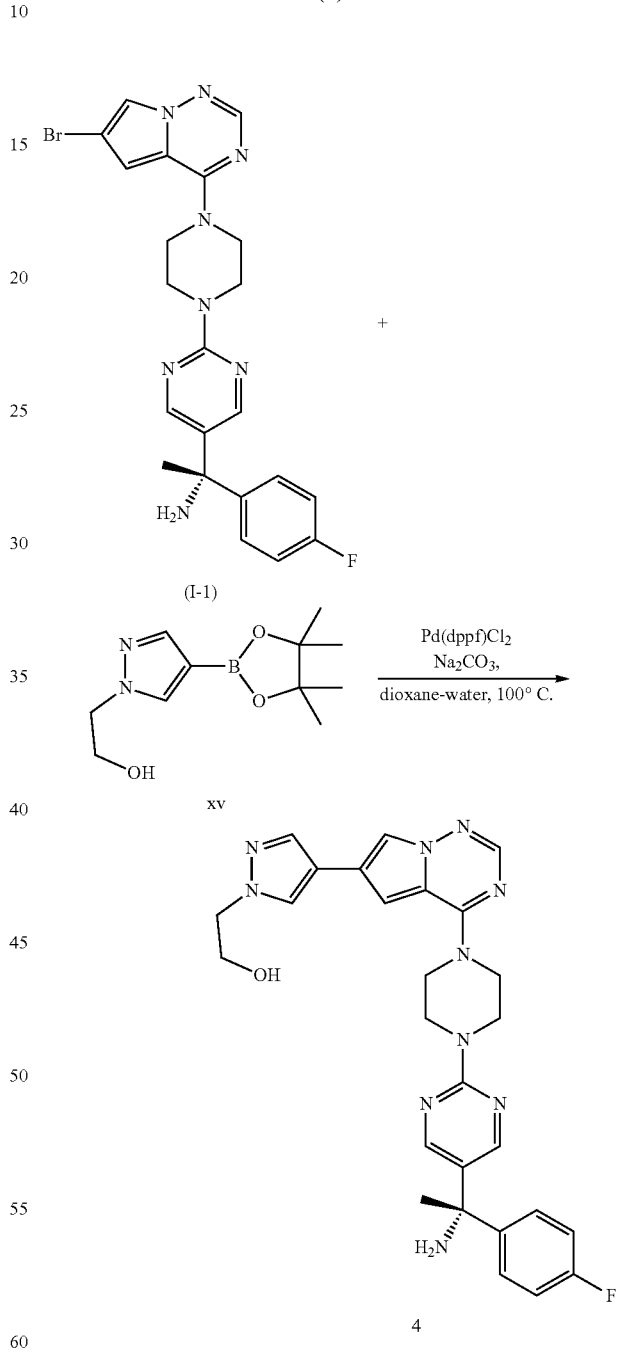

The reaction mixture of I-1 (prepared according to preparation 1) (500 mg, 1.00 mmol), commercially available 2-(4-(4,4,5,5-tetramethyl-1,3,2-dioxaborolan-2-yl)-1H-pyrazol-1-yl)ethanol (xv) (285 mg, 1.20 mmol)(e.g., AstraTech), Pd(dppf)Cl₂ (219 mg, 300 μmol) and Na₂CO₃ (317 mg, 3.00 mmol) in dioxane/H₂O (20 mL/2 mL) was stirred at 100° C. for overnight under N₂ (g). The layers were separated, and the organic layer was concentrated in vacuo. The residue was purified by flash column chromatography on silica gel (DCM/MeOH=15/1). The resulting material was purified further by Prep-HPLC (Mobile phase: A=H$_2$O (0.1% NH$_4$HCO$_3$), B=acetonitrile; Gradient: B=15%-95% in 18 min; Column: Xtimate™ 10 μm 150A 21.2×250 mm) followed by lyophilization to afford the title compound (4) (154.0 mg, 29% yield) as a white solid. MS (ES+) C$_{27}$H$_{29}$FN$_{10}$O requires: 528, found: 529 [M+H]$^+$. $^1$H-NMR (400 MHz, 6d-DMSO) δ ppm 8.40 (s, 1H), 8.07 (s, 1H), 7.99 (s, 1H), 7.87 (s, 1H), 7.84 (s, 1H), 7.49-7.44 (m, 2H), 7.24 (s, 1H), 7.14-7.06 (m, 2H), 4.93 (t, 1H, J=5.2 Hz), 4.17-4.13 (m, 2H), 4.12-4.07 (m, 4H), 3.94-3.88 (m, 4H), 3.89-3.71 (m, 2H), 2.45 (br. S., 2H), 1.73 (s, 3H).

Example 4A: (S)-2-(4-(4-(4-(5-(1-amino-1-(4-fluorophenyl)ethyl)pyrimidin-2-yl)piperazin-1-yl)pyrrolo[2,1-f][1,2,4]triazin-6-yl)-1H-pyrazol-1-yl)ethanol hydrochloride To a solution of (S)-2-(4-(4-(4-(5-(1-amino-1-(4-fluorophenyl)ethyl)pyrimidin-2-yl)piperazin-1-yl)pyrrolo[2,1-f][1,2,4]triazin-6-yl)-1H-pyrazol-1-yl)ethanol (30 mg, 0.057 mmol) in MeOH (5 mL) was added HCl/dioxane (0.05 mL, 4.0 M) at RT. The solution was stirred at RT for 16 h. The solvent was removed under reduced pressure and the product was lyophilized to afford the title compound (36.0 mg, 100% yield) as a white solid which is moisture sensitive. MS (ES+) C29H31FN100 requires: 528, found: 529 [M+H]+. 1H-NMR (400 MHz, 6d-DMSO) δ ppm 9.47 (s, 3H, br), 8.45 (s, 2H), 8.14 (s, 1H), 8.11 (s, 1H), 7.97 (s, 1H), 7.87 (s, 1H), 7.53-7.50 (m, 2H), 7.44 (s, 1H), 7.31-7.28 (m, 2H), 4.16-4.14 (m, 6H), 4.00-3.89 (m, 4H), 3.76-3.74 (m, 2H), 2.03 (s, 3H).

Example 5: (R)-2-(4-(4-(4-(5-((S)-1-Amino-1-(4-fluorophenyl)ethyl) pyrimidin-2-yl)piperazin-1-yl) pyrrolo[2,1-f][1,2,4]triazin-6-yl)-1H-pyrazol-1-yl) propan-1-ol (5)

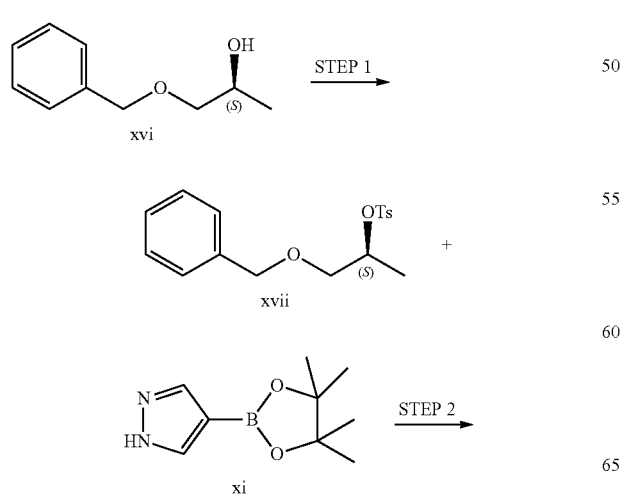

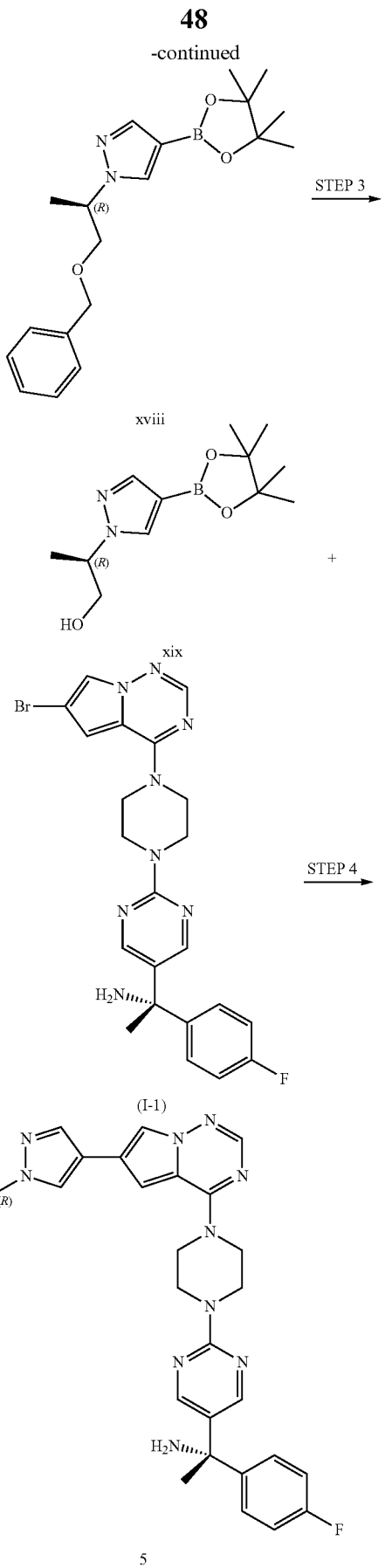

Step 1: Synthesis of (S)-1-(benzyloxy)propan-2-yl 4-methylbenzenesulfonate (xvii): To a solution of (S)-1-(benzyloxy)propan-2-ol (xvi)(5.0 g, 30.12 mmol) and TEA (9.17 g, 90.36 mmol) in DCM (80 mL) was added TsCl (6.30 g, 33.13 mmol). The mixture was stirred at RT for 24 h. The solution was diluted with DCM, washed with $H_2O$, and washed with brine. The organic layer was concentrated, and the residue was purified by flash column chromatography on silica gel (petroleum ether/ethyl acetate=3/1) to afford the title compound (xvii) (4.0 g, 42% yield) as a colorless oil. MS (ES+) $C_{17}H_{20}O_4S$ requires: 320, found: 338 $[M+18]^+$.

Step 2: Synthesis of (R)-1-(1-(Benzyloxy)propan-2-yl)-4-(4,4,5,5-tetramethyl-1,3,2-dioxaborolan-2-yl)-1H-pyrazole (xviii): A mixture of (S)-1-(benzyloxy)propan-2-yl4-methylbenzenesulfonate (xvii) (2.0 g, 6.25 mmol), 4-(4,4,5,5-tetramethyl-1,3,2-dioxaborolan-2-yl)-1H-pyrazole (xi) (1.22 g, 6.25 mmol) and $Cs_2CO_3$ (4.08 mg, 12.5 mmol) in NMP (12 mL) was irradiated at 110° C. by microwave for 0.5 h. After that, the solution was diluted with EA, washed with $H_2O$, and washed with brine. The organic layer was concentrated, and the residue was purified by flash column chromatography on silica gel (PE/EA=4/1) to afford the title compound (xviii) (1.6 g, yield 75% yield) as a colorless oil. MS (ES+) $C_{19}H_{27}BN_2O_3$ requires: 342, found: 343 $[M+H]^+$.

Step 3: Synthesis of (R)-2-(4-(4,4,5,5-Tetramethyl-1,3,2-dioxaborolan-2-yl)-1H-pyrazol-1-yl)propan-1-ol (xix): To a solution of (R)-1-(1-(benzyloxy)propan-2-yl)-4-(4,4,5,5-tetramethyl-1,3,2-dioxaborolan-2-yl)-1H-pyrazole (xviii) (800 mg, 2.34 mmol) in MeOH (20 mL) was added Pd/C (800 mg) and HOAc (0.2 mL), the solution was purged with $H_2$ (g) for 5 minutes then stirred at RT under $H_2$ (g) for 16 h. After that, the mixture was filtered and the filtrate was concentrated to give the title compound as a colorless oil(xix) (300 mg, 51% yield). MS (ES+) $C_{12}H_{21}BN_2O_3$ requires: 252, found: 253 $[M+H]^+$.

Step 4: Synthesis of (R)-2-(4-(4-(4-(5-((S)-1-Amino-1-(4-fluorophenyl)ethyl)pyrimidin-2-yl)piperazin-1-yl)pyrrolo[2,1-f][1,2,4]triazin-6-yl)-1H-pyrazol-1-yl)propan-1-ol (5): A mixture of ((R)-2-(4-(4,4,5,5-tetramethyl-1,3,2-dioxaborolan-2-yl)-1H-pyrazol-1-yl)propan-1-ol (xix) (150 mg, 595 mol), I-1 (295 mg, 595 mol), Pd(dppf)Cl$_2$ (49 mg, 60 μmol) and $K_2CO_3$ (250 mg, 1.79 mmol) in DMF/$H_2O$ (4 mL/1 mL) was purged with $N_2$ (g) for 10 mins and stirred at 70° C. for 16 h under $N_2$ (g). The mixture extracted with EtOAc, and the combined organic extracts were concentrated. The residue was purified by flash column chromatography on silica gel (DCM/MeOH=10/1). The resulting material was further purified by Prep-HPLC (Mobile phase: A=$H_2O$ (0.1% $NH_4HCO_3$), B=acetonitrile; Gradient: B=15%-95% in 18 min; Column: Xtimate™ 10 um 150A 21.2×250 mm) followed by lyophilization to afford the title compound (5) (148.1 mg, 46% yield) as a white solid. MS (ES+) $C_{28}H_{31}FN_{10}O$ requires: 542, found: 543 $[M+H]^+$.
$^1$H-NMR (400 MHz, 6d-DMSO) δ ppm 8.41 (s, 2H), 8.11 (s, 1H), 8.00 (s, 1H), 7.87 (s, 1H), 7.83 (s, 1H), 7.48-7.44 (m, 2H), 7.25 (s, 1H), 7.14-7.08 (m, 2H), 4.98 (t, 1H, J=5.2 Hz), 4.36-4.32 (m, 1H), 4.10-4.08 (m, 4H), 3.92-3.90 (m, 4H), 3.69-3.61 (m, 2H), 2.45 (s, 2H), 1.73 (s, 3H), 1.41 (d, 3H, J=6.8 Hz).

Example 6: (S)-2-(4-(4-(4-(5-((S)-1-amino-1-(4-fluorophenyl)ethyl)pyrimidin-2-yl)piperazin-1-yl) pyrrolo[2,1-f][1,2,4]triazin-6-yl)-1H-pyrazol-1-yl) propan-1-ol (6)

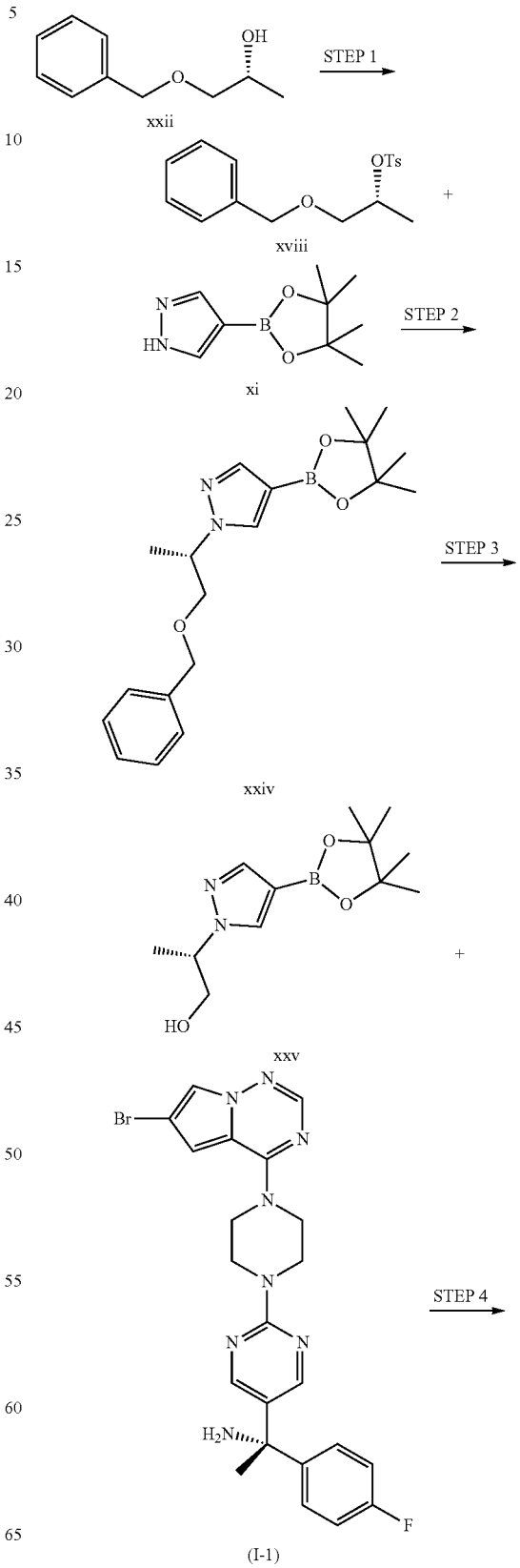

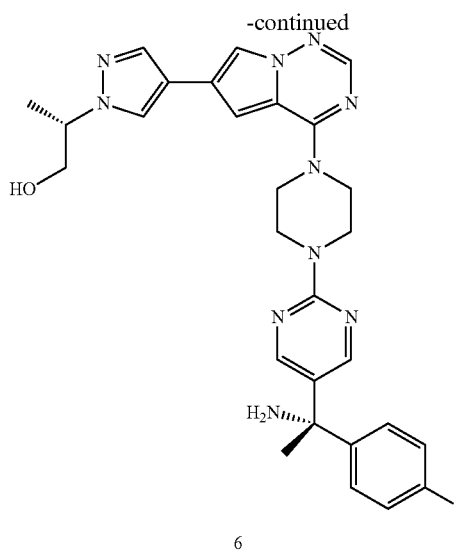

6

Step 1: Synthesis of (R)-1-(benzyloxy)propan-2-yl 4-methylbenzenesulfonate (xxiii): To a solution of (R)-1-(benzyloxy)propan-2-ol (xxii) (3.0 g, 18 mmol) and TEA (5.48 g, 54.2 mmol) in DCM (30 mL) was added TsCl (4.13 g, 21.7 mmol). The resulting mixture was stirred at 25° C. for 16 h. The mixture was then concentrated in vacuo, and the residue was purified by purified by flash column chromatography on silica gel (petroleum ether/ethyl acetate=10/1) to afford the title compound (xxiii) (2.30 g, 39% yield) as a yellow oil. MS (ES+) $C_{17}H_{20}O_4S$ requires: 320, found: 338 [M+18]+.

Step 2: Synthesis of (5)-1-(1-(Benzyloxy)propan-2-yl)-4-(4,4,5,5-tetramethyl-1,3,2-dioxaborolan-2-yl)-1H-pyrazole (xxiv): A mixture of (R)-1-(benzyloxy)propan-2-yl4-methylbenzenesulfonate (xxiii) (2.20 g, 6.87 mmol), 4-(4,4,5,5-tetramethyl-1,3,2-dioxaborolan-2-yl)-1H-pyrazole (xi) (2.00 g, 10.3 mmol) and $Cs_2CO_3$ (2.24 g, 6.87 mmol) in NMP (50 mL) was stirred at 110° C. by in the microwave for 16 h. After that, the solution was diluted with EA, washed with $H_2O$ and brine, and concentrated. The residue was purified by flash column chromatography on silica gel (petroleum ether/ethyl acetate=5/1 to 4/1) to afford the title compound (xxiv) (1.80 g, 39% yield) as a yellow oil. MS (ES+) $C_{19}H_{27}BN_2O_3$ requires: 342, found: 343[M+H]+.

Step 3: Synthesis of (S)-2-(4-(4,4,5,5-Tetramethyl-1,3,2-dioxaborolan-2-yl)-1H-pyrazol-1-yl)propan-1-ol (xxv): A mixture of (S)-1-(1-(benzyloxy)propan-2-yl)-4-(4,4,5,5-tetramethyl-1,3,2-dioxaborolan-2-yl)-1H-pyrazole (xxiv) (0.90 g, 2.6 mmol) in MeOH (20 mL) was added Pd/C (800 mg) and HOAc (0.2 mL). The resulting mixture was purged with $H_2$ (g) for 5 min then stirred at RT under $H_2$ (g) for 16 h. After that, the mixture was filtered and concentrated to afford the title compound (xxv) as a yellow oil (500 mg, 75% yield). MS (ES+) $C_{12}H_{21}BN_2O_3$ requires: 252, found: 253 [M+H]+.

Step 4: Synthesis of (S)-2-(4-(4-(4-(5-((S)-1-Amino-1-(4-fluorophenyl)ethyl)pyrimidin-2-yl)piperazin-1-yl)pyrrolo[2,1-f][1,2,4]triazin-6-yl)-1H-pyrazol-1-yl)propan-1-ol (6): A mixture of (S)-2-(4-(4,4,5,5-tetramethyl-1,3,2-dioxaborolan-2-yl)-1H-pyrazol-1-yl)propan-1-ol (xxv) (98 mg, 392 µmol), I-1 (130 mg, 261 µmol), $K_2CO_3$ (200 mg, 227 µmol) and $Pd(dppf)Cl_2$ (20 mg, 27 µmol) in $DMF/H_2O$ (5 mL/1 ml) was stirred at 70° C. under $N_2$ (g) for 4 h. After that, the solution was diluted with EA, washed with $H_2O$ and brine, and concentrated. The residue was purified by Prep-HPLC (Mobile phase: A=$H_2O$ (0.1% NH4HCO3), B=acetonitrile; Gradient: B=15%-95% in 18 min; Column: Xtimate™ 10 um 150A 21.2×250 mm) followed by lyophilization to afford the title compound (6) (40.7 mg, 28% yield) as a white solid. MS (ES+) $C_{28}H_{31}FN_{10}O$ requires: 542, found: 543 [M+H]+. 1H-NMR (400 MHz, 6d-DMSO) δ ppm 8.41 (s, 2H), 8.10 (s, 1H), 7.99 (s, 1H), 7.87 (s, 1H), 7.83 (s, 1H), 7.47 (dd, 2H, J=8.8, 5.6 Hz), 7.24 (s, 1H), 7.11 (t, 2H, J=8.8 Hz), 4.96 (t, 1H, J=5.6 Hz), 4.38-4.35 (m, 1H), 4.11-4.08 (m, 4H), 3.92-3.90 (m, 4H), 3.70-3.60 (m, 2H), 2.43 (s, 1H), 1.73 (s, 3H), 1.41 (d, 3H, J=6.8 Hz).

Example 7: (S)-1-(4-Fluorophenyl)-1-(2-(4-(6-(1-(oxetan-3-yl)-1H-pyrazol-4-yl)pyrrolo[2,1-f][1,2,4]triazin-4-yl)piperazin-1-yl)pyrimidin-5-yl)ethan-1-amine (7)

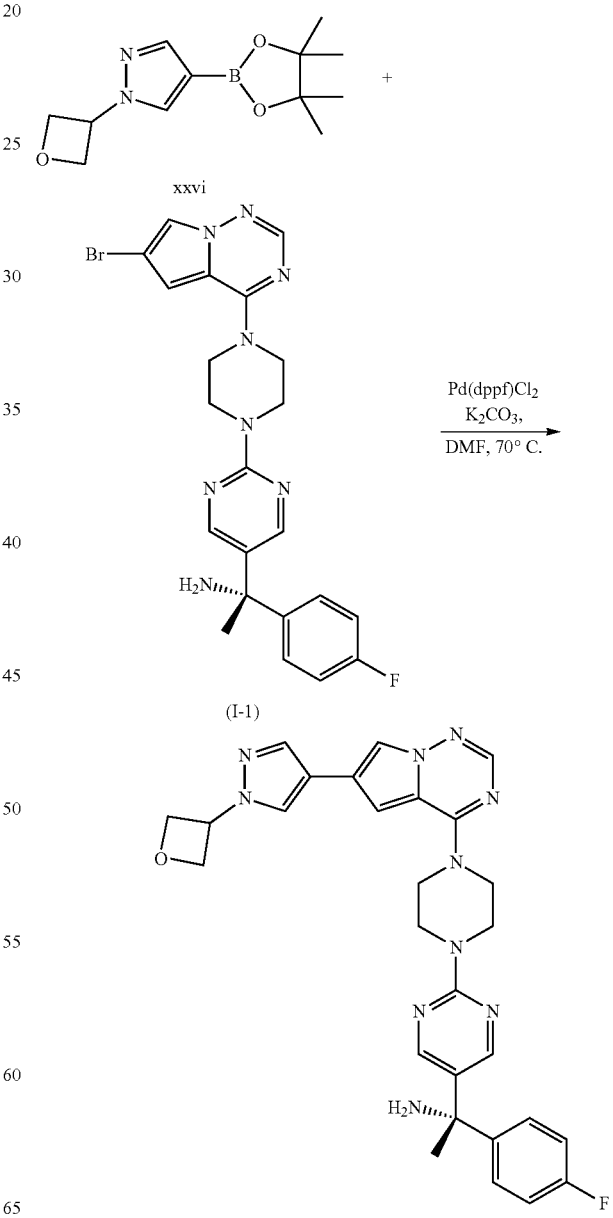

A mixture of 1-(oxetan-3-yl)-4-(4,4,5,5-tetramethyl-1,3,2-dioxaborolan-2-yl)-1H-pyrazole(xxvi) (600 mg, 2.4 mmol), I-1 (1.19 g, 2.4 mmol), Pd(dppf)Cl₂ (391 mg, 0.48 mmol) and K₂CO₃ (994 mg, 7.2 mmol) in DMF/H₂O (16 mL/4 mL) was purged with N₂ for 10 min and stirred at 70° C. for 3 h under N₂ (g). After that, the solution was diluted with EA, washed with H₂O and brine, and concentrated. The mixture was purified by flash column chromatography on silica gel (DCM/MeOH=10/1). The resulting material was purified further by Prep-HPLC (Mobile phase: A=H₂O (0.1% NH₄HCO₃), B=acetonitrile; Gradient: B=15%-95% in 18 min; Column: Xtimate™ 10 um 150A 21.2×250 mm) followed by lyophilization to afford the title compound (7) (236.3 mg, 18% yield) as a white solid. MS (ES+) $C_{28}H_{29}FN_{10}O$ requires: 540, found: 541 [M+H]⁺. ¹H-NMR (400 MHz, 6d-DMSO) δ ppm 8.41 (s, 2H), 8.32 (s, 1H), 8.03 (d, 1H, J=1.6 Hz), 7.99 (s, 1H), 7.88 (s, 1H), 7.52-7.44 (m, 2H), 7.29 (d, 1H, J=1.6 Hz), 7.16-7.07 (m, 2H), 5.64-5.52 (m, 1H), 4.99-4.94 (m, 2H), 4.93-4.89 (m, 2H), 4.12-4.06 (m, 4H), 3.97-3.87 (m, 4H), 2.50 (br. s., 2H), 1.74 (s, 3H).

Example 8: (S)-1-(4-fluorophenyl)-1-(2-(4-(6-(1-(oxetan-3-ylmethyl)-1H-pyrazol-4-yl)pyrrolo[2,1-f][1,2,4]triazin-4-yl)piperazin-1-yl)pyrimidin-5-yl)ethan-1-amine (8)

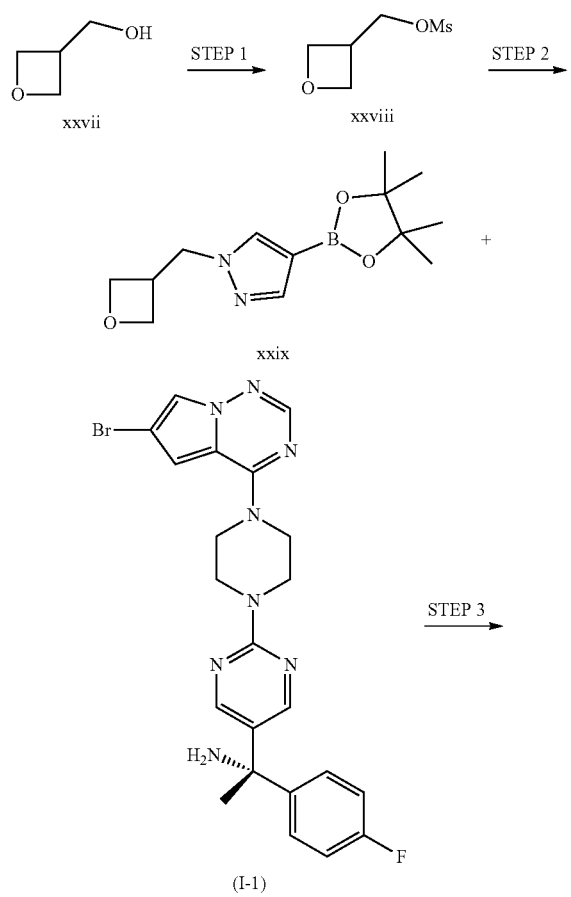

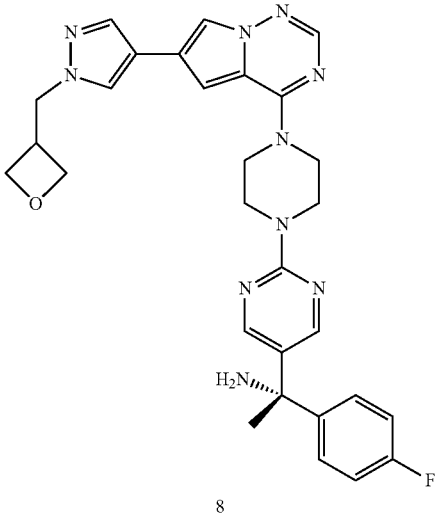

Step 1: Synthesis of oxetan-3-ylmethyl methanesulfonate (xxviii): To a solution of oxetan-3-ylmethanol (xxvii) (300 mg, 3.40 mmol) and TEA (1.03 g, 10.2 mmol) in DCM (10 mL) was added MsCl (429 mg, 3.75 mmol) at 0° C. The reaction was stirred at RT for 3 h, then diluted with DCM, washed with saturated Na₂CO₃ solution, and dried with anhydrous Na₂SO₄. The solvent was evaporated in vacuo to afford the title compound (xxviii) (280 mg, 49% yield) as a yellow oil.

Step 2: Synthesis of 1-(oxetan-3-ylmethyl)-4-(4,4,5,5-tetramethyl-1,3,2-dioxaborolan-2-yl)-1H-pyrazole (xxix): A mixture of 4-(4,4,5,5-tetramethyl-1,3,2-dioxaborolan-2-yl)-1H-pyrazole (xi) (280 mg, 1.44 mmol), oxetan-3-ylmethyl methanesulfonate (xxviii) (275 mg, 1.66 mmol) and Cs₂CO₃ (1.41 g, 4.33 mmol) in DMF (20 mL) was stirred at 70° C. for 4 h, then diluted with DCM and washed with brine. The organic layer was evaporated in vacuo. The residue was purified by flash column chromatography on silica gel (petroleum ether/ethyl acetate=10/1) to afford the title compound (xxix) (320 mg, 71% yield). MS (ES+) $C_{13}H_{21}BN_2O_3$ requires: 264, found: 265 [M+H]⁺.

Step 3: Synthesis of (S)-1-(4-fluorophenyl)-1-(2-(4-(6-(1-(oxetan-3-ylmethyl)-1H-pyrazol-4-yl)pyrrolo[2,1-f][1,2,4]triazin-4-yl)piperazin-1-yl)pyrimidin-5-yl)ethan-1-amine (8): A mixture of I-1 (300 mg, 392 µmol), 1-(oxetan-3-ylmethyl)-4-(4,4,5,5-tetramethyl-1,3,2-dioxaborolan-2-yl)-1H-pyrazole (xxix) (239 mg, 904 µmol), K₂CO₃ (250 mg, 1.81 mmol) and Pd(dppf)Cl₂ (30 mg, 41 µmol) in DMF/H₂O (10 mL/2 ml) was stirred at 70° C. under N₂ (g) for 4 h. After that, the solution was diluted with EA, washed with H₂O and brine, and concentrated. The residue was purified by Prep-HPLC (Mobile phase: A=H₂O (0.1% NH₄HCO₃), B=acetonitrile; Gradient: B=15%-95% in 18 min; Column: Xtimate™ 10 um 150A 21.2×250 mm) followed by lyophilization to afford the title compound (8) (40.2 mg, yield 12%) as a white solid. MS (ES+) $C_{29}H_{31}FN_{10}O$ requires: 554, found: 555 [M+H]⁺. ¹H-NMR (400 MHz, 6d-DMSO) δ ppm 8.41 (s, 2H), 8.09 (s, 1H), 7.98 (s, 1H), 7.87 (s, 1H), 7.84 (s, 1H), 7.47 (dd, 2H, J=8.8, 5.6 Hz), 7.22 (s, 1H), 7.11 (t, 2H, J=8.8 Hz), 4.69-4.65 (m, 2H), 4.45-4.41 (m, 4H), 4.10-4.08 (m, 4H), 3.92-3.89 (m, 4H), 3.46-3.41 (m, 1H), 2.45 (s, 2H), 1.73 (s, 3H).

Example 9: (S)-1-(4-(4-(4-(5-((S)-1-Amino-1-(4-fluorophenyl)ethyl-pyrimidin-2-yl}-piperazin-1-yl)-pyrrolo[2,1-f][1,2,4]triazin-6-yl]-pyrazol-1-yl}-propan-2-ol (9)

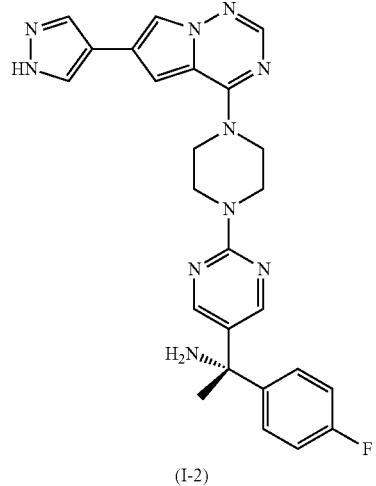

(I-2)

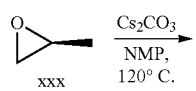

9

A mixture of I-2 (220 mg, 455 μmol), (S)-2-methyloxirane (xxx) (79 mg, 1.37 mmol) and $Cs_2CO_3$ (445 mg, 1.37 mmol) in NMP (2 mL). The mixture was irradiated at 120° C. by microwave for 1 h. After that, the solution was diluted with EA, washed with $H_2O$ and brine, and concentrated. The residue was purified by Prep-HPLC (Mobile phase: A=$H_2O$ (0.1% NH4HCO3), B=acetonitrile; Gradient: B=15%-95% in 18 min; Column: Xtimate 10 um 150A 21.2×250 mm) followed by lyophilization to afford the title compound (9) (108 mg, 44% yield) as a white solid. MS (ES+) $C_{28}H_{31}FN_{10}O$ requires: 542, found: 543 [M+H]$^+$. $^1$H-NMR (400 MHz, 6d-DMSO) δ ppm 8.41 (s, 2H), 8.05 (s, 1H), 8.00 (s, 1H), 7.87 (s, 1H), 7.83 (s, 1H), 7.48-7.44 (m, 2H), 7.25 (s, 1H), 7.14-7.08 (m, 2H), 4.96 (d, 1H, J=4.4 Hz), 4.10-4.08 (m, 4H), 4.02-3.98 (m, 3H), 3.92-3.90 (m, 4H), 2.44 (s, 2H), 1.73 (s, 3H), 1.06 (d, 3H, J=5.6 Hz).

Example 10: cis-3-(4-(4-(4-(5-((S)-1-Amino-1-(4-fluorophenyl)ethyl)pyrimidin-2-yl)piperazin-1-yl)pyrrolo[2,1-f][1,2,4]triazin-6-yl)-1H-pyrazol-1-yl) cyclobutanol (10)

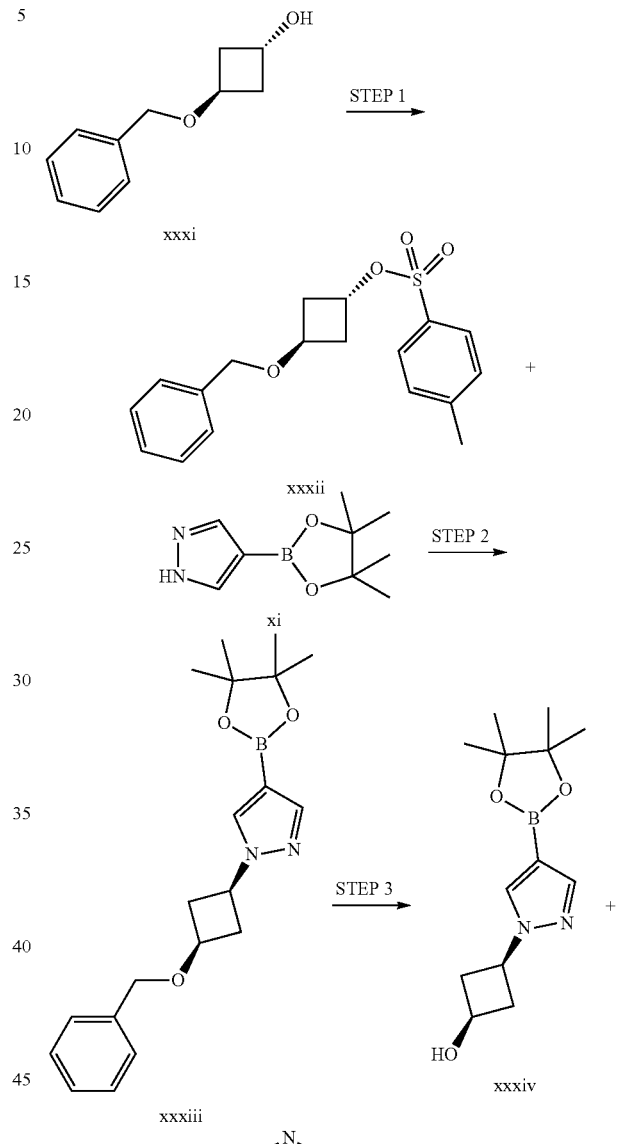

-continued

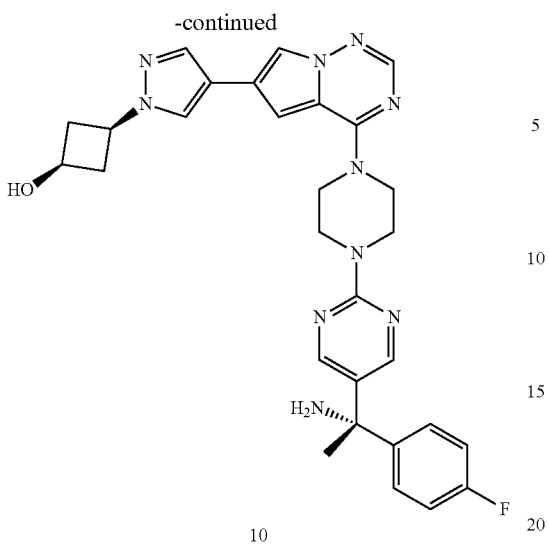

10

Step 1: Synthesis of trans-3-(benzyloxy)cyclobutyl 4-methylbenzenesulfonate (xxxii): To a solution of trans-3-(benzyloxy)cyclobutanol (xxxi) (300 mg, 1.7 mmol) in DCM (20 mL) was added TsCl (389 mg, 2.0 mmol) and TEA (343 mg, 3.4 mmol). The mixture was stirred at RT for 16 h. The solution was diluted with DCM, washed with $H_2O$ and brine, then concentrated. The residue was purified by flash column chromatography on silica gel (PE/EA=5/1) to afford the title compound (xxxii) (315 mg, 56% yield) as a colorless oil. MS (ES+) $C_{18}H_{20}O_4S$ requires: 332, found: 350 $[M+18]^+$.

Step 2: Synthesis of cis-3-(benzyloxy)cyclobutyl)-4-(4,4,5,5-tetramethyl-1,3,2-dioxaborolan-2-yl)-1H-pyrazole (xxxiii): A mixture of trans-3-(benzyloxy)cyclobutyl 4-methylbenzenesulfonate (xxxii) (315 mg, 0.95 mmol), 4-(4,4,5,5-tetramethyl-1,3,2-dioxaborolan-2-yl)-1H-pyrazole (xi) (185 mg, 0.95 mmol), and $Cs_2CO_3$ (619 mg, 1.9 mmol) in NMP (5 mL) was irradiated at 110° C. by microwave for 0.5 h. After that, the solution was diluted with EA and washed with $H_2O$ and brine. The organic layer was concentrated in vacuo, and the residue was purified by flash column chromatography on silica gel (PE/EA=4/1) to afford the title compound (xxxiii) (190 mg, 56% yield) as a colorless oil. MS (ES+) $C_{20}H_{27}BN_2O_3$ requires: 354, found: 355 $[M+H]^+$.

Step 3: Synthesis of cis-3-(4-(4,4,5,5-tetramethyl-1,3,2-dioxaborolan-2-yl)-1H-pyrazol-1-yl)cyclobutanol(xxxiv): To a solution of cis-3-(benzyloxy)cyclobutyl)-4-(4,4,5,5-tetramethyl-1,3,2-dioxaborolan-2-yl)-1H-pyrazole (xxxiii) (190 mg, 0.54 mmol) in MeOH (5 mL) was added Pd/C (200 mg) and HOAc (5 drops), the solution was purged with $H_2$ (g) for 5 min and stirred at RT under $H_2$ (g) for 16 h. The mixture was filtered, and the filtrate was evaporated to dryness in vacuo to afford the title compound (xxxiv) as a colorless oil (85 mg, 60% yield). MS (ES+) $C_{13}H_{21}BN_2O_3$ requires: 264, found: 265$[M+H]^+$.

Step 4: Synthesis of (cis-3-(4-(4-(4-(5-((S)-1-amino-1-(4-fluorophenyl)ethyl)pyrimidin-2-yl)piperazin-1-yl)pyrrolo[2,1-f][1,2,4]triazin-6-yl)-1H-pyrazol-1-yl)cyclobutanol (10): A mixture of cis-3-(4-(4,4,5,5-tetramethyl-1,3,2-dioxaborolan-2-yl)-1H-pyrazol-1-yl)cyclobutanol (xxxiv) (55 mg, 0.21 mmol), I-1 (104 mg, 0.21 mmol), Pd(dppf)Cl$_2$ (18 mg, 0.021 µmol) and K$_2$CO$_3$ (87 mg, 0.63) in DMF/H$_2$O (4 mL/1 mL) was purged with N$_2$ for 10 min and stirred at 70° C. for 16 h under N$_2$ (g). After that, the solution was diluted with EA, washed with H$_2$O and brine, and concentrated. The residue was purified directly by flash column chromatography (DCM/MeOH=8/1). The resulting material was purified further by Prep-HPLC ((Mobile phase: A=H$_2$O (0.1% NH$_4$HCO$_3$), B=acetonitrile; Gradient: B=15%-95% in 18 min; Column: Xtimate™ 10 um 150A 21.2×250 mm)) followed by lyophilization to afford the title compound (10) (14.6 mg, 13% yield) as a white solid. MS (ES+) $C_{29}H_{31}FN_{10}O$ requires: 554, found: 555 $[M+H]^+$. $^1$H-NMR (400 MHz, 6d-DMSO) δ ppm 8.41 (s, 2H), 8.17 (s, 1H), 8.00 (s, 1H), 7.87-7.86 (m, 2H), 7.49-7.45 (m, 2H), 7.26 (s, 1H), 7.19-7.13 (m, 2H), 5.33 (d, 1H, J=6.4 Hz), 4.38-4.31 (m, 1H), 4.13-4.06 (m, 4H), 3.99-3.96 (m, 1H), 3.94-3.88 (m, 4H), 2.79-2.71 (m, 2H), 2.34-2.31 (m, 2H), 1.73 (s, 3H).

Example 11: trans-3-{4-[4-(4-{5-[1-Amino-1-(4-fluoro-phenyl)-ethyl]-pyrimidin-2-yl}-piperazin-1-yl)-pyrrolo[2,1-f][1,2,4]triazin-6-yl]-pyrazol-1-yl}-cyclobutanol (11)

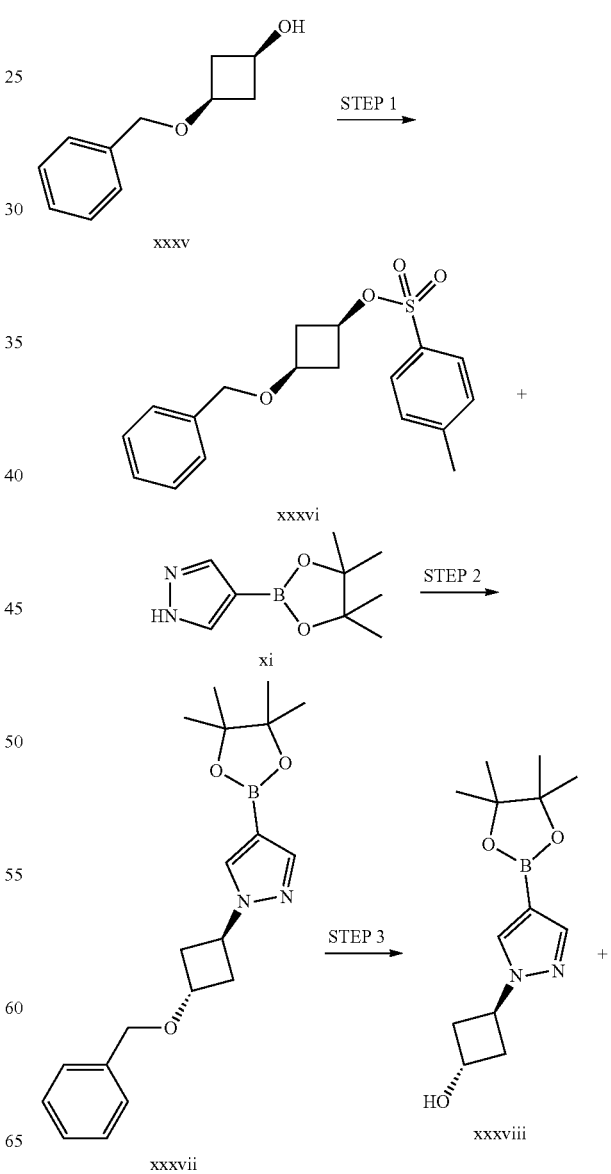

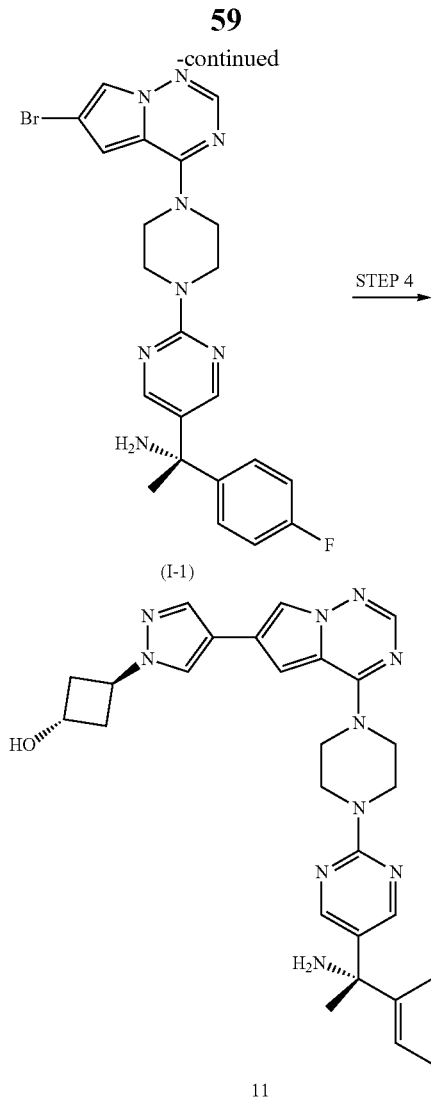

Step 1: Synthesis of cis-toluene-4-sulfonic acid 3-benzyloxy-cyclobutyl ester (xxxvi): To a solution of cis-3-benzyloxy-cyclobutanol (xxxv) (500 mg, 2.81 mmol) and TEA (851 mg, 8.43 mmol) in DCM (10 mL) was added 4-methyl-benzenesulfonyl chloride (640 mg, 3.37 mmol), and the resulting mixture was stirred at RT for 16 h. The mixture was diluted with brine and extracted with DCM. The organic extract was concentrated. The residue was purified directly by flash column chromatography on silica gel (PE/EA=11/1) to afford the title compound (xxxvi) (490 mg, 53% yield) as a yellow solid. MS (ES+) $C_{18}H_{20}O_4S$ requires: 332, found: 350 $[M+18]^+$.

Step 2: Synthesis of trans-1-(3-benzyloxy-cyclobutyl)-4-(4,4,5,5-tetramethyl-[1,3,2]dioxaborolan-2-yl)-1H-pyrazole (xxxvii): A mixture of cis-toluene-4-sulfonic acid 3-benzyloxy-cyclobutyl ester (xxxvi) (500 mg, 1.51 mmol), 4-(4,4,5,5-tetramethyl-[1,3,2]dioxaborolan-2-yl)-1H-pyrazole (xi) (430 mg, 2.22 mmol), and $Cs_2CO_3$ (1.47 g, 4.51 mmol) in NMP (15 mL) was irradiated by microwave at 120° C. for 2 h. After that, the solution was diluted with EA, washed with $H_2O$ and brine, and concentrated. The residue was purified by flash column chromatography on silica gel (PE/EA=1/1) to afford the title compound (xxxvii) (227 mg, 42% yield) as a yellow solid. MS (ES+) $C_{20}H_{27}BN_2O_3$ requires: 354, found: 355 $[M+H]^+$.

Step 3: Synthesis of trans-3-[4-(4,4,5,5-tetramethyl-[1,3,2]dioxaborolan-2-yl)-pyrazol-1-yl]-cyclobutanol(xxxviii):
To a solution of trans-1-(3-benzyloxy-cyclobutyl)-4-(4,4,5,5-tetramethyl-[1,3,2]dioxaborolan-2-yl)-1H-pyrazole (xxxvii) (420 mg, 1.18 mmol) in MeOH (10 mL) was added Pd/C (200 mg) and concentrated HCl (0.5 mL). The reaction mixture was stirred under $H_2$ (g) at RT for 16 h. The mixture was filtered, and the filtrate was concentrated to afford the title compound (xxxviii) (250 mg, 80% yield) as a solid. MS (ES+) $C_{13}H_{21}BN_2O_3$ requires: 264, found: 265 $[M+H]^+$.

Step 4: Synthesis of trans-3-{4-[4-(4-{5-[1-amino-1-(4-fluoro-phenyl)-ethyl]-pyrimidin-2-yl}-piperazin-1-yl)-pyrrolo[2,1-f][1,2,4]triazin-6-yl]-pyrazol-1-yl}-cyclobutanol (11): A mixture of trans-3-[4-(4,4,5,5-tetramethyl-[1,3,2]dioxaborolan-2-yl)-pyrazol-1-yl]-cyclobutanol(xxxviii) (200 mg, 0.76 mmol), I-1 (376 mg, 0.76 mmol), $Pd(dppf)Cl_2$ (61.8 mg, 0.076 mmol) and $K_2CO_3$ (313 mg, 2.27 mmol) in dioxane/$H_2O$ (4 mL/1 mL) was purged with $N_2$ (g) for 10 mins and stirred at 70° C. for 4 h under $N_2$ (g). After that, the solution was diluted with EA, washed with $H_2O$ and brine, and concentrated. The residue was purified by flash chromatography on silica gel. The resulting material was purified further by Prep-HPLC (Mobile phase: A=$H_2O$ (0.1% $NH_4HCO_3$), B=acetonitrile; Gradient: B=15%-95% in 18 min; Column: Xtimate™ 10 um 150A 21.2×250 mm) followed by lyophilization to afford the title compound (11) (27.2 mg, 6% yield) as a white solid. MS (ES+) $C_{29}H_{31}FN_{10}O$ requires: 554, found: 555 $[M+H]^+$. $^1$H-NMR (400 MHz, 6d-DMSO) δ ppm 8.41 (s, 2H), 8.18 (s, 1H), 7.99 (d, 1H, J=1.2 Hz), 7.87-7.85 (m, 2H), 7.49-7.45 (m, 2H), 7.24 (s, 1H), 7.15-7.08 (m, 2H), 5.24 (d, 1H, J=5.2 Hz), 4.92-4.89 (m, 1H), 4.50-4.43 (m, 1H), 4.17-4.10 (m, 4H), 3.96-3.90 (m, 4H), 2.67-2.61 (m, 2H), 2.44 (s, 2H), 2.42-2.37 (m, 2H), 1.73 (s, 3H).

Example 12: (S)-1-((4-(4-(4-(5-(1-Amino-1-(4-fluorophenyl)ethyl)pyrimidin-2-yl)piperazin-1-yl)pyrrolo[2,1-f][1,2,4]triazin-6-yl)-1H-pyrazol-1-yl)methyl)cyclopropan-1-ol (12)

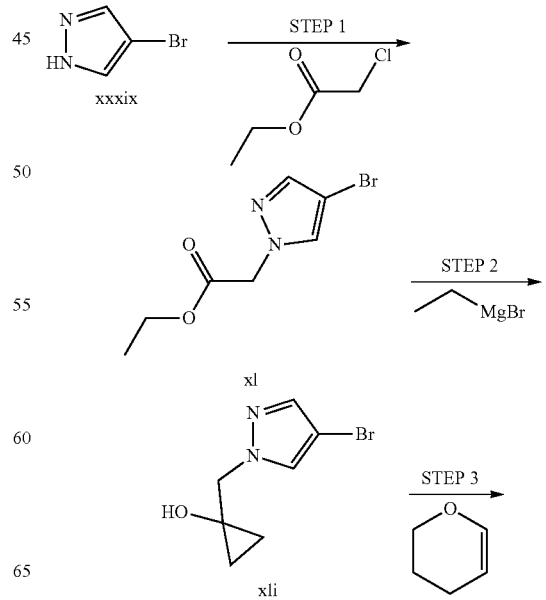

-continued

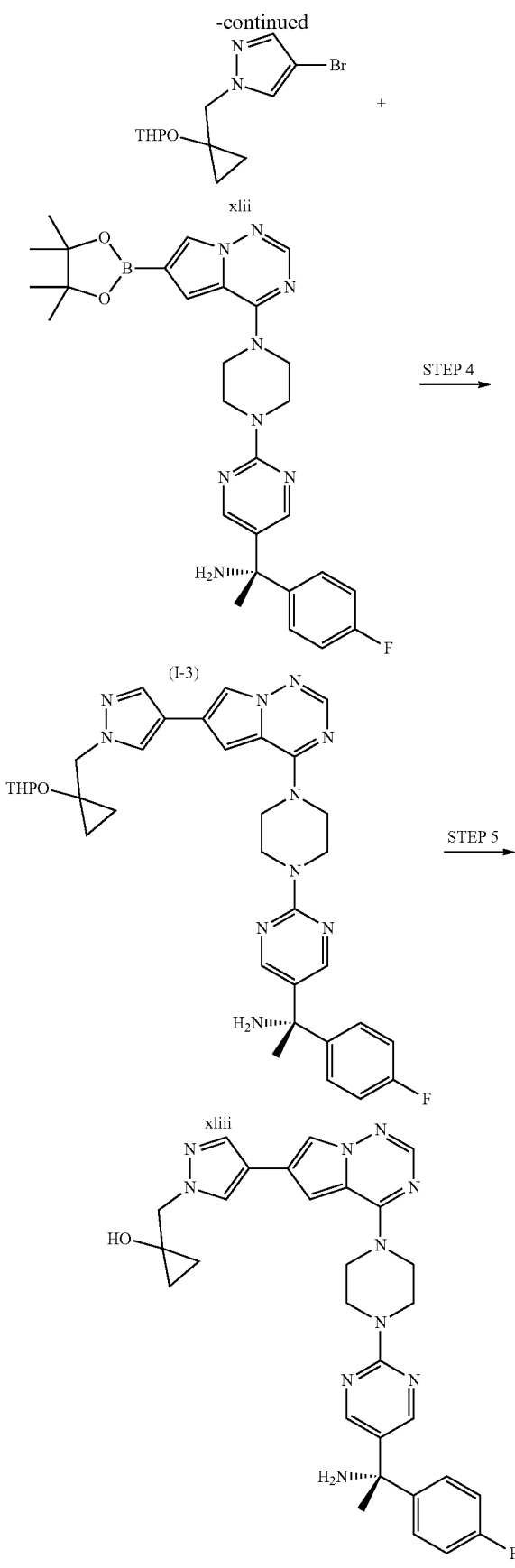

Step 1: Synthesis of ethyl 2-(4-bromo-1H-pyrazol-1-yl) acetate (xl): A mixture of 4-bromo-1H-pyrazole (xxxix) (8.0 g, 55 mmol) and K$_2$CO$_3$ (15.2 g, 110 mmol) in ethyl 2-chloroacetate (25 mL) was stirred at 80° C. for 15 h. The reaction mixture was cooled, diluted with EA, and washed with H$_2$O. The organic layer was evaporated, and the residue was purified by chromatography on silica gel (petroleum ether/ethyl acetate=5:1) to give the title compound (xl) (8.5 g, 66% yield) as a pale yellow oil. MS (ES+) C$_7$H$_9$BrN$_2$O$_2$ requires: 232, found: 233 [M+H]$^+$.

Step 2: Synthesis of ethyl 1-((4-bromo-1H-pyrazol-1-yl) methyl)cyclopropan-1-ol (xli): To a solution of ethyl 2-(4-bromo-1H-pyrazol-1-yl)acetate (xl) (7.0 g, 30 mmol) and titanium tetraisopropanolate (4.26 g, 15 mmol) in anhydrous THF (60 mL) was added a solution of ethyl magnesium bromide (3 M in hexane, 30 mL, 90 mmol) dropwise at 60° C. over 2 h. After stirring at same temperature for 2 h, the reaction mixture was diluted with EA and washed sequentially with 1N aq. HCl and H$_2$O. The organic layer was evaporated, and the residue was purified by chromatography on silica gel (petroleum ether/ethyl acetate=20:1 to 3:1) to give the title compound (xli) (1.3 g, 20% yield) as a yellow solid. MS (ES+) C$_7$H$_9$BrN$_2$O requires: 216, found: 217 [M+H]$^+$.

Step 3: Synthesis of 4-bromo-1-[1-(tetrahydro-pyran-2-yloxy)-cyclopropylmethyl]-1H-pyrazole (xlii): To a solution of 1-[(4-bromo-1H-pyrazol-1-yl)methyl]cyclopropan-1-ol (xli) (300 mg, 1.38 mmol) and 3,4-dihydro-2H-pyran (348 mg, 4.14 mmol) in DCM (8 mL) was added pyridinium para-toluene sulfonate (346 mg, 1.38 mmol) at RT. The mixture was stirred for 4 h, then was diluted with brine and washed with DCM. The organic layer was concentrated, and the residue was purified by chromatography on silica gel (PE/EA=10:1) to obtain the title compound (xlii) (200 mg, 48% yield) as a white solid. MS (ES+) C$_{12}$H$_{17}$BrN$_2$O$_2$ requires: 300, found: 217 [M−THP+H]$^+$.

Step 4: Synthesis of 1-(4-fluoro-phenyl)-1-{2-[4-(6-{1-[1-(tetrahydro-pyran-2-yloxy)-cyclopropylmethyl]-1H-pyrazol-4-yl}-pyrrolo[2,1-f][1,2,4]triazin-4-yl)-piperazin-1-yl]-pyrimidin-5-yl}-ethylamine (xliii): A mixture of 4-bromo-1-{[1-(oxan-2-yloxy)cyclopropyl]methyl}-1H-pyrazole (xlii) (160 mg, 0.531 mmol), 1-3 (577 mg, 1.06 mmol), Pd(dppf)Cl$_2$ (77.5 mg, 106 μmop and Na$_2$CO$_3$ (168 mg, 1.59 mmol) in a mixture of 1,4-dioxane (3 ml), H$_2$O (1 mL) and DMF (0.5 mL) was stirred at 80° C. for 3 h under N$_2$ (g). After that, the solution was diluted with EA, washed with H$_2$O and brine, and concentrated. The residue was purified by chromatography on silica gel (ethyl acetate/methanol=4:1) to give the title compound (270 mg, 50% yield) as a brown solid. MS (ES+) C$_{34}$H$_{39}$FN$_{10}$O$_2$ requires: 621, found: 622 [M+H]$^+$.

Step 5: Synthesis of 1-{4-[4-(4-{5-[1-amino-1-(4-fluoro-phenyl)-ethyl]-pyrimidin-2-yl}-piperazin-1-yl)-pyrrolo[2,1-f][1,2,4]triazin-6-yl]-pyrazol-1-ylmethyl}-cyclopropanol (12): To a solution of 1-(4-fluoro-phenyl)-1-{2-[4-(6-{1-[1-(tetrahydro-pyran-2-yloxy)-cyclopropylmethyl]-1H-pyrazol-4-yl}-pyrrolo[2,1-f][1,2,4]triazin-4-yl)-piperazin-1-yl]-pyrimidin-5-yl}-ethylamine (xliii) (200 mg, 0.32 mmol) in MeOH (4 mL) was added p-toluenesulfonic acid (180 mg, 1.04 mmol) at RT, and the resulting mixture was stirred for 2 h. The reaction mixture was concentrated, and the residue was purified by Prep-HPLC (Mobile phase: A=H$_2$O (10 mM NH$_4$HCO$_3$ & 0.025% NH$_3$.H$_2$O), B=acetonitrile; Gradient: 51-56% B in 7 min, stop at 15 min; Column: Agela Durashell C18 (L) 21.2*250 mm, 10 μm, 150 A) followed by lyophilization to give the title compound (12) (56 mg, 31% yield) as a white solid. MS (ES+) C$_{29}$H$_{31}$FN$_{10}$O requires: 554, found: 555 [M+H]$^+$. $^1$H-NMR (400 MHz, DMSO-d6) δ ppm 8.40 (s, 2H), 8.10 (s, 1H), 8.02 (s, 1H), 7.87 (s, 1H), 7.82 (s, 1H), 7.48-7.44 (m, 2H), 7.25 (s, 1H), 7.13-7.08 (m, 2H), 5.57 (s, 1H), 4.17 (s, 2H), 4.13-4.05 (m, 4H), 3.95-3.85 (m, 4H), 1.73 (s, 3H), 0.69-0.66 (m, 4H).

Example 13: (S)-(1-(4-(4-(4-(5-(1-Amino-1-(4-fluorophenyl)ethyl)pyrimidin-2-yl)piperazin-1-yl)pyrrolo[2,1-f][1,2,4]triazin-6-yl)-1H-pyrazol-1-yl)cyclopropyl)methanol (13)

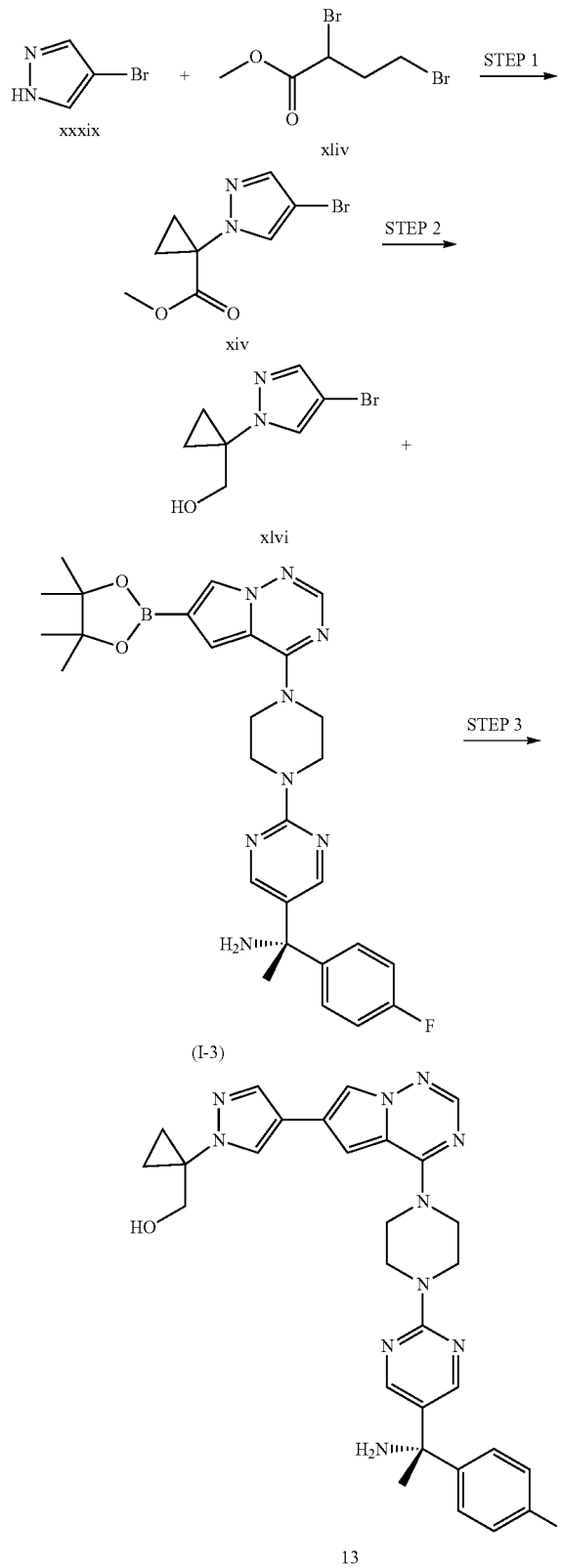

Step 1: Synthesis of methyl 1-(4-bromo-1H-pyrazol-1-yl)cyclopropanecarboxylate (xiv): To a solution of 4-bromo-1H-pyrazole (xxxix) (2.0 g, 13.70 mmol) in THF (50 mL) was added NaH (1.20 g, 30.14 mmol) at 0° C. The solution was stirred at room temperature for 1 h, then methyl 2,4-dibromobutanoate (xliv) (3.53 g, 13.70 mmol) was added to the solution. The mixture was stirred for 16 h, then diluted with EA. The organic layer was washed with $H_2O$, washed with brine, and concentrated in vacuo. The residue was purified by flash column chromatography on silica gel (petroleum ether/ethyl acetate=2/1) to afford the title compound (xiv) (570 mg, 17% yield) as a white solid. MS (ES+) $C_8H_9BrN_2O_2$ requires: 244, found: 245 $[M+H]^+$.

Step 2: Synthesis of (1-(4-bromo-1H-pyrazol-1-yl)cyclopropyl)methanol(xlvii): To a solution of methyl 1-(4-bromo-1H-pyrazol-1-yl)cyclopropanecarboxylate (xiv) (550 mg, 2.25 mmol) in MeOH (15 mL) was added $NaBH_4$ (257 mg, 6.75 mmol), and the resulting mixture was stirred at 50° C. for 36 h. The reaction mixture was diluted with DCM, washed in sequence with $H_2O$ and brine, and concentrated in vacuo. The residue was purified by flash column chromatography on silica gel (PE/EA=1/1) to afford the title compound (xlvii) (300 mg, 62% yield) as a white solid. MS (ES+) $C_7H_9BrN_2O$ requires: 216, found: 217 $[M+H]^+$.

Step 3: Synthesis of (S)-(1-(4-(4-(4-(5-(1-amino-1-(4-fluorophenyl)ethyl)pyrimidin-2-yl)piperazin-1-yl)pyrrolo[2,1-f][1,2,4]triazin-6-yl)-1H-pyrazol-1-yl)cyclopropyl)methanol (13): A mixture of (1-(4-bromo-1H-pyrazol-1-yl)cyclopropyl)methanol (xlvii) (100 mg, 463 mol), 1-3 (prepared as described in preparation 3) (380 mg, 695 mol), $Pd(t-Bu_3P)_2$ (47 mg, 93 μmol) and $Cs_2CO_3$ (452 mg, 1.39 mmol) in $THF/H_2O$ (8 mL/2 mL) was purged with $N_2$ (g) for 10 min and stirred at 80° C. for 12 h under $N_2$ (g). After that, the solution was diluted with EA, washed with $H_2O$ and brine, and concentrated. The residue was purified by flash column chromatography (DCM/MeOH=10/1). The resulting material was purified further by Prep-HPLC (Mobile phase: A=$H_2O$ (0.1% $NH_4HCO_3$), B=acetonitrile; Gradient: B=15%-95% in 18 min; Column: Xtimate™ 10 um 150A 21.2×250 mm) followed by lyophilization to afford the title compound (13) (57.3 mg, 22% yield) as a white solid. MS (ES+) $C_{29}H_{31}FN_{10}O$ requires: 554, found: 555 $[M+H]^+$. $^1$H-NMR (400 MHz, 6d-DMSO) δ ppm 8.41 (s, 2H), 8.15 (s, 1H), 8.00 (d, 1H, J=1.6 Hz), 7.87 (s, 1H), 7.83 (s, 1H), 7.48-7.44 (m, 2H), 7.27 (d, 1H, J=1.6 Hz), 7.14-7.08 (m, 2H), 5.00 (t, 1H, J=5.6 Hz), 4.10-4.08 (m, 4H), 3.92-3.90 (m, 4H), 3.66 (d, 2H, J=5.6 Hz), 2.43 (s, 2H), 1.73 (s, 3H), 1.13-1.11 (m, 2H), 1.05-1.02 (m, 2H).

Example 14: (S)-1-(4-Fluorophenyl)-1-(2-(4-(6-(1-((R)-tetrahydrofuran-3-yl)-1H-pyrazol-4-yl)pyrrolo[2,1-f][1,2,4]triazin-4-yl)piperazin-1-yl)pyrimidin-5-yl)ethanamine (14)

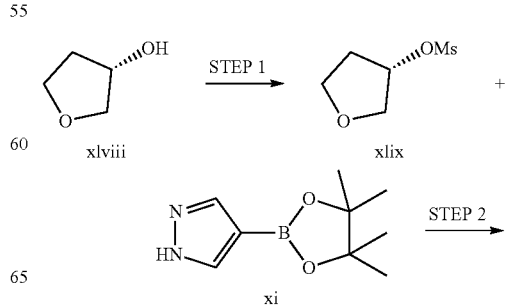

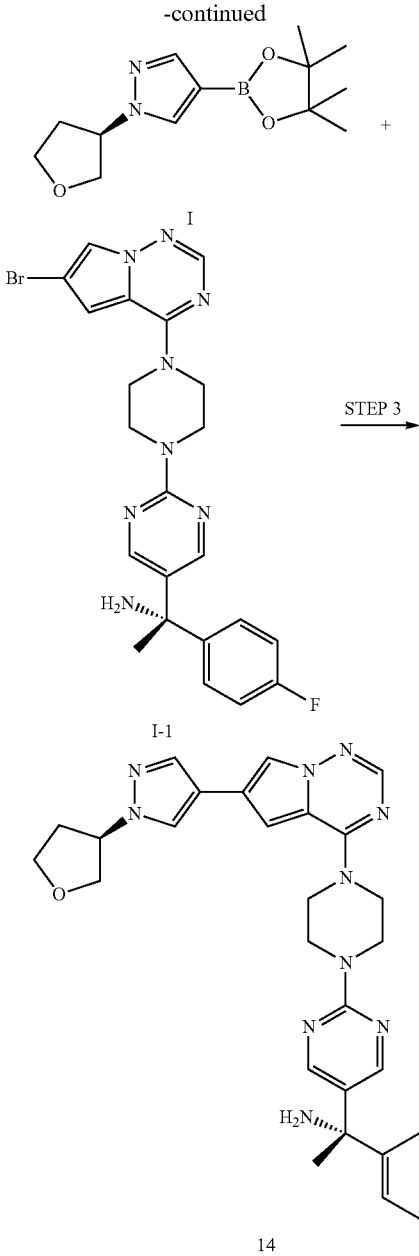

solution was diluted with EA, washed in sequence with H₂O and brine, and concentrated in vacuo. The residue was purified by flash column chromatography on silica gel (PE/EA=4/1) to afford the title compound (1) (2.3 g, 76% yield) as a colorless oil. MS (ES+) $C_{13}H_{21}BN_2O_3$ requires: 264, found: 265 [M+H]⁺.

Step 3: Synthesis of (S)-1-(4-fluorophenyl)-1-(2-(4-(6-(1-((R)-tetrahydrofuran-3-yl)-1H-pyrazol-4-yl)pyrrolo[2,1-f][1,2,4]triazin-4-yl)piperazin-1-yl)pyrimidin-5-yl)ethanamine (14): A mixture of (R)-1-(tetrahydro-furan-3-yl)-4-(4,4,5,5-tetramethyl-[1,3,2]dioxaborolan-2-yl)-1H-pyrazole (1) (80 mg, 0.3 mmol), I-1 (150 mg, 0.3 mmol), Pd(dppf)Cl₂ (50 mg, 0.06 mmol), and K₂CO₃ (125 mg, 0.9 mmol) in DMF (2 mL) and H₂O (0.5 mL) was stirred at 80° C. for 16 h under N₂ (g). After that, the solution was diluted with EA, washed with H₂O and brine, and concentrated. The residue was purified by flash column chromatography on silica gel (DCM/MeOH=16/1). The resulting material was subsequently purified by Prep-HPLC (Mobile phase: A=H₂O (0.1% NH4HCO3), B=acetonitrile; Gradient: B=15%-95% in 18 min; Column: Xtimate™ 10 um 150A 21.2×250 mm) followed by lyophilization to afford the title compound (14) (65 mg, 38% yield) as a white solid. MS (ES+) $C_{29}H_{31}FN_{10}O$ requires: 554, found: 555 [M+H]⁺. ¹H-NMR (400 MHz, 6d-DMSO) δ ppm 8.41 (s, 2H), 8.16 (s, 1H), 8.01 (s, 1H), 7.87 (s, 2H), 7.49-7.45 (m, 2H), 7.26 (s, 1H), 7.14-7.08 (m, 2H), 5.05-4.99 (m, 1H), 4.10-4.04 (m, 4H), 4.02-3.98 (m, 2H), 3.94-3.82 (m, 6H), 2.44-2.28 (m, 4H), 1.73 (s, 3H).

Example 15: (S)-1-(4-Fluorophenyl)-1-(2-(4-(6-(1-((S)-tetrahydrofuran-3-yl)-1H-pyrazol-4-yl)pyrrolo[2,1-f][1,2,4]triazin-4-yl)piperazin-1-yl)pyrimidin-5-yl)ethanamine (15)

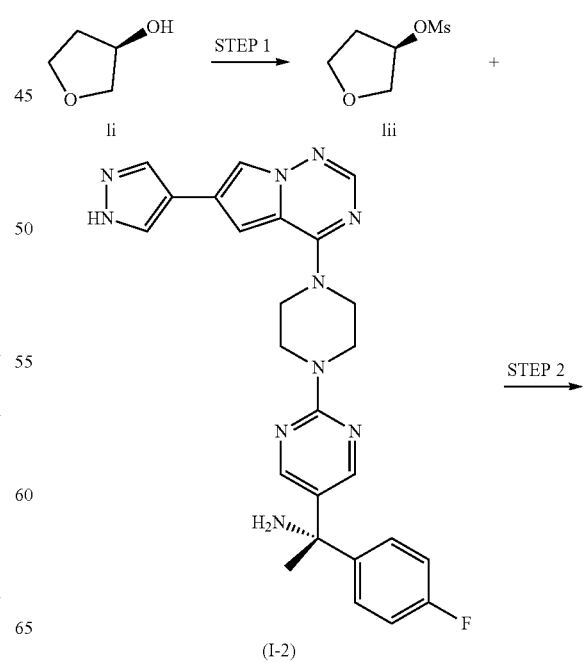

Step 1: Synthesis of (S)-tetrahydrofuran-3-yl methanesulfonate (xlix): To a solution of tetrahydro-furan-3-ol(xlviii) (2.0 g, 22.7 mmol) and TEA (4.6 g, 45.4 mmol) in DCM (20 mL) was added MsCl (4.7 g, 25.0 mmol) at RT. The mixture was stirred at room temperature for 16 h. The reaction mixture was then diluted with DCM, washed in sequence with H₂O and brine, dried over anhydrous Na₂SO₄, and concentrated to dryness to afford the title compound (xlix) (2.0 g, crude) as a yellow oil.

Step 2: Synthesis of (R)-1-(tetrahydrofuran-3-yl)-4-(4,4,5,5-tetramethyl-1,3,2-dioxaborolan-2-yl)-1H-pyrazole (1): To a solution of (S)-tetrahydrofuran-3-yl methanesulfonate (xlviii)(1.9 g, 11.4 mmol) in NMP (50 mL) was added 4-(4,4,5,5-tetramethyl-[1,3,2]dioxaborolan-2-yl)-1H-pyrazole (xi) (3.3 g, 17.2 mmol) and Cs₂CO₃ (11.2 g, 34.3 mmol) at RT. The mixture was stirred at 120° C. for 2 h. The

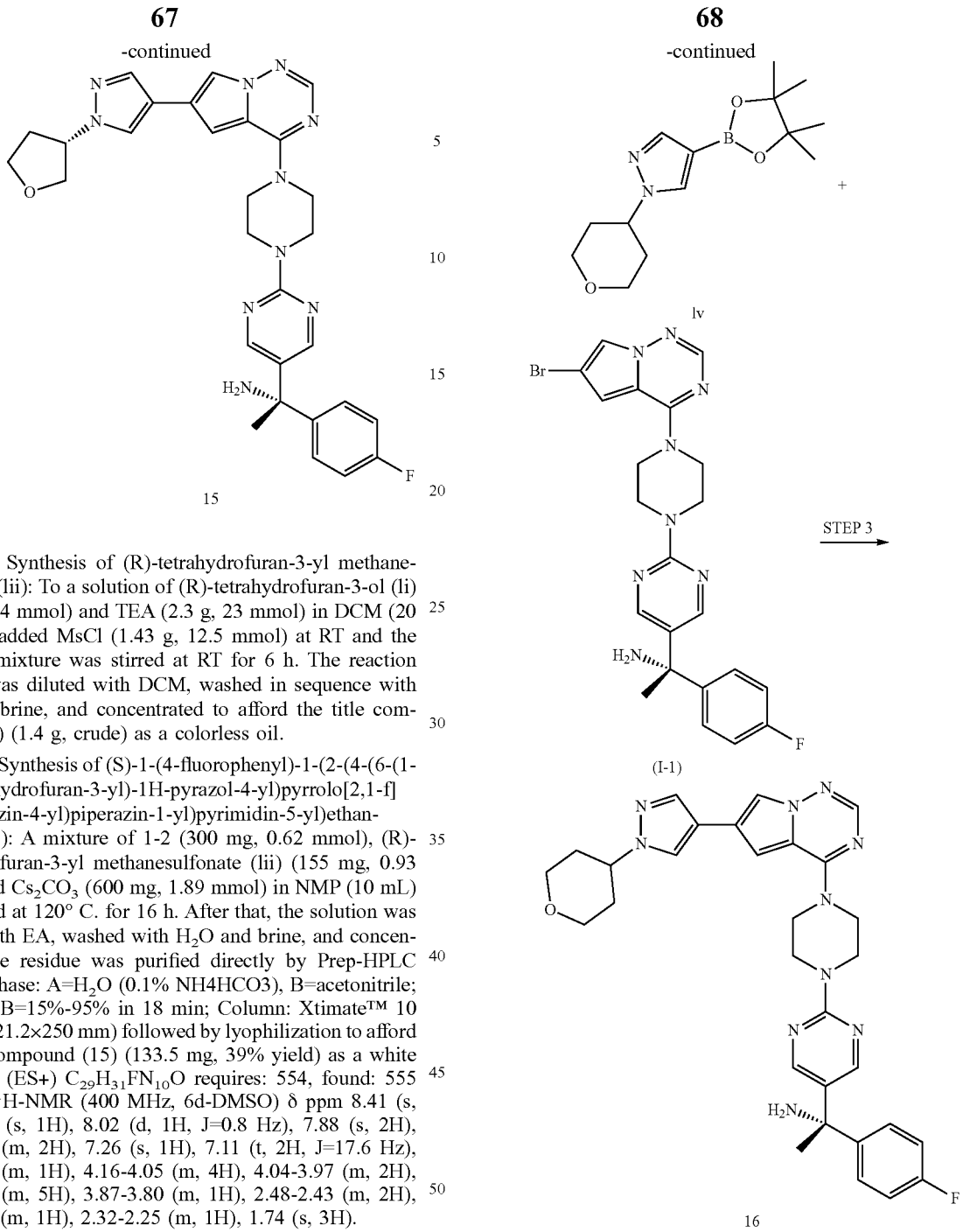

Step 1: Synthesis of (R)-tetrahydrofuran-3-yl methanesulfonate (lii): To a solution of (R)-tetrahydrofuran-3-ol (li) (1.0 g, 11.4 mmol) and TEA (2.3 g, 23 mmol) in DCM (20 mL) was added MsCl (1.43 g, 12.5 mmol) at RT and the resulting mixture was stirred at RT for 6 h. The reaction mixture was diluted with DCM, washed in sequence with $H_2O$ and brine, and concentrated to afford the title compound (lii) (1.4 g, crude) as a colorless oil.

Step 2: Synthesis of (S)-1-(4-fluorophenyl)-1-(2-(4-(6-(1-((S)-tetrahydrofuran-3-yl)-1H-pyrazol-4-yl)pyrrolo[2,1-f][1,2,4]triazin-4-yl)piperazin-1-yl)pyrimidin-5-yl)ethanamine (15): A mixture of 1-2 (300 mg, 0.62 mmol), (R)-tetrahydrofuran-3-yl methanesulfonate (lii) (155 mg, 0.93 mmol) and $Cs_2CO_3$ (600 mg, 1.89 mmol) in NMP (10 mL) was stirred at 120° C. for 16 h. After that, the solution was diluted with EA, washed with $H_2O$ and brine, and concentrated. The residue was purified directly by Prep-HPLC (Mobile phase: A=$H_2O$ (0.1% NH4HCO3), B=acetonitrile; Gradient: B=15%-95% in 18 min; Column: Xtimate™ 10 um 150A 21.2×250 mm) followed by lyophilization to afford the title compound (15) (133.5 mg, 39% yield) as a white solid. MS (ES+) $C_{29}H_{31}FN_{10}O$ requires: 554, found: 555 $[M+H]^+$. $^1$H-NMR (400 MHz, 6d-DMSO) δ ppm 8.41 (s, 2H), 8.17 (s, 1H), 8.02 (d, 1H, J=0.8 Hz), 7.88 (s, 2H), 7.52-7.44 (m, 2H), 7.26 (s, 1H), 7.11 (t, 2H, J=17.6 Hz), 5.08-4.99 (m, 1H), 4.16-4.05 (m, 4H), 4.04-3.97 (m, 2H), 3.96-3.88 (m, 5H), 3.87-3.80 (m, 1H), 2.48-2.43 (m, 2H), 2.43-2.36 (m, 1H), 2.32-2.25 (m, 1H), 1.74 (s, 3H).

Example 16: (S)-1-(4-Fluorophenyl)-1-(2-(4-(6-(1-(tetrahydro-2H-pyran-4-yl)-1H-pyrazol-4-yl)pyrrolo[2,1-f][1,2,4]triazin-4-yl)piperazin-1-yl)pyrimidin-5-yl)ethan-1-amine (16)

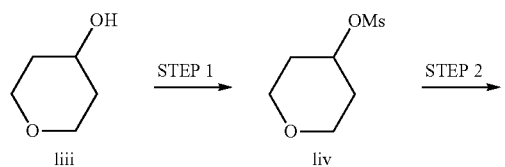

Step 1: Synthesis of tetrahydro-2H-pyran-4-yl methanesulfonate (liv): To a solution of tetrahydro-2H-pyran-4-ol (liii)(3.20 g, 31.3 mmol) and TEA (9.51 g, 94.0 mmol) in DCM (100 mL) was added MsCl (5.38 g, 47.0 mmol) at 0° C. The reaction was stirred at RT for 3 h, then diluted with DCM, washed with saturated aq. $Na_2CO_3$ solution, and dried with anhydrous $Na_2SO_4$. The solvent was removed to afford the title compound (liv) (3.2 g, crude) as a yellow oil.

Step 2: Synthesis of 1-(tetrahydro-2H-pyran-4-yl)-4-(4,4,5,5-tetramethyl-1,3,2-dioxaborolan-2-yl)-1H-pyrazole (lv): A mixture of tetrahydro-2H-pyran-4-yl methanesulfonate (liv) (3.20 g, 17.7 mmol), 4-(4,4,5,5-tetramethyl-1,3,2-dioxaborolan-2-yl)-1H-pyrazole (4.13 g, 21.3 mmol) and $Cs_2CO_3$ (8.68 g, 26.6 mmol) in NMP (50 mL) was stirred at 80° C. for 4 h. The reaction mixture was diluted with DCM and washed with brine. The organic layer was evaporated in vacuo. The residue was purified by flash column chromatography on silica gel (PE/EA=5/1) to afford the title compound (lv) (1.2 g, 24% yield). MS (ES+) $C_{14}H_{23}BN_2O_3$ requires: 278, found: 279 [M+H]+.

Step 3: Synthesis of (S)-1-(4-fluorophenyl)-1-(2-(4-(6-(1-(tetrahydro-2H-pyran-4-yl)-1H-pyrazol-4-yl)pyrrolo[2,1-f][1,2,4]triazin-4-yl)piperazin-1-yl)pyrimidin-5-yl)ethan-1-amine (16): A mixture of I-1 (300 mg, 603 mol), 1-(tetrahydro-2H-pyran-4-yl)-4-(4,4,5,5-tetramethyl-1,3,2-dioxaborolan-2-yl)-1H-pyrazole (lv) (210 mg, 754 μmol), $K_2CO_3$ (104 mg, 754 mol), and Pd(dppf)Cl$_2$ (30 mg, 41 μmol) in DMF/H$_2$O (10 mL/2 ml) was stirred at 70° C. under N$_2$ (g) for 4 hrs. After that, the solution was diluted with EA, washed with H$_2$O and brine, and concentrated. The residue was purified by Prep-HPLC (Mobile phase: A=H$_2$O (0.1% NH$_4$HCO$_3$), B=acetonitrile; Gradient: B=15%-95% in 18 min; Column: Xtimate™ 10 um 150A 21.2×250 mm) followed by lyophilization to afford the title compound (16) (40.2 mg, 6% yield) as a white solid. MS (ES+) $C_{30}H_{33}FN_{10}O$ requires: 568, found: 569 [M+H]+. $^1$H NMR (400 MHz, 6d-DMSO) δ ppm 8.41 (s, 2H), 8.19 (s, 1H), 7.99 (s, 1H), 7.88 (s, 1H), 7.86 (s, 1H), 7.48-7.45 (m, 2H), 7.24 (s, 1H), 7.13-7.09 (m, 2H), 4.42-4.37 (m, 1H), 4.12-4.40 (m, 4H), 3.99-3.96 (m, 2H), 3.92-3.90 (m, 4H), 3.52-3.46 (m, 2H), 2.43 (s, 2H), 2.05-1.92 (m, 4H), 1.73 (s, 3H).

Example 17: (3R,4R)-4-(4-(4-(4-(5-((S)-1-Amino-1-(4-fluorophenyl)ethyl)pyrimidin-2-yl)piperazin-1-yl)pyrrolo[2,1-f][1,2,4]triazin-6-yl)-1H-pyrazol-1-yl)tetrahydrofuran-3-ol (17)

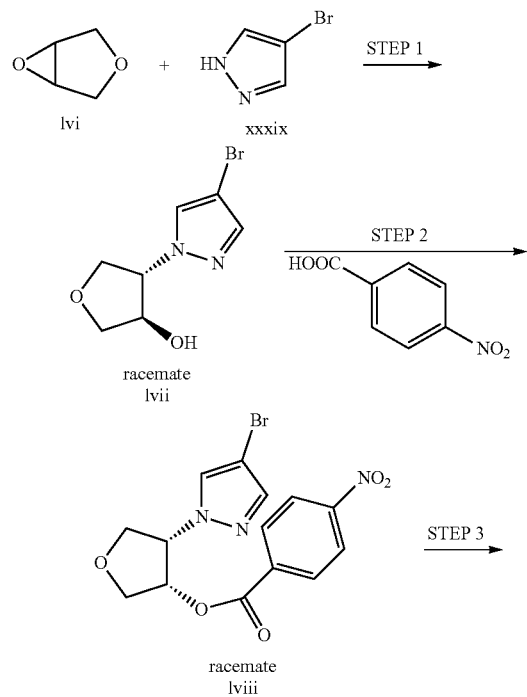

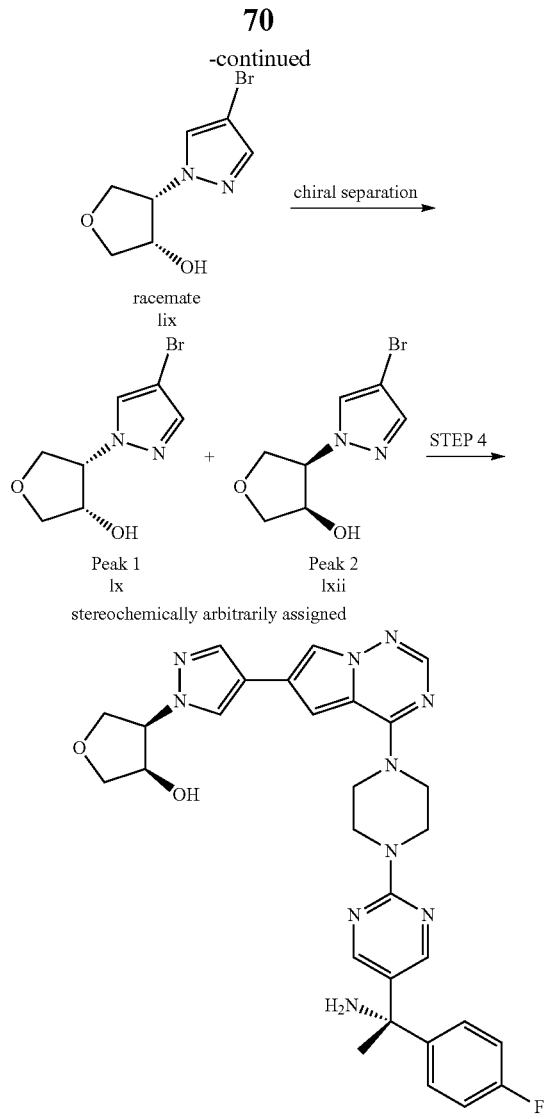

Step 1: Synthesis of rac-trans-4-(4-bromo-1H-pyrazol-1-yl)tetrahydrofuran-3-ol (lvii): To a solution of 3,6-dioxabicyclo[3.1.0]hexane (lvi) (5.2 g, 60.5 mmol), 4-bromo-1H-pyrazole (xxxix) (8.8 g, 60.5 mmol) and Cs$_2$CO$_3$ (39.3 g, 121 mmol) in NMP (100 mL) was stirred at 120° C. for 16 h. The solution was cooled and diluted with DCM, then washed with H$_2$O and brine. The organic layer was concentrated and purified by flash column chromatography on silica gel (PE/EA=3/1) to afford the title compound (lvii) (10 g, 71% yield) as a colorless solid. MS (ES+) $C_7H_9BrN_2O_2$ requires: 232, found: 233 [M+18]+.

Step 2: Synthesis of rac-cis-4-(4-bromo-1H-pyrazol-1-yl)tetrahydrofuran-3-yl 4-nitrobenzoate (lviii): A mixture of rac-trans-4-(4-bromo-1H-pyrazol-1-yl)tetrahydrofuran-3-ol (lvii) (2.7 g, 11.6 mmol), 4-nitrobenzoic acid (1.95 g, 11.6 mmol), diisopropyl azodicarboxylate (3.53 mg, 17.4 mmol), and triphenylphosphine (4.57 g, 17.4 mmol) in THF (50 mL) was stirred at RT for 16 h. The solution was diluted with EA and washed with H$_2$O and brine. The organic layer was concentrated and purified by flash column chromatography on silica gel (PE/EA=3/1) to afford the title compound (lviii) (4 g, 90% yield) as a colorless solid. MS (ES+) $C_{14}H_{12}BrN_3O_5$ requires: 381, found: 382 [M+H]+.

Step 3: Synthesis of (3S,4S)-4-(4-bromo-1H-pyrazol-1-yl)tetrahydrofuran-3-ol (lx) (Peak 1) and (3R,4R)-4-(4-bromo-1H-pyrazol-1-yl)tetrahydrofuran-3-ol(lxi) (Peak 2): A mixture of rac-cis-4-(4-bromo-1H-pyrazol-1-yl)tetrahydrofuran-3-yl 4-nitrobenzoate (lvii) (4 g, 10.5 mmol) and lithium hydroxide (2.2 g, 52.5 mmol) in MeOH/THF/H$_2$O (30 mL/30 mL/30 mL) was stirred at RT for 4 h. The resulting mixture was diluted with EA, washed with H$_2$O and brine, and concentrated in vacuo. The residue was purified by flash column chromatography on silica gel (PE/EA=3/1=3/1) to afford rac-cis-4-(4-bromo-1H-pyrazol-1-yl)tetrahydrofuran-3-ol (1.3 g, 53% yield) as a colorless solid. MS (ES+) C$_7$H$_9$BrN$_2$O$_2$ requires: 232, found: 233 [M+H]$^+$. This material was subjected to chiral separation via SFC (Column: AD 20*250 mm, 10 μm (Daicel); Mobile Phase: CO$_2$/MeOH (0.2% ammonia in methanol)=60/40; Flow Rate: 80 g/min) to afford Peak 1 (lx) (500 mg) and Peak 2 (lxi) (500 mg). Peak 1 was arbitrarily assigned as (3S,4S)-4-(4-bromo-1H-pyrazol-1-yl)tetrahydrofuran-3-ol and Peak 2 was arbitrarily assigned as (3R,4R)-4-(4-bromo-1H-pyrazol-1-yl)tetrahydrofuran-3-ol.

Step 4: Synthesis of (3R,4R)-4-(4-(4-(4-(5-((S)-1-amino-1-(4-fluorophenyl)ethyl)pyrimidin-2-yl)piperazin-1-yl)pyrrolo[2,1-f][1,2,4]triazin-6-yl)-1H-pyrazol-1-yl)tetrahydrofuran-3-ol (17): A mixture of (3R,4R)-4-(4-bromo-1H-pyrazol-1-yl)tetrahydrofuran-3-ol(lxi) (70 mg, 0.3 mmol) (Peak 2 from Step 3), 1-3 (328.3 mg, 0.6 mmol), Pd[(t-Bu)$_3$P]$_2$ (31 mg, 0.06 mmol) and Na$_2$CO$_3$ (96 mg, 0.9 mmol) in dioxane/H$_2$O (8 mL/2 mL) was stirred at 90° C. for 4 h. After cooling, the solution was diluted with EA, washed with H$_2$O and brine, and concentrated. The residue was purified by flash column chromatography on silica gel (DCM/MeOH=10/1) to afford the title compound (17) (106.3 mg, 62% yield) as a white solid. MS (ES+) C$_{29}$H$_{31}$FN$_{10}$O$_2$ requires: 570, found: 571, 554 [M+H]$^+$. $^1$H-NMR (400 MHz, 6d-DMSO) δ ppm 8.41 (s, 2H), 8.15 (s, 1H), 8.03 (s, 1H), 7.88 (s, 1H), 7.87 (s, 1H), 7.52-7.42 (m, 2H), 7.28 (s, 1H), 7.17-7.10 (m, 2H), 5.33 (d, 1H, J=4.8 Hz), 4.92-4.83 (m, 1H), 4.46-4.38 (m, 1H), 4.21-4.05 (m, 6H), 4.01 (m, 1H), 3.95-3.85 (m, 4H), 3.73 (m, 1H), 2.45 (s, 2H), 1.73 (s, 3H).

Example 18: (3R,4S)-4-(4-(4-(4-(5-((S)-1-amino-1-(4-fluorophenyl)ethyl)pyrimidin-2-yl)piperazin-1-yl)pyrrolo[2,1-f][1,2,4]triazin-6-yl)-1H-pyrazol-1-yl)tetrahydrofuran-3-ol (18)

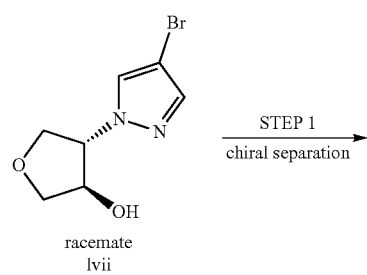

racemate
lvii

STEP 1
chiral separation

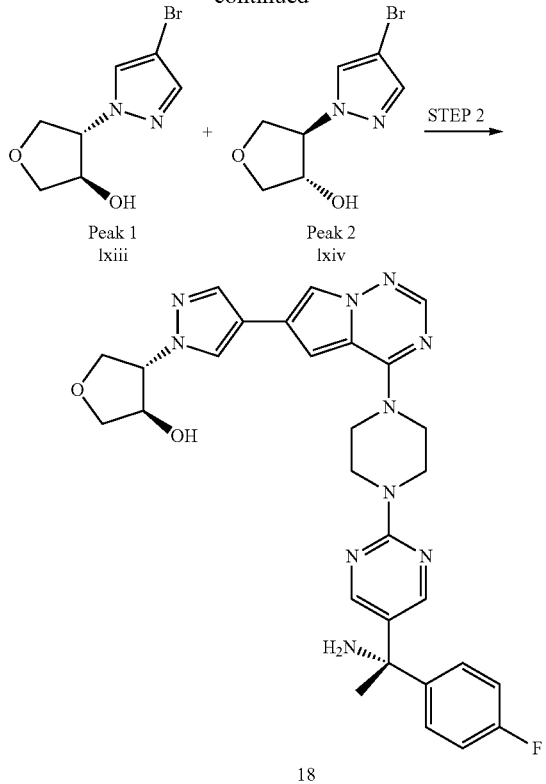

Peak 1
lxiii

Peak 2
lxiv

STEP 2

18

Step 1: Chiral separation of rac-trans-4-(4-bromo-1H-pyrazol-1-yl)tetrahydrofuran-3-ol(lvii): rac-trans-4-(4-bromo-1H-pyrazol-1-yl)tetrahydrofuran-3-ol (1.1 g) (from Step 1 of Example 17) was subjected to chiral separation via SFC (Column: AD 20*250 mm, 10 μm (Daicel); Mobile Phase: CO$_2$/MeOH (0.2% ammonia in MeOH)=80/20; Flow Rate: 80 g/min) to afford Peak 1 (lxiii) (400 mg) and Peak 2 (lxiv) (500 mg). Peak 1 was arbitrarily assigned as (3R,4S)-4-(4-bromo-1H-pyrazol-1-yl)tetrahydrofuran-3-ol and Peak 2 was arbitrarily assigned as (3S,4R)-4-(4-bromo-1H-pyrazol-1-yl)tetrahydrofuran-3-ol.

Step 2: Synthesis of (3R,4S)-4-(4-(4-(4-(5-((S)-1-amino-1-(4-fluorophenyl)ethyl)pyrimidin-2-yl)piperazin-1-yl)pyrrolo[2,1-f][1,2,4]triazin-6-yl)-1H-pyrazol-1-yl)tetrahydrofuran-3-ol (18): A mixture of (3R,4S)-4-(4-bromo-1H-pyrazol-1-yl)tetrahydrofuran-3-ol (70 mg, 0.3 mmol) (lxiii) (Peak 1 from Step 1), 1-3 (328.3 mg, 0.6 mmol), Pd[(t-Bu)$_3$P]$_2$ (31 mg, 0.06 mmol) and Na$_2$CO$_3$ (96 mg, 0.9 mmol) in dioxane/H$_2$O (8 mL/2 mL) was degassed with N$_2$ and stirred at 90° C. for 4 h. After that, the solution was diluted with DCM, washed with H$_2$O and brine, and concentrated. The residue was purified by flash column chromatography on silica gel (DCM/MeOH=10/1) to afford the title compound (18) (55.6 mg, 33% yield) as a white solid. MS (ES+) C$_{29}$H$_{31}$FN$_{10}$O$_2$ requires: 570, found: 571, 554 [M+H]$^+$, [M+H—NH$_3$]$^+$. $^1$H-NMR (400 MHz, 6d-DMSO) δ ppm 8.41 (s, 2H), 8.15 (s, 1H), 8.03 (s, 1H), 7.91 (s, 1H), 7.88 (s, 1H), 7.51-7.43 (m, 2H), 7.28 (s, 1H), 7.16-7.07 (m, 2H), 5.66 (d, 1H, J=4 Hz), 4.75-4.67 (m, 1H), 4.51-4.42 (m, 1H), 4.20 (m, 1H), 4.15-3.99 (m, 6H), 3.96-3.85 (m, 4H), 3.63 (m, 1H), 2.47 (s, 2H), 1.73 (s, 3H).

Example 19: (3S,4R)-4-(4-(4-(4-(5-((S)-1-Amino-1-(4-fluorophenyl)ethyl)pyrimidin-2-yl)piperazin-1-yl)pyrrolo[2,1-f][1,2,4]triazin-6-yl)-1H-pyrazol-1-yl)tetrahydrofuran-3-ol (19)

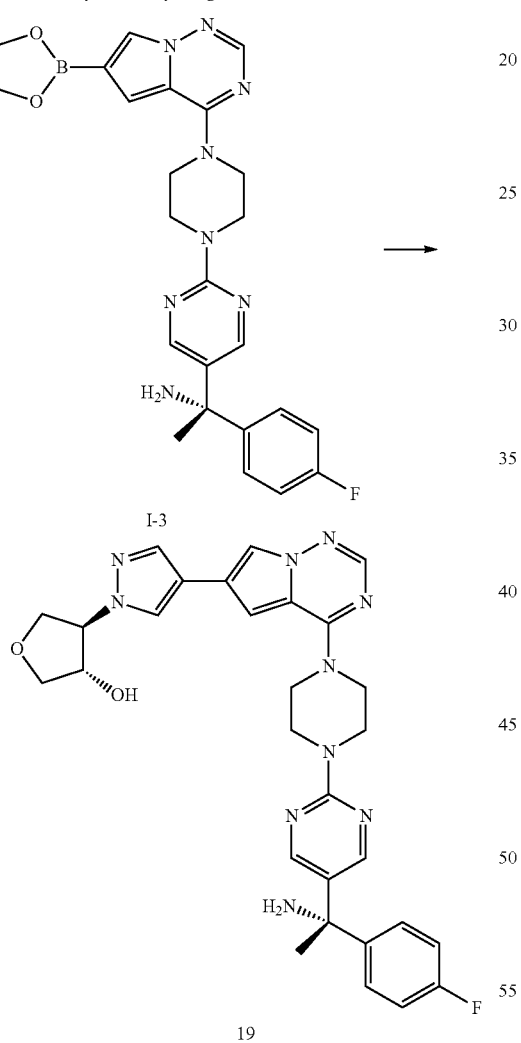

A mixture of (3S,4R)-4-(4-bromo-1H-pyrazol-1-yl)tetrahydrofuran-3-ol (70 mg, 0.3 mmol) (lxiv) (Peak 2 from Step 1 of Example 22), I-3 (328.3 mg, 0.6 mmol), Pd[(t-Bu)$_3$P]$_2$ (31 mg, 0.06 mmol) and Na$_2$CO$_3$ (96 mg, 0.9 mmol) in dioxane/H$_2$O (8 mL/2 mL) was degassed with N$_2$ and stirred at 90° C. for 4 h. After that, the solution was diluted with EA, washed with H$_2$O and brine, and concentrated. The residue was purified by flash column chromatography on silica gel (DCM/MeOH=10/1) to afford the title compound (19) (51.9 mg, 31% yield) as a white solid. MS (ES+) C$_{29}$H$_{31}$FN$_{10}$O$_2$ requires: 570, found: 571, 554 [M+H]$^+$ and [M+H—NH$_3$]$^+$. $^1$H-NMR (400 MHz, 6d-DMSO) δ ppm 8.41 (s, 2H), 8.15 (s, 1H), 8.03 (s, 1H), 7.91 (s, 1H), 7.88 (s, 1H), 7.52-7.43 (m, 2H), 7.28 (s, 1H), 7.19-7.06 (m, 2H), 5.66 (d, 1H, J=4.4 Hz), 4.75-4.66 (m, 1H), 4.51-4.41 (m, 1H), 4.20 (m, 1H), 4.16-3.99 (m, 6H), 3.97-3.83 (m, 4H), 3.63 (dd, 1H, J=9.6 Hz, J=2.8 Hz), 2.54 (s, 2H), 1.73 (s, 3H).

Example 20: (3S,4S)-4-(4-(4-(4-(5-((S)-1-Amino-1-(4-fluorophenyl)ethyl)pyrimidin-2-yl)piperazin-1-yl)pyrrolo[2,1-f][1,2,4]triazin-6-yl)-1H-pyrazol-1-yl)tetrahydrofuran-3-ol (20)

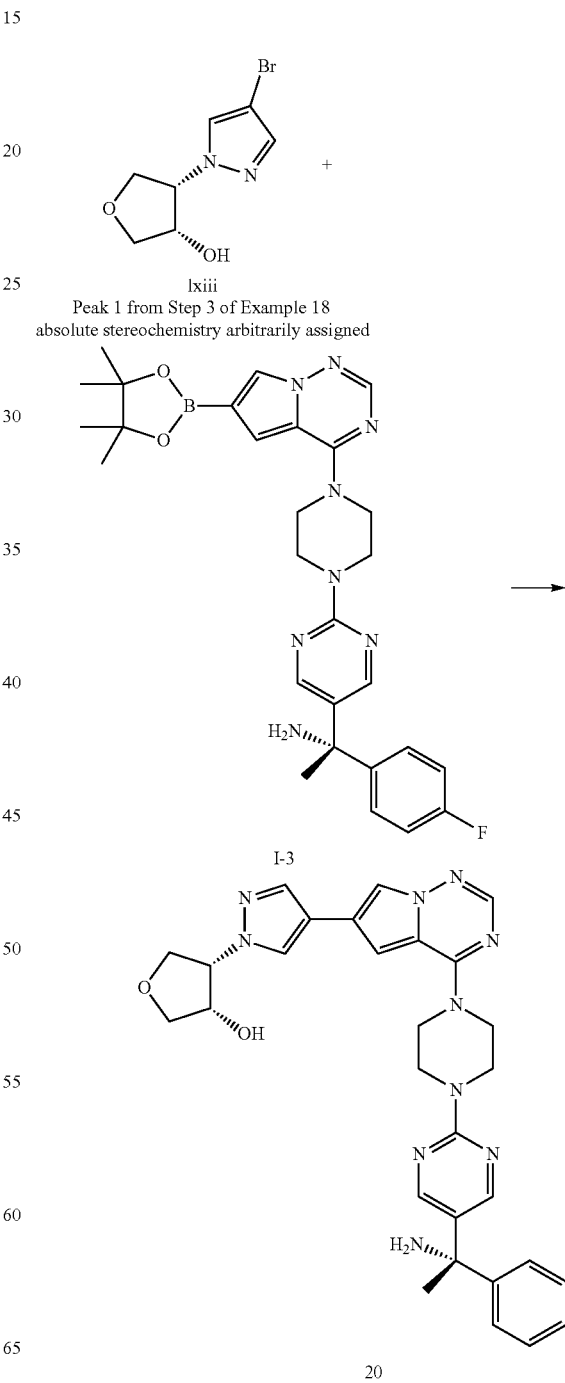

A mixture of (3S,4S)-4-(4-bromo-1H-pyrazol-1-yl)tetrahydrofuran-3-ol(lxiii) (50 mg, 0.22 mmol) (Peak 1 from Step 3 of Example 21), 1-3 (234.5 mg, 0.44 mmol), Pd[(t-Bu)$_3$P]$_2$ (22 mg, 0.044 mmol) and Na$_2$CO$_3$ (68 mg, 0.66 mmol) in dioxane/H$_2$O (8 mL/2 mL) was stirred at 90° C. for 4 h. After cooling, the solution was diluted with EA, washed with H$_2$O and brine, and concentrated. The residue was purified by flash column chromatography on silica gel (DCM/MeOH=10/1) to afford the title compound (20) (74.6 mg, 61% yield) as a white solid. MS (ES+) C$_{29}$H$_{31}$FN$_{10}$O$_2$ requires: 570, found: 571, 554 [M+H]$^+$. $^1$H-NMR (400 MHz, 6d-DMSO) δ ppm 8.41 (s, 2H), 8.15 (s, 1H), 8.03 (d, 1H, J=1.6 Hz), 7.88 (s, 1H), 7.87 (s, 1H), 7.51-7.44 (m, 2H), 7.28 (d, 1H, J=1.2 Hz), 7.17-7.10 (m, 2H), 5.33 (d, 1H, J=5.6 Hz), 4.93-4.83 (m, 1H), 4.47-4.38 (m, 1H), 4.20-4.06 (m, 6H), 4.01 (m, 1H), 3.95-3.88 (m, 4H), 2.45 (s, 2H), 3.73 (m, 1H), 1.76 (s, 3H).

Example 21: (1S,2S)-2-(4-(4-(4-(5-((S)-1-Amino-1-(4-fluorophenyl)ethyl)pyrimidin-2-yl)piperazin-1-yl)pyrrolo[2,1-f][1,2,4]triazin-6-yl)-1H-pyrazol-1-yl)cyclobutanol (21)

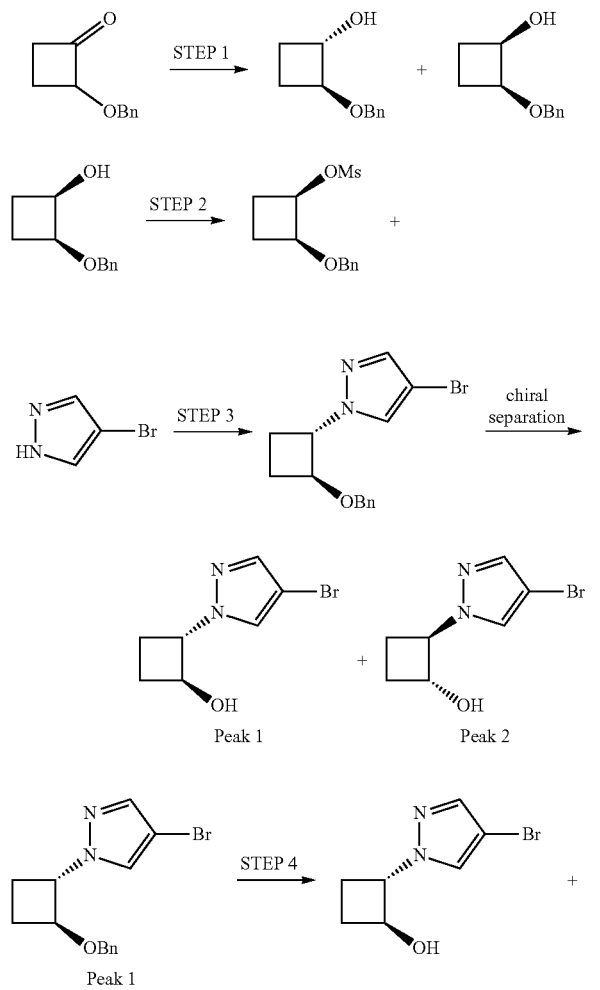

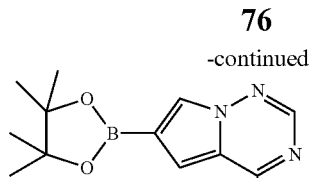

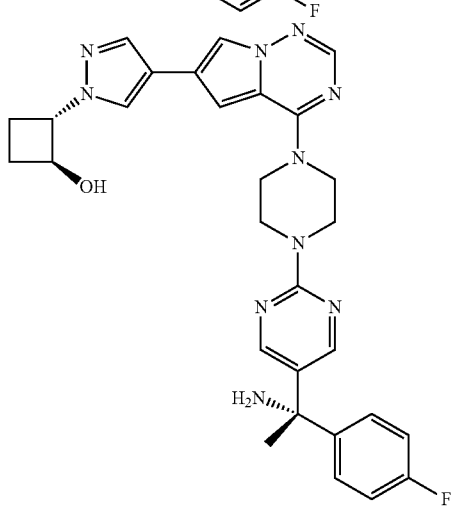

Step 1: Synthesis of trans-2-(benzyloxy)cyclobutanol and cis-2-(benzyloxy)cyclobutanol: To a solution of 2-(benzyloxy)cyclobutanone (1.0 g, 5.7 mmol) in MeOH (20 mL) was added NaBH$_4$ (432 mg, 11.4 mmol) at 0° C. Then the solution was stirred at room temperature for 3 h. The mixture was diluted with EA, washed with water and brine, then the organic layer was concentrated and purified by flash column chromatography on silica gel (petroleum ether/ethyl acetate=5/1) to afford 400 mg of Peak 1 (arbitrarily assigned as cis-2-(benzyloxy)cyclobutanol) as a colorless oil and 400 mg of Peak 2 (arbitrarily assigned as trans-2-(benzyloxy)cyclobutanol) as a colorless oil. MS (ES+) C$_{11}$H$_{14}$O$_2$ requires: 178, found: 179 [M+H]$^+$.

Step 2: Synthesis of cis-2-(benzyloxy)cyclobutyl methanesulfonate: To a solution of cis-2-(benzyloxy)cyclobutanol (270 mg, 1.52 mmol) in DCM (10 mL) was added mesyl chloride (259 mg, 2.28 mmol) and triethylamine (459 mg, 4.56 mmol) at 0° C. The mixture was stirred at room temperature for 3 h. After that, the solution was diluted with DCM, washed with water and brine, dried over anhydrous Na$_2$SO$_4$, and concentrated to afford the title compound (300 mg, 77% yield) as a colorless oil. MS (ES+) C$_{12}$H$_{16}$O$_4$S requires: 256, found: 274 [M+18]$^+$.

Step 3: Synthesis of trans-2-(benzyloxy)cyclobutyl)-4-bromo-1H-pyrazole: A mixture of cis-2-(benzyloxy)cyclobutyl methanesulfonate (300 mg, 1.17 mmol), 4-bromo-1H-pyrazole (171 mg, 1.17 mmol), and Cs$_2$CO$_3$ (1.15 g, 3.51 mmol) in DMF (8 mL) was stirred at 100° C. for 16 h. After that, the solution was diluted with EA, washed with water and brine, dried over anhydrous $Na_2SO_4$, concentrated and purified by flash column chromatography (PE/EA=5/1) to afford the title compound (170 mg, 47% yield) as a colorless oil. MS (ES+) $C_{14}H_{15}BrN_2O$ requires: 306, found: 307 [M+H]+. Chiral separation of trans-2-(benzyloxy)cyclobutyl)-4-bromo-1H-pyrazole: trans-2-(benzyloxy)cyclobutyl)-4-bromo-1H-pyrazole (600 mg) was subjected to chiral separation via SFC (Column: IG 20*250 mm, 10 μm (Daicel); Mobile Phase: $CO_2$/MeOH (0.2% ammonia in methanol)=75/25; Flow Rate: 4 g/min) to afford Peak 1 (250 mg) and Peak 2 (250 mg). Peak 1 was arbitrarily assigned as 1-((1S,2S)-2-(benzyloxy)cyclobutyl)-4-bromo-1H-pyrazole and peak 2 was arbitrarily assigned as 1-((1R,2R)-2-(benzyloxy)cyclobutyl)-4-bromo-1H-pyrazole.

Step 4: Synthesis of (1S,2S)-2-(4-bromo-1H-pyrazol-1-yl)cyclobutanol: To a solution of 1-((1S,2S)-2-(benzyloxy)cyclobutyl)-4-bromo-1H-pyrazole (250 mg, 820 μmol) in TFA (2 mL) was stirred at 80° C. for 16 h. After that, the solution was concentrated and purified by flash column chromatography on silica gel (petroleum ether/ethyl acetate=3/1) to afford the title compound (120 mg, 68% yield) as a white solid. MS (ES+) $C_7H_9BrN_2O$ requires: 216, found: 217 [M+H]+.

Step 5: Synthesis of (1S,2S)-2-(4-(4-(4-(5-((S)-1-amino-1-(4-fluorophenyl)ethyl)pyrimidin-2-yl)piperazin-1-yl)pyrrolo[2,1-f][1,2,4]triazin-6-yl)-1H-pyrazol-1-yl)cyclobutanol: A mixture of (1S,2S)-2-(4-bromo-1H-pyrazol-1-yl)cyclobutanol (120 mg, 556 mol), 1-3 (362 mg, 667 mol), $Pd(t-Bu_3P)_2$ (50 mg, 99 μmol) and $Cs_2CO_3$ (362 mg, 1.12 mmol) in dioxane/$H_2O$ (8 mL/2 mL) was purged with $N_2$ for 10 mins and stirred at 90° C. for 4 hrs under $N_2$. After that, the solution was diluted with DCM, washed with $H_2O$ and brine, and concentrated. The residue was purified by flash column chromatography on silica gel (DCM/MeOH=10/1). The resulting material was purified further by Prep-HPLC (Mobile phase: A=$H_2O$ (0.1% NH4HCO3), B=acetonitrile; Gradient: B=32%-62% in 18 min; Column: Xtimate™ 10 um 150A 21.2×250 mm) followed by lyophilization to afford the title compound (52.6 mg, 17% yield) as a white solid. MS (ES+) $C_{29}H_{31}FN_{10}O$ requires: 554, found: 555 [M+H]+.
1H-NMR (400 MHz, 6d-DMSO) δ ppm 8.41 (s, 2H), 8.19 (s, 1H), 8.00 (d, 1H, J=1.6 Hz), 7.88 (s, 2H), 7.48-7.44 (m, 2H), 7.26 (d, 1H, J=1.6 Hz), 7.14-7.08 (m, 2H), 5.67 (d, 1H, J=7.2 Hz), 4.46-4.39 (m, 1H), 4.34-4.26 (m, 1H), 4.10-4.06 (m, 4H), 3.92-3.90 (m, 4H), 2.44 (s, 2H), 2.16-2.10 (m, 2H), 1.89-1.79 (m, 1H), 1.73 (s, 3H), 1.62-1.52 (m, 1H).

Example 22: (1R,2R)-2-(4-(4-(4-(5-((S)-1-Amino-1-(4-fluorophenyl)ethyl)pyrimidin-2-yl)piperazin-1-yl)pyrrolo[2,1-f][1,2,4]triazin-6-yl)-1H-pyrazol-1-yl)cyclobutanol (22)

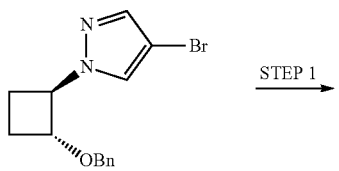

Peak 2 from Step 3 of Example 26
Absolute stereochemistry arbitrarily assigned

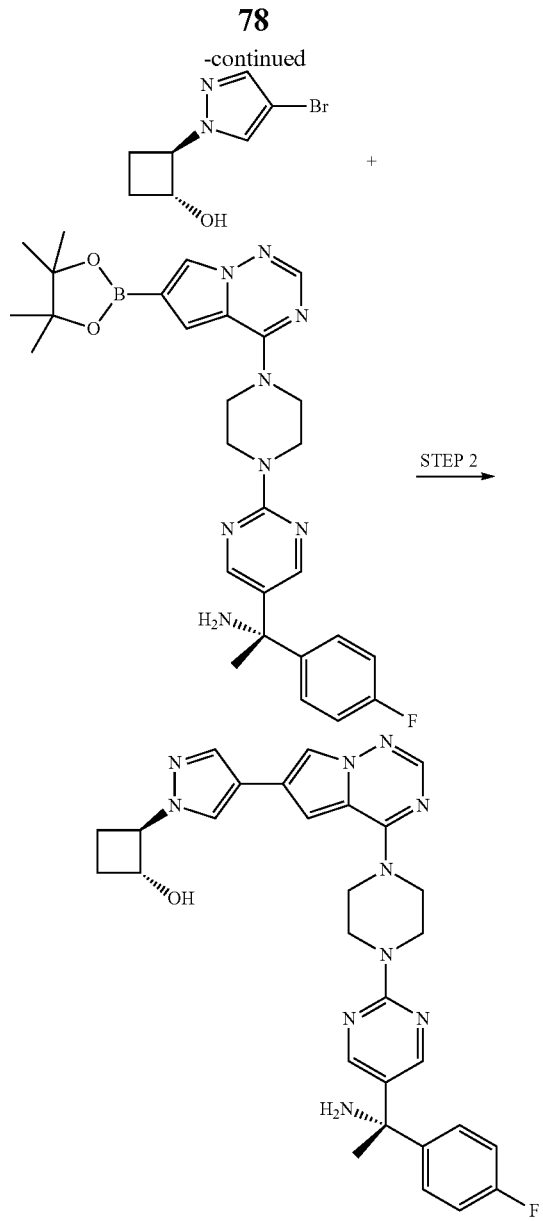

Step 1: Synthesis of (1R,2R)-2-(4-bromo-1H-pyrazol-1-yl)cyclobutanol: To a solution of 14(1R,2R)-2-(benzyloxy)cyclobutyl)-4-bromo-1H-pyrazole (250 mg, 820 μmol) (from Peak 2 in Step 3 of Example 21) in TFA (2 mL) was stirred at 80° C. for 16 h. After that, the solution was concentrated and purified by flash column chromatography on silica gel (petroleum ether/ethyl acetate=3/1) to afford the title compound (120 mg, 68% yield) as a white solid. MS (ES+) $C_7H_9BrN_2O$ requires: 216, found: 217 [M+H]+.

Step 2: Synthesis of (1R,2R)-2-(4-(4-(4-(5-((S)-1-amino-1-(4-fluorophenyl)ethyl)pyrimidin-2-yl)piperazin-1-yl)pyrrolo[2,1-f][1,2,4]triazin-6-yl)-1H-pyrazol-1-yl)cyclobutanol: A mixture of (1R,2R)-2-(4-bromo-1H-pyrazol-1-yl)cyclobutanol (120 mg, 556 μmol), (S)-1-(4-fluorophenyl)-1-(2-(4-(6-(4,4,5,5-tetramethyl-1,3,2-dioxaborolan-2-yl)pyrrolo[2,1-f][1,2,4]triazin-4-yl)piperazin-1-yl)pyrimidin-5-yl)ethanamine (362 mg, 667 mol), $Pd(t-Bu_3P)_2$ (50 mg, 99 μmol) and $Cs_2CO_3$ (362 mg, 1.12 mmol) in dioxane/$H_2O$ (8 mL/2 mL) was purged with $N_2$ (g) for 10 min and stirred at 90° C. for 4 h under N (g). After that, the solution was diluted with EA, washed with $H_2O$ and brine, and concentrated. The residue was purified by flash column chromatography on silica gel (DCM/MeOH=10/1). The resulting material was purified further by Prep-HPLC (Mobile phase: A=H$_2$O (0.1% NH$_4$HCO$_3$), B=acetonitrile; Gradient: B=30%-60% in 18 min; Column: Xtimate™ 10 um 150A 21.2×250 mm) followed by lyophilization to afford the title compound (51.5 mg, 17% yield) as a white solid. MS (ES+) C$_{29}$H$_{31}$FN$_{10}$O requires: 554, found: 555 [M+H]$^+$. $^1$H-NMR (400 MHz, 6d-DMSO) δ ppm 8.41 (s, 2H), 8.19 (s, 1H), 8.00 (d, 1H, J=1.6 Hz), 7.88 (s, 2H), 7.48-7.44 (m, 2H), 7.26 (d, 1H, J=1.6 Hz), 7.14-7.08 (m, 2H), 5.67 (d, 1H, J=7.2 Hz), 4.46-4.39 (m, 1H), 4.34-4.26 (m, 1H), 4.10-4.06 (m, 4H), 3.92-3.90 (m, 4H), 2.44 (s, 2H), 2.16-2.10 (m, 2H), 1.89-1.79 (m, 1H), 1.73 (s, 3H), 1.62-1.52 (m, 1H).

EXAMPLE 2: Biochemical Enzymatic Activity Assays

PDGFRα and KIT enzymatic activity was monitored using the Perkin Elmer electrophoretic mobility shift technology platform, the EZReader 2. Fluorescent labeled substrate peptide was incubated in the presence of kinase and ATP, and in the presence of test compound, such that each dose of test compound resulted in a reflective proportion of the peptide to be phosphorylated.

Within the linear, steady-state phase of the kinase enzymatic reaction, the mixed pool of phosphorylated (product) and non-phosphorylated (substrate) peptides was passed through the microfluidic system of the PerkinElmer EZ Reader 2, under an applied electric potential difference. The presence of the phosphate group on the product peptide provided a difference in mass and charge between that of the substrate peptide, resulting in a separation of the substrate and product pools in the sample (Perrin et al., Expert Opin Drug Discovery 2010 Jan. 5(1):51-63).

As the product and substrate peptide mixture passes the lasers within the instrument, these pools are detected ($\lambda_{ex}$=488 nm, $\lambda_{em}$=568 nm) and resolved as separate peaks. The ratio between these peaks reflects the activity of the compound at that concentration, in that well, under those conditions.

Inhibition of KIT (D816V) PDGFRα (D842V) Mutant Biochemical Enzymatic Activity

All test articles were dissolved in 100% DMSO at a stock concentration of 10 mM. A 100×, 10-point, 4-fold serial dilution of all test compounds was created in 100% DMSO, starting at a relevant concentration, usually 1 mM. A volume of 0.130 μL of each concentration was transferred to the relevant well of a 384-well assay plate (Greiner 781 201) using a TTPLabtech Mosquito nano-liter dispenser. Using the Multidrop, the remaining constituents of the reaction were then added to the 0.130 μL of compound as follows:

PDGFRα D842V assay at the apparent Michaelis-Menten constant (APPKM) for ATP: In each well of a 384-well assay plate, 7 nM of untreated enzyme was incubated in a total of 13 μL of buffer (100 mM HEPES pH 7.5, 0.015% Brij 35, 10 mM MgCl$_2$, 1 mM DTT) with 1 μM CSKtide (5-FAM-AHA-KKKKDDIYFFFG (SEQ ID NO: 19)-NH2) and 25 μM ATP at 25° C. for 90 minutes in the presence or absence of a dosed concentration series of compound (1% DMSO final concentration). The reaction was stopped by the addition of 70 μl of Stop buffer (100 mM HEPES pH 7.5, 0.015% Brij 35, 35 mM EDTA and 0.2% of Coating Reagent 3, Caliper Lifesciences). The plate was read on a Caliper EZReader 2.

KIT D816V assay at the APPKM for ATP: In each well of a 384-well assay plate, 0.3 nM of untreated enzyme was incubated in a total of 13 μL of buffer (100 mM HEPES pH 7.5, 0.015% Brij 35, 10 mM MgCl$_2$, 1 mM DTT) with 1 μM SRCtide (5-FAM-GEEPLYWSFPAKKK (SEQ ID NO: 20)-NH2) and 20 μM ATP at 25° C. for 60 minutes in the presence or absence of a dosed concentration series of compound (1% DMSO final concentration). The reaction was stopped by the addition of 70 μl of Stop buffer (100 mM HEPES pH 7.5, 0.015% Brij 35, 35 mM EDTA and 0.2% of Coating Reagent 3, Caliper Lifesciences). The plate was read on a Caliper EZReader 2. The results obtained in these experiments for compounds prepared according to the examples are summarized in Table 2 below. For biochemical D816V and D842V activity, the following designations are used: ≤0.30 nM=A; ≥0.31 and <1 nM=B; and ND=not determined. For cellular activity in the HMC1.2 cell line, the following designations are used: A means <4.5 nM; B means≥4.6 and <10 nM; and ND=not determined.

TABLE 2

| Compound No. | KIT D816V (nM) | PDGFRα D842V (nM) | KIT (P-KIT HMC1.2 (nM)) |
|---|---|---|---|
| 1 | A | A | B |
| 2 | B | A | B |
| 3 | A | A | A |
| 4 | A | A | A |
| 5 | A | A | A |
| 6 | A | A | B |
| 7 | A | A | A |
| 8 | A | A | A |
| 9 | A | A | A |
| 10 | B | A | A |
| 11 | A | A | B |
| 12 | A | A | A |
| 13 | B | A | A |
| 14 | A | A | A |
| 15 | A | A | A |
| 16 | A | A | B |
| 17 | B | A | B |
| 18 | A | A | A |
| 19 | A | A | A |
| 20 | A | A | A |
| 21 | B | A | A |
| 22 | A | A | A |
| Example 63 WO2015/057873 ("63") | A | A | A |

For reference, the chemical structure of the compound of Example 63 in WO2015/057873 is:

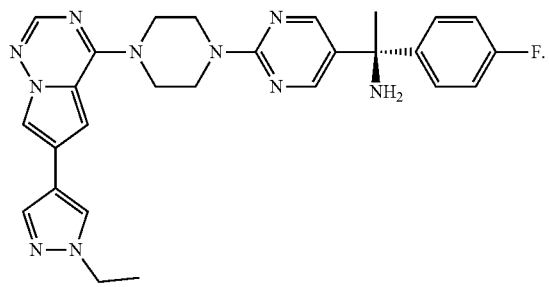 [SMILES: CCn1cc(-c2cc3c(N4CCN(c5ncc([C@@](C)(N)c6ccc(F)cc6)cn5)CC4)ncnn3c2)cn1]

Example 3: HMC1.2 Autophosphorylation Assay 10,000 HMC1.2 cells were incubated in 22 μL culture media (phenol-red free IMDM, no serum) in each well of a 384-well plate and serum starved overnight in a tissue culture incubator (5% $CO_2$, 37° C.). A 10-point dose concentration series of compound (2.5 µM-9.54 pM) were then added to the cells in a volume of 3.1 µL to each well (0.25% DMSO final concentration). After 90 minutes, 6 µL of 5× AlphaLISA Lysis Buffer (Perkin Elmer) supplemented with a protease and phosphatase inhibitor cocktail (Cell Signaling Technologies) was added to each well and shaken at 450 rpm for 15 minutes at 4° C. 10 µL of phospho-Y719 c-KIT and total c-KIT antibodies (15 nM final concentration, Cell Signaling Technologies) and 50 µg/mL AlphaLISA rabbit acceptor beads (Perkin Elmer) were added to each well and shaken at 300 rpm at room temperature for 2 hours. 10 µL of 100 µg/mL streptavidin donor beads (Perkin Elmer) were added to each well, blocked from light with solid black adhesive and shaken at 300 rpm at room temperature for 2 hours. Fluorescence signal was obtained on Envision (Perkin Elmer) by AlphaScreen 384 well HTS protocol. Data was normalized to 0% and 100% inhibition controls and the $IC_{50}$ was calculated using Four Parameter Logistic $IC_{50}$ curve fitting.

The Table shows the activity of compounds in a Mast cell leukemia cell line, HMC 1.2. This cell line contains KIT mutated at positions V560G and D816V resulting in constitutive activation of the kinase. The following compounds were tested in an assay to measure direct inhibition of KIT D816V kinase activity by assaying KIT autophosphorylation at tyrosine 719 on the KIT protein. The results of these experiments for compounds prepared according to the examples are summarized in Table 2.

Example 4: Evaluation of Brain Penetration in Rats Brain to Plasma Ratios (Kp,brain)

To understand the brain penetration, brain to plasma ratios of the compounds were obtained in Sprague-Dawley (SD) rats. In vivo equilibrium distribution between blood and brain in preclinical species such as rats is a commonly used parameter to evaluate brain penetration. $K_p$,brain is the ratio of concentrations in brain and blood ($C_{brain}/C_{plasma}$) The compound's passive diffusion characteristics, its affinity for membrane transporters at the blood-brain barrier (BBB), and the relative drug binding affinity differences between the plasma proteins and brain tissue influence the $K_p$,brain. Compounds with $K_p$,brain smaller than 0.1 have restricted access to the CNS, whereas compounds with $K_p$,brain greater than 0.3-0.5 are considered to have good brain penetration and compounds with $K_p$,brain greater than 1 freely cross the BBB (Expert Opin. Drug Delivery (2016) 13 (01): 85-92).

The brain penetration of 4 and 63 were measured in Sprague-Dawley rats (3/compound). The animals received IV infusion of 1 mg/kg/hr of the compound over 24 hours via jugular vein cannulation. At 24 hours, blood was collected via tail vein bleeding or cardiac puncture (under anesthesia) and centrifuged to obtain plasma samples. Brain tissues were collected and homogenized with phosphate-buffered saline (PBS). The concentrations of the compounds were obtained in the plasma and brain homogenates by LC-MS/MS analysis. Table 3A below shows the results of the plasma and brain concentrations as well as $K_p$,brain for compound 4 prepared according to the examples described herein and compound 63 of WO2015/057873.

TABLE 3A

| | Brain Concentration (ng/mL) | Plasma Concentration (ng/mL) | Kp, brain |
|---|---|---|---|
| Compound 4 | | | |
| Rat 1 | 152 | 859 | 0.177 |
| Rat 2 | 188 | 1120 | 0.168 |
| Rat 3 | 208 | 1180 | 0.174 |
| Mean | 183 | 1053 | 0.174 |
| SD | 28.4 | 171 | 0.00507 |
| % CV | 15.5 | 16.2 | 2.92 |
| Compound 63 | | | |
| Rat 1 | 1920 | 1140 | 1.68 |
| Rat 2 | 1890 | 789 | 2.40 |
| Rat 3 | 1300 | 1100 | 1.18 |
| Mean | 1703 | 1010 | 1.75 |
| SD | 350 | 192 | 0.610 |
| % CV | 20.5 | 19.0 | 34.8 |

Compound 4 presents a very low $K_p$,brain (Mean=0.17) as compared to 63 (Mean=1.8).

Rat plasma protein binding of 4 and 63 were evaluated in vitro using an equilibrium dialysis method. Compound 4 (10 µM) was assessed in 100% plasma in a dialysis block for 5 hours at 37° C. Samples from the donor and receiver sides were analyzed by LC-MS/MS. Plasma protein bound and unbound fractions were calculated using the following equations—d $$\text{Fraction bound }(fb)^*(\%)=100\times([\text{Donor}]_{5h}-[\text{Receiver}]_{5h})/[\text{Donor}]_{5h} \quad \text{(Equation 1)}$$

$$\text{Fraction unbound }(fu),p^*(\%)=100-\% \text{ Bound}^* \quad \text{(Equation 2)}$$

where: $[\text{Donor}]_{5h}$ is measured donor concentration at 5-hour; $[\text{Received}]_{5h}$ is measured receiver concentration at 5-hour; fb* is bound fraction determined from plasma; fu,p* is calculated unbound fraction for plasma. Warfarin and quinidine were used as positive controls.

The fb for 4 and 63 were 97.92% and 99.8% respectively. Thus, fu,p of 4 and 63 were 2.08% and 0.2% respectively.

Similarly, rat brain protein binding of 4 and 63 were also evaluated in vitro using equilibrium dialysis method. 1 µM of the compound was assessed in brain homogenate in a dialysis block for 5 hours at 37° C. Samples from the donor and receiver sides were analyzed by LC-MS/MS. Brain protein bound and unbound fractions were calculated using the equations mentions above (Equations 1 and 2). Due to extensive protein binding, 4 was diluted further 4× for the brain homogenate measurement. The fu,brain of 4 and 63 were 0.29% and 0.1% respectively.

Unbound Brain to Plasma Ratios (Kpuu,brain)

Based on the brain and plasma concentrations obtained above (Table 3A) and fu,brain values obtained above, unbound brain to plasma ratios ($K_{puu}$, brain) were calculated for 4 and 63 as follows:

| | Total Mean Concentration (ng/mL) | Unbound | $K_{puu}$,brain |
|---|---|---|---|
| Compound 4 | | | |
| Brain | 183 | 0.53 | 0.024 |
| Plasma | 1053 | 21.9 | |
| Compound 63 | | | |
| Brain | 1703 | 1.7 | 0.84 |
| Plasma | 1010 | 2.02 | |

Compound 4 presents a highly superior low $K_{p,uu}$,brain (Mean=0.024) as compared to 63 (Mean=0.84). Unbound drug concentration in a tissue is the free drug available to exert its pharmacological effect in the tissue compartment. Since 4 has very low $K_{p,uu}$,brain as compared to 63, it means that the amount of 4 available in the brain to exert its pharmacological effect is very low as compared to 63.

Alternatively, rat brain protein binding of compounds 4 and 63 was evaluated in vitro by employing 300 um thick rat brain slices (striatum area) in an incubation tray. The fu,brain of compounds 4 and 63 by this method was 0.329% and 0.057% respectively. In that case, the $K_{p,uu}$, brain of 4 and 63 are 0.028 and 0.044 respectively.

Kp, Kp,uu (brain homogenate) and Kp,uu (brain slice) results are listed in Table 3B for additional compounds of disclosure prepared according to the examples. The results in Table 3B were obtained as per the methods described above.

TABLE 3B

| Compound No. | Rat Kp | Rat Kp, uu Homogenate | Rat Kp, uu Brain slice |
|---|---|---|---|
| 1 | 0.20 | 0.04 | 0.02 |
| 2 | 0.37 | 0.07 | 0.03 |
| 3 | 0.16 | 0.03 | 0.01 |
| 5 | 0.12 | 0.03 | 0.01 |
| 6 | 0.19 | 0.004 | 0.01 |
| 7 | 0.39 | 0.06 | 0.03 |
| 8 | 0.43 | 0.12 | 0.05 |
| 9 | 0.18 | 0.04 | 0.02 |
| 10 | 0.23 | 0.16 | 0.03 |
| 11 | 0.12 | 0.09 | 0.01 |
| 12 | 0.33 | 0.09 | 0.05 |
| 13 | 0.17 | —* | 0.01 |
| 14 | 0.35 | 0.22 | 0.04 |
| 15 | 0.90 | 0.62 | 0.09 |
| 16 | 0.93 | 0.16 | 0.10 |
| 17 | 0.19 | 0.04 | 0.02 |
| 18 | 0.10 | 0.06 | 0.02 |
| 19 | 0.13 | 0.05 | 0.04 |
| 20 | 0.12 | 0.03 | 0.01 |
| 21 | 0.18 | 0.36 | 0.07 |
| 22 | 0.13 | 0.06 | 0.03 |

*no measurement possible due to high protein binding

Assessment of Compounds as Potential Substrate of P-Glycoprotein

The potential for compounds prepared according to the examples to be substrates of the human P-glycoprotein (P-gp) was evaluated in vitro on Multidrug Resistance Mutation 1-Mardin-Darby Canine Kidney (MDR1-MDCK)) (Mardin-Darby Canine Kidney) cell monolayers overexpressing P-gp grown on permeable supports. Elacridar was used as a positive control inhibitor of the P-gp mediated quinidine transport. A higher efflux ratio of P-gp means that the compound is pushed out of the brain tissue by the transporter.

Assessment of pharmacokinetics following single intravenous and oral administration in rats: 3 Sprague-Dawley rats were employed for each compound for each route of administration (iv or oral). For iv administration, 1 mg/kg (dose volume=5 mL/kg) of each compound was administered by intravenous route via food dorsal vein injection; whereas for oral route, 2.5 mg/kg (dose volume=5 mL/kg) was administered via oral gavage. Blood samples were obtained via tail vein at predose, 0.083, 0.25, 0.5, 1, 2, 4 and 8 hr. In addition, blood samples were also obtained at 24 hr via cardiac puncture (under anesthesia with Isoflurane) for terminal bleeding. All the blood samples were analyzed for the drug concentrations via LC/MS-MS. Pharmacokinetic parameters such as $C_{max}$, $T_{max}$, $AUC_{last}$, $AUC_{inf}$, $MRT_{last}$, $MRT_{inf}$, $T_{1/2}$, $V_{ss}$ and CL were obtained by non-compartmental analysis (NCA). Further, unbound clearance (CLu) was obtained as follows:

$$Cl_u = Cl/f_{u,plasma}.$$

% F was calculated as follows:

$$\% F = [AUC_{inf}(\text{oral})/\text{Dose}]/[AUC_{inf}(\text{iv})/\text{Dose}] * 100$$

(Zhivkova & Doytchinova, Molecular Pharmaceuticals 10:3758-68 (2013)).

TABLE 3C

| Compound No. | MDR1-MDCK Papp/efflux ratio | Rat IV PK Cl (Clu) (mL/min/kg) | % F |
|---|---|---|---|
| 1 | 1.1/6.5 | 37 (2103) | 55 |
| 2 | 2.6/6.5 | 20 (1488) | 72 |
| 3 | 3.8/3.7 | 16 (887) | 70 |
| 4 | 5.5/6.9 | 12 (582) | 80 |
| 5 | 2.4/15 | 31 (1714) | 53 |
| 6 | 2.4/9.6 | 31 (1594) | 43 |
| 7 | 4.5/1.7 | 9 (687) | 56 |
| 9 | 4.1/3.7 | 12 (731) | 49 |
| 12 | 1.8/9.3 | 89 (6378) | — |
| 13 | 1.4/17 | 37 (2193) | 46 |

Example 5: CYP Inhibition Data

In vitro studies in human liver microsomes were run according the standard method. In summary, seven different concentration of the test article or a single concentration of a positive control were co-incubated with a single concentration the probe substrate for each of the CYP450 enzyme in pooled human liver microsomes for 5-10 minutes and then the reactions were terminated by addition of 0.1% formic acid in acetonitrile. The samples were then analyzed by LC-MS/MS for the quantification of the probe substrate left after the reaction and the $IC_{50}$ values were determined by non-linear regression. The substrates for CYP2C9, CYP2D6, CYP3A4 were diclofenac, dextromethorphan and midazolam/testosterone respectively. The data in Table 4 shows the $IC_{50}$s for CYP inhibition of compounds prepared according to the examples for CYP2C9, CYP2D6, and CYP3A4.

TABLE 4

| Compound Number | CYP2C9 $IC_{50}$ (µM) | CYP2D6 $IC_{50}$ (µM) | CYP3A4 $IC_{50}$ (µM) midazolam | CYP3A4 $IC_{50}$ (µM) testosterone |
|---|---|---|---|---|
| 4 | 7.13 | 10.0 | 10.0 | 10.0 |
| 7 | 0.96 | 10.0 | 10.0 | 7.56 |
| 3 | 6.55 | 10.0 | 10.0 | 3.99 |
| 9 | 8.00 | 10.0 | 8.53 | 5.94 |

Example 6: Monkey Plasma Protein Binding Using iv Infusion, Monkey $K_p$, Monkey $K_{p,uu}$ (Homogenate/Brain Slice)

A single IV bolus dose followed by a 2-hour iv infusion of the compound was administered to the monkey (3 monkeys/compound). Blood was collected from a femoral vein predose, right after the bolus administration and at the end of the infusion. The monkey was euthanized after the infusion and brain tissue was collected. Toxicokinetic evaluation of plasma (obtained by centrifugation of blood) and brain (homogenized in a buffer) was conducted to obtain brain to plasma ratio (Kp) of the compound. Kpuu was calculated by taking into consideration the fu,plasma and fu,brain as discussed above.

TABLE 5

| Compound | Kp (Brain:Plasma) | Kpuu |
|---|---|---|
| 4 | 0.09 | 0.01 |
| 63 | 1.86 | 0.92 |

Example 7: Biochemical Activity Assays for Wild-Type KIT

UT-7 Cell Proliferation with SCF Stimulation Assay as a Measure of Wild-Type KIT Activity UT-7 cells are human megakaryoblastic leukemia cell lines that can be grown in culture with dependence on granulocyte macrophage colony stimulating factor (GM-CSF) or stem cell factor (SCF). UT-7 cells respond to SCF stimulation by activation of the KIT receptor tyrosine kinase and subsequent downstream signaling that can support cell growth and proliferation (Kuriu et al, 1999; Komatsu et al, 1991; Sasaki et al, 1995). Test compounds were assayed for their ability to inhibit SCF-stimulated proliferation of UT-7 cells.

Inhibition of SCF-stimulated UT-7 cell proliferation was assessed using the CellTiter-Glo assay that quantifies the amount of adenosine triphosphate (ATP) present, which is a readout of metabolically active cells and is directly proportional to the number of viable cells in culture. The ability of test compounds to inhibit SCF-stimulated UT-7 cell proliferation was determined using a 10-point dose curve ranging from 25 μM to 95.4 pM of test compound.

UT-7 cells were maintained in IMDM supplemented with 10% FBS, 5 ng/mL GM-CSF and 100 units/mL Penicillin-Streptomycin and grown in a 37° C. humidified tissue culture incubator. UT-7 cells were washed once with serum free, GM-CSF free IMDM. Cells were then resuspended in IMDM containing 4% FBS and 50 ng/mL SCF and seeded at 2500 cells per well in a volume of 22 μL in a 384-well microplate. A 10-point dose concentration series of test compounds (25.0 μM to 95.4 pM) were then added to the cells in a volume of 3.1 μL to each well (0.25% DMSO final concentration) and placed in a tissue culture incubator (5% CO2, 37° C.) for 72 hours. After 3-days with test compound, CellTiter-Glo reagent was prepared fresh and 25 μL of reagent was added to each well. The plate was mixed by shaking for 10 minutes at RT at 300 rpm on a plate shaker. The plate was read on an EnVision plate reader using the Ultra Sensitive Luminescence protocol for a 384-well plate. Data was normalized to 0% and 100% inhibition controls and the IC50 was calculated using Four Parameter Logistic IC50 curve fitting.

Wild-Type KIT Assay

Kd Determinations. For most assays, including wt KIT kinase, kinase-tagged T7 phage strains were prepared in an E. coli host derived from the BL21 strain. E. coli were grown to log-phase and infected with T7 phage and incubated with shaking at 32° C. until lysis. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements were distributed by acoustic transfer (noncontact dispensing) in 100% DMSO. The compounds were then diluted directly into the assays such that the final concentration of DMSO was 0.9%. All reactions were performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM nonbiotinylated affinity ligand) and incubated at room temperature with shaking for 30 minutes. The kinase concentration in the eluates was measured by qPCR.

Binding Constants (Kds). Binding constants (Kds) were calculated with a standard dose-response curve using the Hill equation: Response=Background+Signal−Background 1+(KdHill Slope/DoseHill Slope). The Hill Slope was set to −1. Curves were fitted using a non-linear least square fit with the Levenberg-Marquardt algorithm.

The results obtained in these WT KIT experiments for compounds prepared according to the examples are summarized in Table 7 below. For wild-type KIT binding, the following designations are used: <10.0 nM=A; ≥10.1 nM and <15 nM=B; ≥15.1 nM and <20 nM=C. For proliferation inhibition, the following designations are used: <90.0 nM=A; ≥90.1 nM and <150 nM=B; ≥150.1 nM and <200 nM=C.

TABLE 7

| Compound No. | KIT WT Kd (nM) | KIT (proliferation UT-7 (nM)) |
|---|---|---|
| 1 | A | C |
| 2 | A | C |
| 3 | A | A |
| 4 | C | A |
| 5 | A | A |
| 6 | A | A |
| 7 | B | B |
| 8 | A | A |
| 9 | A | B |
| 10 | A | A |
| 11 | A | B |
| 12 | A | B |
| 13 | A | B |
| 14 | A | C |
| 15 | A | C |
| 16 | A | C |
| 17 | A | B |
| 18 | A | B |
| 19 | A | B |
| 20 | A | B |
| 21 | A | B |
| 22 | A | B |
| Example 63 WO2015/057873 ("63") | C | C |

The invention claimed is:

1. A compound of Formula I:

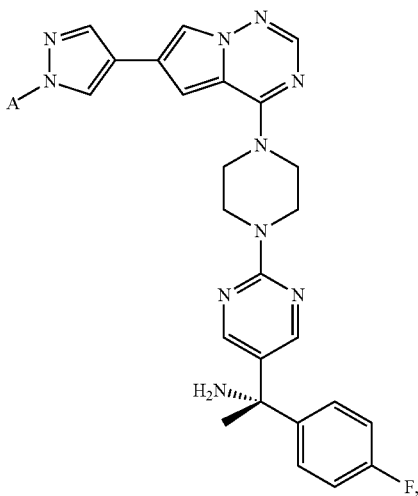

(I)

a pharmaceutically acceptable salt thereof, and/or a solvate of any of the foregoing, wherein:

A is

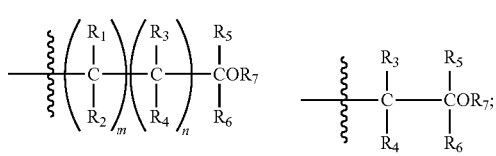

$R_3$ is chosen from hydrogen and methyl;
$R_4$ is chosen from hydrogen and methyl, or $R_3$ and $R_4$ taken together form a cyclopropyl;
$R_5$ is chosen from hydrogen and methyl;
$R_6$ is chosen from hydrogen and methyl, or
$R_5$ and $R_6$ taken together form a cyclopropyl, or
$R_4$ taken together with $R_6$ forms a cyclobutyl; and
$R_7$ is hydrogen.

2. The compound of claim 1, a pharmaceutically acceptable salt thereof, and/or a solvate of any of the foregoing, wherein:

A is:

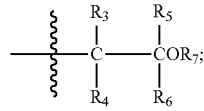

$R_3$ is chosen from hydrogen and methyl;
$R_4$ is chosen from hydrogen and methyl, or $R_3$ and $R_4$ taken together form a cyclopropyl;
$R_5$ is chosen from hydrogen and methyl;
$R_6$ is chosen from hydrogen and methyl; or
$R_5$ and $R_6$ taken together form a cyclopropyl, and
$R_7$ is hydrogen.

3. The compound of claim 1, a pharmaceutically acceptable salt thereof, and/or a solvate of any of the foregoing, wherein A is chosen from

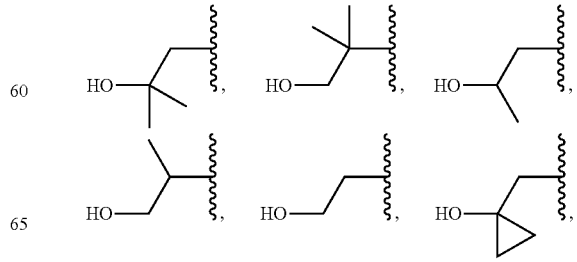

-continued

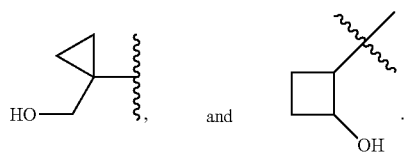
and

4. The compound of claim 1, a pharmaceutically acceptable salt thereof, and/or a solvate of any of the foregoing, wherein A is chosen from

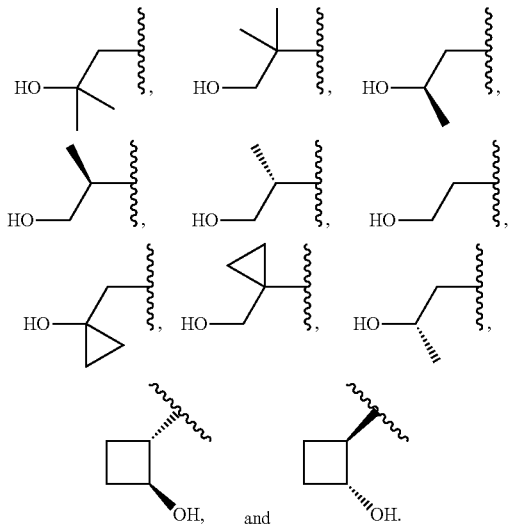

5. The compound of claim 1, a pharmaceutically acceptable salt thereof, and/or a solvate of any of the foregoing, wherein A is chosen from

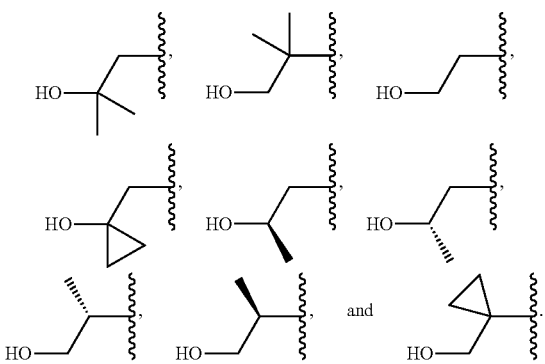
and

6. The compound of claim 5, a pharmaceutically acceptable salt thereof, and/or a solvate of any of the foregoing, wherein A is chosen from

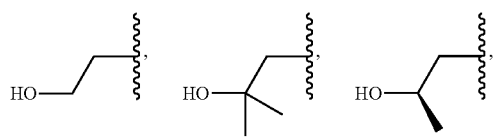

-continued

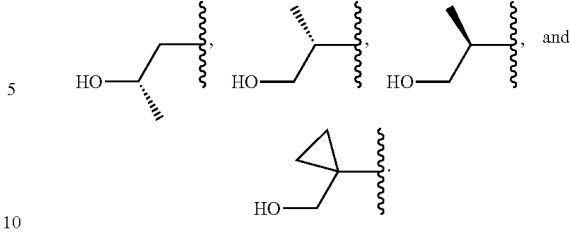

7. The compound of claim 6, a pharmaceutically acceptable salt thereof, and/or a solvate of any of the foregoing, wherein A is chosen from

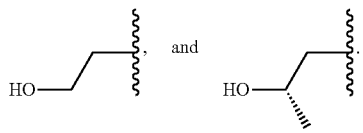

8. A compound (4)

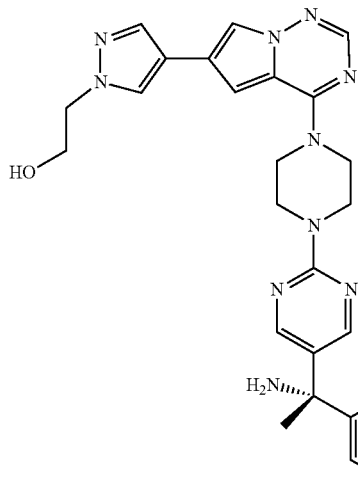

or a pharmaceutically acceptable salt thereof, and/or a solvate of any of the foregoing.

9. The compound of claim 8, (4)

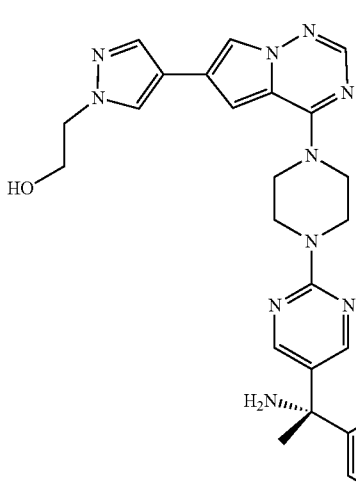

10. A compound

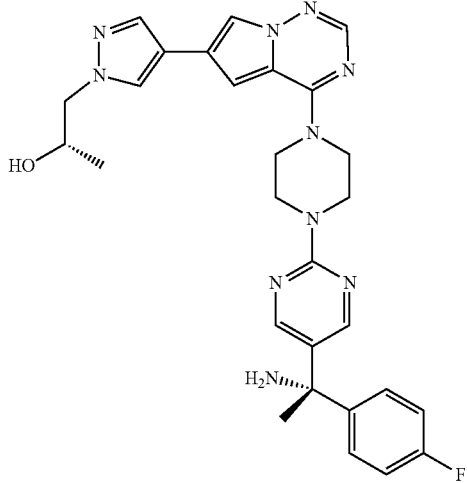

(9)

or a pharmaceutically acceptable salt thereof, and/or a solvate of any of the foregoing.

11. The compound of claim 10

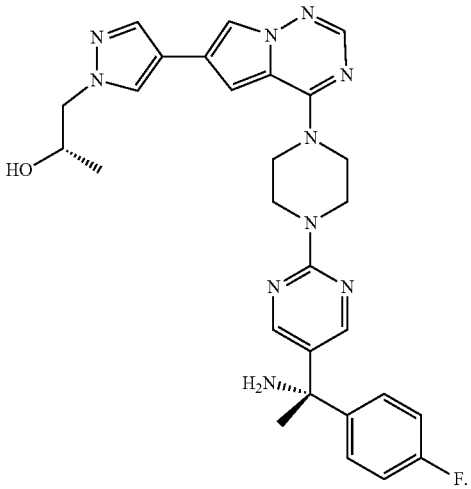

(9)

12. A pharmaceutical composition comprising:
a compound of claim 1, a pharmaceutically acceptable salt thereof, and/or a solvate of any of the foregoing; and
a pharmaceutically acceptable excipient.

13. A pharmaceutical composition comprising:
a compound of claim 8, a pharmaceutically acceptable salt thereof, and/or a solvate of any of the foregoing; and
a pharmaceutically acceptable excipient.

14. A pharmaceutical composition comprising:
a compound of claim 10, a pharmaceutically acceptable salt thereof, and/or a solvate of any of the foregoing; and
a pharmaceutically acceptable excipient.

15. A method of treating a disease or condition in a patient in need thereof, wherein the method comprises administering to the patient a compound of claim 1, a pharmaceutically acceptable salt thereof, and/or a solvate of any of the foregoing, wherein the disease or condition is chosen from systemic mastocytosis and gastrointestinal stromal tumors.

16. The method of claim 15, wherein the disease or condition is systemic mastocytosis.

17. The method of claim 16, wherein the systemic mastocytosis is chosen from indolent systemic mastocytosis and smoldering systemic mastocytosis.

18. A compound

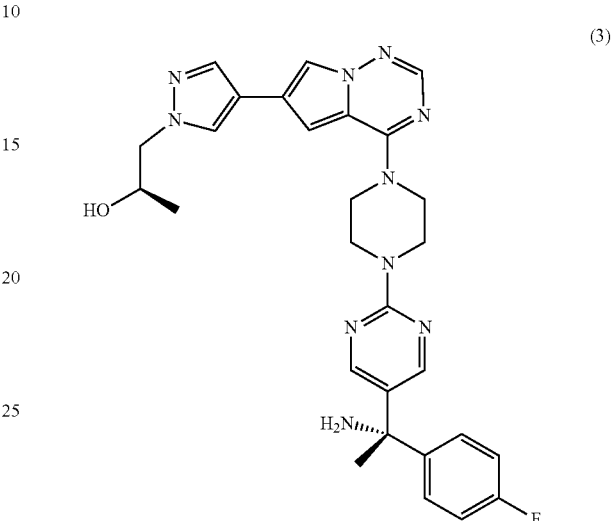

(3)

or a pharmaceutically acceptable salt thereof, and/or a solvate of any of the foregoing.

19. The compound of claim 18,

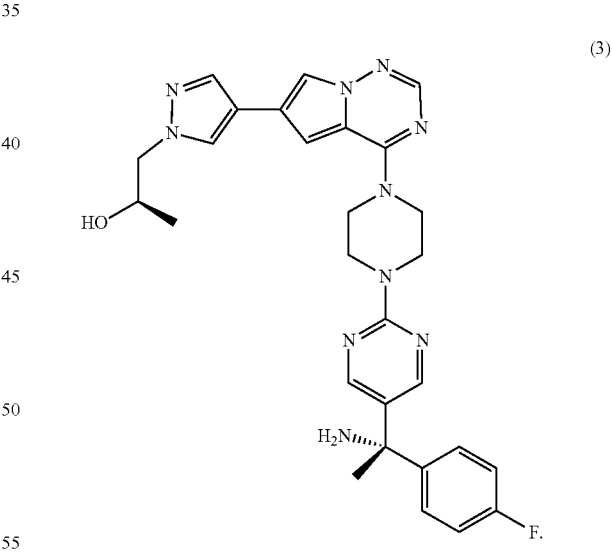

(3)

20. A pharmaceutical composition comprising:
a compound of claim 18, a pharmaceutically acceptable salt thereof, and/or a solvate of any of the foregoing; and
a pharmaceutically acceptable excipient.

21. A method of treating a disease or condition in a patient in need thereof, wherein the method comprises administering to the patient a compound of claim 18, a pharmaceutically acceptable salt thereof, and/or a solvate of any of the foregoing, wherein the disease or condition is chosen from systemic mastocytosis and gastrointestinal stromal tumors.

22. The method of claim 21, wherein the disease or condition is indolent systemic mastocytosis.

23. A compound

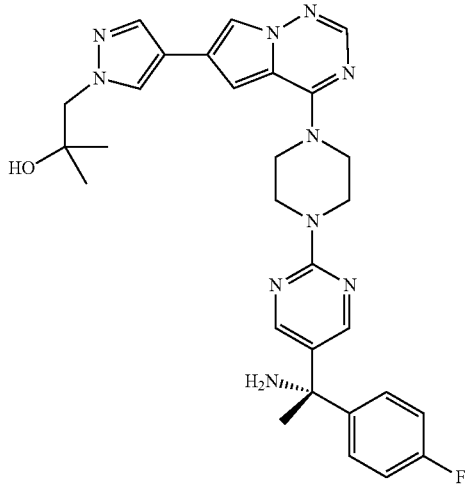

(1)

or a pharmaceutically acceptable salt thereof, and/or a solvate of any of the foregoing.

24. The compound of claim 23,

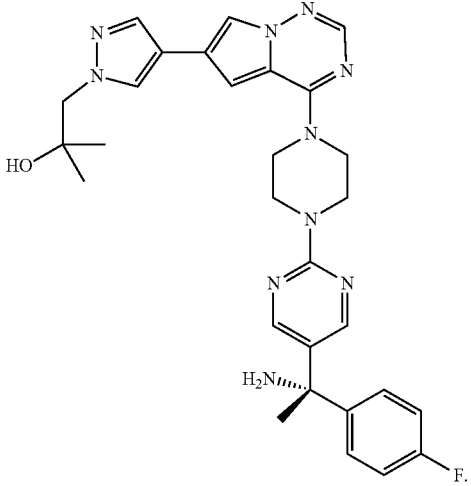

(1)

25. A pharmaceutical composition comprising:
a compound of claim 23, a pharmaceutically acceptable salt thereof, and/or a solvate of any of the foregoing; and
a pharmaceutically acceptable excipient.

26. A method of treating a disease or condition in a patient in need thereof, wherein the method comprises administering to the patient a compound of claim 23, a pharmaceutically acceptable salt thereof, and/or a solvate of any of the foregoing, wherein the disease or condition is chosen from systemic mastocytosis and gastrointestinal stromal tumors.

27. The method of claim 26, wherein the disease or condition is indolent systemic mastocytosis.

28. A compound

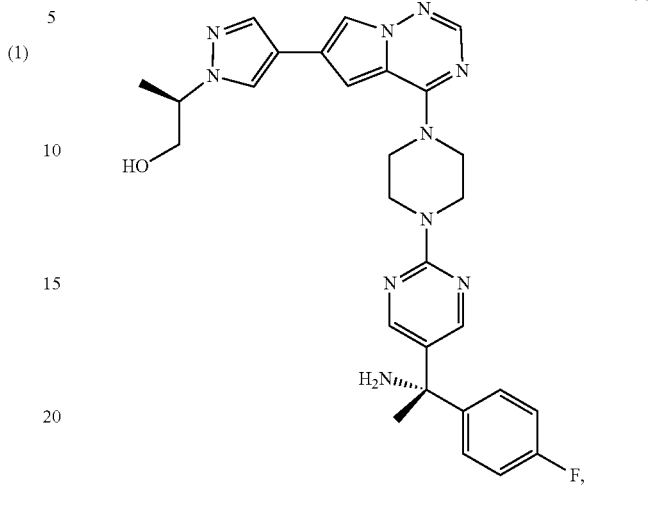

(5)

or a pharmaceutically acceptable salt thereof, and/or a solvate of any of the foregoing.

29. The compound of claim 28,

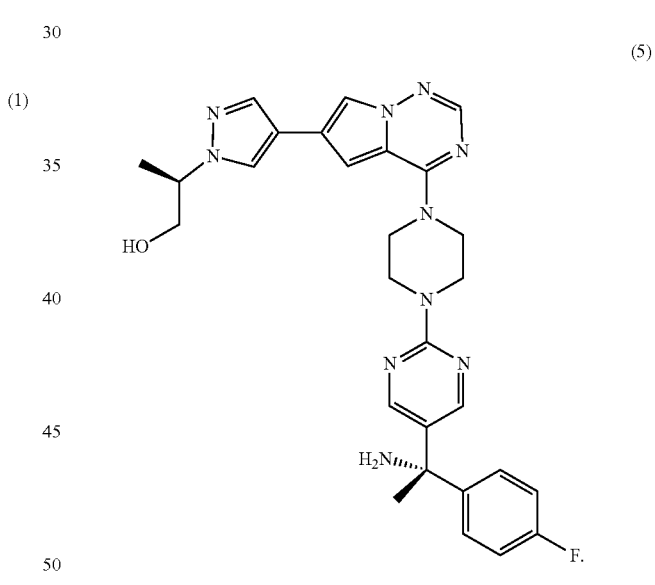

(5)

30. A pharmaceutical composition comprising:
a compound of claim 28, a pharmaceutically acceptable salt thereof, and/or a solvate of any of the foregoing; and
a pharmaceutically acceptable excipient.

31. A method of treating a disease or condition in a patient in need thereof, wherein the method comprises administering to the patient a compound of claim 28, a pharmaceutically acceptable salt thereof, and/or a solvate of any of the foregoing, wherein the disease or condition is chosen from systemic mastocytosis and gastrointestinal stromal tumors.

32. The method of claim 31, wherein the disease or condition is indolent systemic mastocytosis.

33. A compound

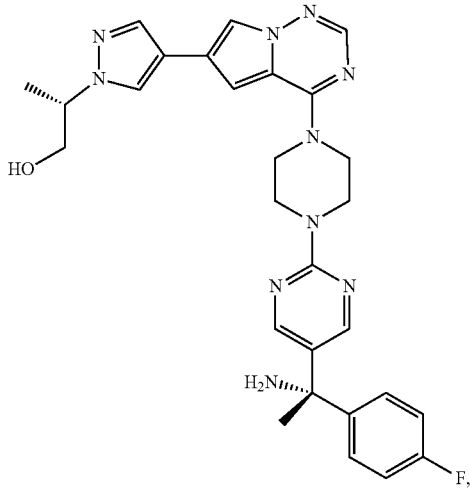

(6)

or a pharmaceutically acceptable salt thereof, and/or a solvate of any of the foregoing.

34. The compound of claim 33,

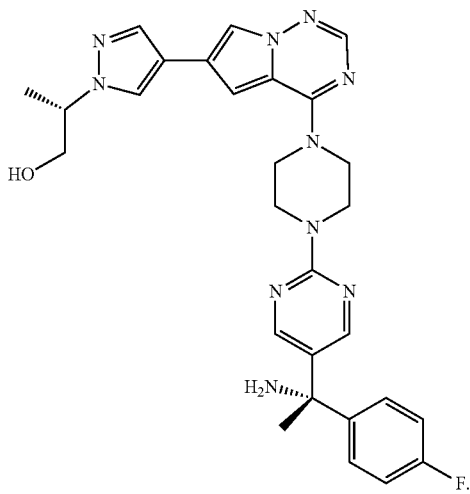

(6)

35. A pharmaceutical composition comprising:
a compound of claim 33, a pharmaceutically acceptable salt thereof, and/or a solvate of any of the foregoing; and
a pharmaceutically acceptable excipient.

36. A method of treating a disease or condition in a patient in need thereof, wherein the method comprises administering to the patient a compound of claim 33, a pharmaceutically acceptable salt thereof, and/or a solvate of any of the foregoing, wherein the disease or condition is chosen from systemic mastocytosis and gastrointestinal stromal tumors.

37. The method of claim 36, wherein the disease or condition is indolent systemic mastocytosis.

38. A method of treating a disease or condition in a patient in need thereof, wherein the method comprises administering to the patient a compound of claim 8, a pharmaceutically acceptable salt thereof, and/or a solvate of any of the foregoing, wherein the disease or condition is chosen from systemic mastocytosis and gastrointestinal stromal tumors.

39. The method of claim 38, wherein the disease or condition is indolent systemic mastocytosis.

40. A method of treating a disease or condition in a patient in need thereof, wherein the method comprises administering to the patient a compound of claim 10, a pharmaceutically acceptable salt thereof, and/or a solvate of any of the foregoing, wherein the disease or condition is chosen from systemic mastocytosis and gastrointestinal stromal tumors.

41. The method of claim 40, wherein the disease or condition is indolent systemic mastocytosis.

* * * * *

UNITED STATES PATENT AND TRADEMARK OFFICE
CERTIFICATE OF CORRECTION

PATENT NO. : 10,829,493 B2
APPLICATION NO. : 16/842969
DATED : November 10, 2020
INVENTOR(S) : Thomas A. Dineen Page 1 of 1

It is certified that error appears in the above-identified patent and that said Letters Patent is hereby corrected as shown below:

In the Claims

At Column 93, Claim number 1, Line numbers 56-63, replace

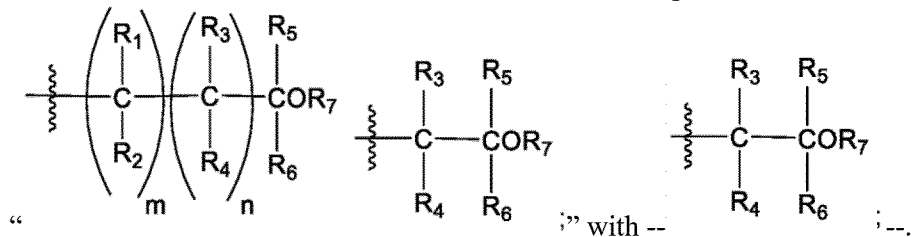

Signed and Sealed this
Twenty-ninth Day of December, 2020

Andrei Iancu
*Director of the United States Patent and Trademark Office*